(12) United States Patent
Nagase et al.

(10) Patent No.: US 6,187,782 B1
(45) Date of Patent: Feb. 13, 2001

(54) MORPHINANE DERIVATIVES AND MEDICINAL USE THEREOF

(75) Inventors: Hiroshi Nagase; Hideaki Fujii, both of Kamakura; Takashi Endoh, Chigasaki; Koji Kawai, Kamakura, all of (JP)

(73) Assignee: Toray Industries, Inc., Tokyo (JP)

(*) Notice: Under 35 U.S.C. 154(b), the term of this patent shall be extended for 0 days.

(21) Appl. No.: 09/194,366

(22) PCT Filed: Mar. 27, 1998

(86) PCT No.: PCT/JP98/01376

§ 371 Date: Nov. 25, 1998

§ 102(e) Date: Nov. 25, 1998

(87) PCT Pub. No.: WO98/43978

PCT Pub. Date: Oct. 8, 1998

(30) Foreign Application Priority Data

Mar. 27, 1997 (JP) .................................................. 9-076340

(51) Int. Cl.[7] ...................... A61K 31/445; C07D 491/02
(52) U.S. Cl. .......................... 514/279; 546/41; 546/46; 546/39
(58) Field of Search ............................ 514/279, 282; 546/39, 41, 46

(56) References Cited

FOREIGN PATENT DOCUMENTS

| 49-61188 | 6/1974 | (JP) . |
| 61-63658 | 4/1986 | (JP) . |
| 3-163083 | 7/1991 | (JP) . |
| 93-15081 | 8/1993 | (WO) . |

OTHER PUBLICATIONS

Lessor, R.A. et al.: Probes for narcotic receptor mediated phenomenon. J. med. Chem. vol. 29, pp. 2136–2141, 1986.*
Jacobson, A.E. et al.: Probes for narcotic receptor mediated phenomenon. Life Sci. vol. 33, suppl. 1, pp. 159–162, 1983.*
Piggot, N.G. et al.: Molecular modeling of fumaramido and cinnamoylamido derivatives in epoxy–morphinans. Analgesia. vol. 1, pp. 647–650, 1995.*

* cited by examiner

Primary Examiner—John Kight
Assistant Examiner—Charanjit S. Aulakh
(74) Attorney, Agent, or Firm—Birch, Stewart, Kolasch & Birch, LLP

(57) ABSTRACT

Novel morphinan derivatives and pharmaceutically acceptable acid addition salts thereof as compounds having abilities to bind to opioid ε-receptor, which have agonist or antagonist activities, are disclosed. The morphinan derivatives according to the present invention are represented by the formula (I).

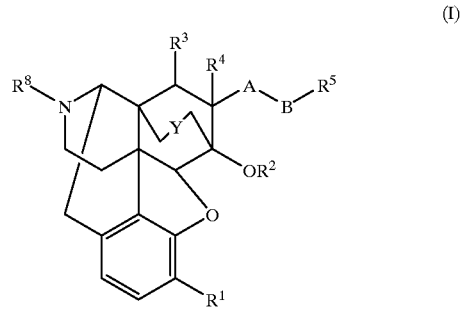

8 Claims, No Drawings

MORPHINANE DERIVATIVES AND MEDICINAL USE THEREOF

This application is the national phase under 35 U.S.C. §371 of prior PCT International Application No. PCT/JP98/01376 which has an International filing date of Mar. 27, 1998 which designated the United States of America now WO 98/43978 published Oct. 8, 1998.

TECHNICAL FIELD

The present invention relates to novel morphinan derivatives and compounds having abilities to bind to opioid ε-receptor containing the same as effective components as well as to medical uses thereof.

BACKGROUND ART

As the receptor relating to analgesic action on central nerve, opioid receptors have been revealed, and the opioid receptors are classified into three types $\mu$, $\delta$ and $\kappa$. β-endorphin which is one of the endogeneous opioid peptides showing strong analgesic action, has been considered as a non-selective agonist having affinities to both $\mu$ and $\delta$ receptors. However, detailed study using antagonists each of which is selective to each type of the opioid receptors has revealed that β-endorphin has an additional site on which it acts, in addition to the known three types of receptors. As the action site, ε-type receptor is drawing attention recently.

Morphine having morphinan skeleton is known as a strong analgesic for a long time, and is widely used now. However, this drug has serious side effects which are clinically problematic, such as addiction, respiratory depression and smooth muscle-depressomotor action (constipation), and it has been clarified that these side effects are exhibited through $\mu$ receptors. Since use of the drug requires strict control, a strong analgesic acting on the central nerve, which may be safely used, is desired.

On the other hand, the above-mentioned β-endorphin has been reported not to show cross tolerance to morphine which is $\mu$-agonist. Agonists at ε-receptor are expected as analgesics free from the side effects which the $\mu$-agonists have, and are thought to be applicable not only to a pain such as postoperative pain or cancer pain, but also widely to general pains, so that it is thought to be highly useful. Further, since it does not have the cross tolerance, it is expected that the drug is effective to patients having tolerance to an analgesic such as morphine.

As is apparent from the above-mentioned study of the opioid receptors, it is known that antagonists play important roles in the pharmacological studies of receptors, and antagonists at ε-receptor are expected to be important tools in the pharmacological study of this receptor.

DISCLOSURE OF THE INVENTION

That is, an object of the present invention is to provide a compound which binds to opioid ε-receptor, more specifically, to provide an opioid ε-receptor agonist or antagonist.

The present inventors intensively studied to discover that the morphinan derivatives represented by the formula (I) are compounds having abilities to bind to opioid ε-receptor, and have ε-receptor agonist activity or antagonist activity, thereby completing the present invention.

That is, the present invention provides a morphinan derivative of the formula (I):

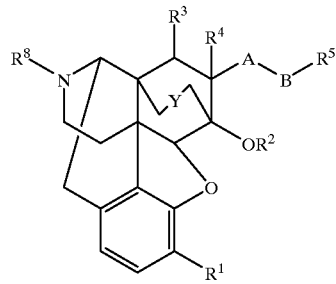

{wherein
Y is single bond or double bond;
$R^1$ is hydrogen, hydroxy, $C_1$–$C_5$ alkoxy, $C_1$–$C_5$ alkanoyloxy or $C_7$–$C_{13}$ aralkyloxy;
$R^2$ is hydrogen or $C_1$–$C_5$ alkyl;
$R^3$ and $R^4$ independently are hydrogen, fluorine, chlorine, bromine, iodine, $C_1$–$C_5$ alkyl or phenyl;
A is —X(=O)—$NR_6$— or —$NR^6$—X(=O)—, wherein X is carbon or S=O, $R^6$ is hydrogen, $C_1$–$C_5$ alkyl, $C_3$–$C_7$ alkenyl, $C_3$–$C_7$ alkynyl, $C_6$–$C_{12}$ aryl or $C_7$–$C_{13}$ aralkyl;
B is valence bond, $C_1$–$C_{14}$ straight or branched alkylene (wherein said $C_1$–$C_{14}$ straight or branched alkylene may be substituted with at least one substituent selected from the group consisting of $C_1$–$C_5$ alkoxy, $C_1$–$C_5$ alkanoyloxy, hydroxy, fluorine, chlorine, bromine, iodine, amino, nitro, cyano, trifluoromethyl, phenyl and phenoxy, and that 1 to 3 methylene groups therein may be substituted by carbonyl group), $C_2$–$C_{14}$ linear or branched acyclic unsaturated hydrocarbon containing 1 to 3 double bonds and/or triple bonds (wherein said $C_2$–$C_{14}$ linear or branched acyclic unsaturated hydrocarbon may be substituted with at least one substituent selected from the group consisting of $C_1$–$C_5$ alkoxy, $C_1$–$C_5$ alkanoyloxy, hydroxy, fluorine, chlorine, bromine, iodine, amino, nitro, cyano, trifluoromethyl, phenyl and phenoxy, and that 1 to 3 methylene groups therein may be substituted by carbonyl group), $C_1$–$C_{14}$ straight or branched saturated or unsaturated hydrocarbon containing 1 to 5 thioether bonds, ether bonds and/or amino bonds (wherein 1 to 3 methylene groups in said $C_1$–$C_{14}$ straight or branched saturated or unsaturated hydrocarbon may be substituted by carbonyl group);
$R^5$ is hydrogen, cyano, or an organic group having the following skeleton:

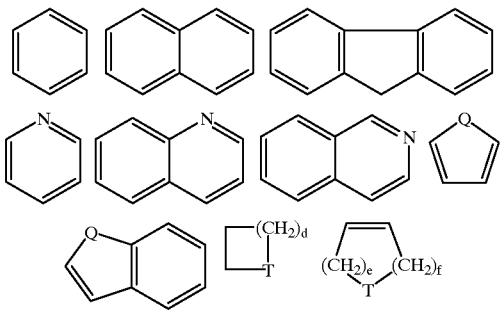

(wherein Q is —NH—, —S— or —O—, T is —$CH_2$—, —NH—, —S— or —O—, d is a number from 0 to 5, e and f independently are numbers of not less than 0 whereas the total of e and f is not more than 5)
(wherein said organic group may be substituted with at least one substituent selected from the group consisting of $C_1$–$C_5$ alkyl, $C_1$–$C_5$ alkoxy, $C_1$–$C_5$ alkanoyloxy, hydroxy, $C_1$–$C_5$ alkoxycarbonyl, fluorine, chlorine, bromine, iodine, amino, nitro, cyano, isothiocyanato, trifluoromethyl, phenyl, phenoxy and methylenedioxy), wherein —B—$R^5$, $R^6$ and nitrogen to which —B—$R^5$ and $R^6$ are bound may cooperatively form a heterocyclic ring selected from the group consisting of morpholine, piperidine, pyrrolidine, piperazine, N-methylpiperazine, N-phenylpiperazine, indoline, tetrahydroquinoline and tetrahydroisoquinoline when A is —X(=O)—$NR^6$—, or —B—$R^5$ and $R^6$ may cooperatively form $C_2$–$C_6$ alkylene or

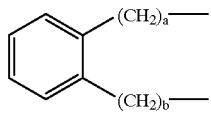

(wherein a and b independently are numbers of not less than 0, the total of a and b being not more than 4) when A is —$NR^6$—X(=O)—;
$R^8$ is $C_4$–$C_7$ cycloalkylalkyl or $C_7$–$C_{13}$ aralkyl} or a pharmaceutically acceptable acid addition salt thereof.

The present invention also provides a pharmaceutical which has ability to bind to opioid ε-receptor, more specifically, an opioid ε-receptor agonist or antagonist, comprising as an effective component said morphinan derivative or the pharmaceutically acceptable acid addition salt thereof according to the present invention.

BEST MODE FOR CARRYING OUT THE INVENTION

As mentioned above, the morphinan derivatives according to the present invention are represented by the above-described formula (I). In formula (I), $R^1$ may preferably be hydrogen, hydroxy, methoxy, ethoxy, acetoxy, propionyloxy or benzyloxy, more preferably hydrogen, hydroxy, methoxy or acetoxy.

$R^2$ may preferably be hydrogen or methyl.

$R^3$ and $R^4$ may be the same or different, and may preferably be hydrogen, chlorine, bromine, iodine, methyl, ethyl or phenyl, more preferably hydrogen, methyl or phenyl. "A" may preferably be carbamoyl, acylamino or sulfonylamino, more prefeably carbamoyl or acylamino. B may preferably be valence bond, —$(CH_2)_n$— (n is a number from 0 to 6, hereinafter indicated as "n=0–6"), —$(CH_2)_n$—CH=CH—$(CH_2)_m$— (n=1–2, m=0–2), —$(CH_2)_n$—CH=CH—CH=CH—$(CH_2)_m$— (n and m are independently numbers of 0 to 2 (hereinafter indicated as "n,m=0–2"), —$(CH_2)_n$—C≡C—$(CH_2)_m$— (n,m=0–2), —$(CH_2)_n$—C(=O)— (n=1–4), —$(CH_2)_n$—O—$(CH_2)_m$— (n=1–3, m=0–3), —$(CH_2)_n$—S—$(CH_2)_m$— (n=1–3, m=0–3), or —$(CH_2)_n$—NH—$(CH_2)_m$— (n=1–3, m=0–3), more preferably —$(CH_2)_n$— (n=0–6), —$(CH_2)_n$—CH=CH— (n=1–2), —$(CH_2)_n$—CH=CH—CH=CH— (n=0–2), —$(CH_2)_n$—C≡C— (n=0–2), —$CH_2$—C(=O)—, —$(CH_2)_n$—O—$(CH_2)_m$— (n≠0,n+m=1–3), —$(CH_2)_n$—S—$(CH_2)_m$— (n≠0, n+m=1–3), or —$(CH_2)_n$—NH—$(CH_2)_m$— (n≠0, n+m=1–3). $R^5$ may preferably be hydrogen or an organic group having the following skeleton:

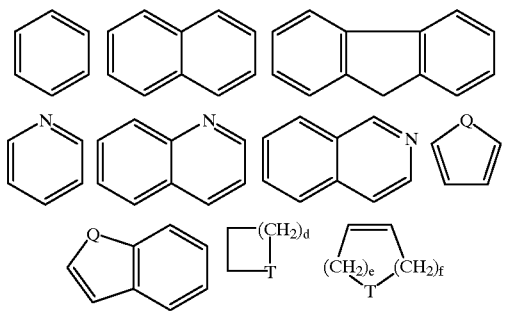

(wherein Q is —NH—, —S— or —O—, T is —$CH_2$—, —NH—, —S— or —O—, d is a number from 0 to 5, e and f independently are numbers of not less than 0 whereas the total of e and f is not more than 5)
(wherein said organic group may be substituted with at least one substituent selected from the group consisting of $C_1$–$C_5$ alkyl, $C_1$–$C_5$ alkoxy, $C_1$–$C_5$ alkanoyloxy, hydroxy, $C_1$–$C_5$ alkoxycarbonyl, fluorine, chlorine, bromine, iodine, amino, nitro, cyano, isothiocyanato, trifluoromethyl, phenyl, phenoxy and methylenedioxy). The organic groups represented by the above-described 10 formulae may be bound to B at an optional carbon atom or nitrogen atom. Preferred examples of $R^5$ include hydrogen, phenyl, 2-fluorophenyl, 3-fluorophenyl, 4-fluorophenyl, 2-chlorophenyl, 3-chlorophenyl, 4-chlorophenyl, 2-bromophenyl, 3-bromophenyl, 4-bromophenyl, 2-methylphenyl, 3-methylphenyl, 4-methylphenyl, 2-methoxyphenyl, 3-methoxyphenyl, 4-methoxyphenyl, 2-trifluoromethylphenyl, 3-trifluoromethylphenyl, 4-trifluoromethylphenyl, 2-methoxycarbonylphenyl, 3-methoxycarbonylphenyl, 4-methoxycarbonylphenyl, 2-phenylphenyl, 3-phenylphenyl, 4-phenylphenyl, 2-phenoxyphenyl, 3-phenoxyphenyl, 4-phenoxyphenyl, 2-pyridyl, 3-pyridyl, 4-pyridyl, 2-furyl, 3-furyl, 2-thienyl and 3-thienyl. However, needless to say, $R^5$ is not restricted thereto. $R^6$ may preferably be hydrogen, $C_1$–$C_5$ alkyl, allyl, propargyl, phenyl, benzyl or phenethyl, more preferably hydrogen, methyl or ethyl. In cases where A is —X(=O)—$NR^6$—, it is also preferred that —B—$R^5$, $R^6$ and the nitrogen to which —B—$R^5$ and $R^6$ are bound cooperatively form N-phenylpiperazine, indoline, tetrahydroquinoline or tetrahydroisoquinoline.

As for the combination of A, B and $R^5$, although any of the above-described A, B and $R^5$ may be combined, in cases where A is —NH—(C=O)—, B preferably is not —CH=CH— and $R^5$ is not hydrogen.

$R^8$ may preferably be cyclopropylmethyl, cyclobutylmethyl, benzyl or phenethyl, more preferably cyclopropylmethyl or phenethyl.

Examples of the pharmaceutically preferable acid addition salts include inorganic salts such as hydrochloric acid salt, sulfuric acid salt, nitric acid salt, hydrobromic acid salt, hydroiodic acid salt and phosphoric acid salt; organic carboxylic acid salts such as acetic acid salt, lactic acid salt, citric acid salt, oxalic acid salt, glutaric acid salt, malic acid salt, tartaric acid salt, fumaric acid salt, mandelic acid salt, maleic acid salt, benzoic acid salt and phthalic acid salt; and organic sulfonic acid salts such as methanesulfonic acid salt, ethanesulfonic acid salt, benzenesulfonic acid salt, p-toluenesulfonic acid salt and camphorsulfonic acid salt. Among these, hydrochloric acid salt, hydrobromic acid salt, phosphoric acid salt, tartaric acid salt and methanesulfonic acid salt are especially preferred, although the pharmaceutically acceptable acid addition salts are not restricted thereto.

Among the compounds represented by the formula (I), the Compound 1 wherein Y is double bond, $R^1$ is hydroxy, $R^2$, $R^3$ and $R^4$ are hydrogen, A is α-X(=O)—$NR^6$—, X is carbon, $R^6$ is hydrogen, B is —(CH$_2$)$_2$—, $R^5$ is phenyl and $R^8$ is cyclopropylmethyl, represented by the formula:

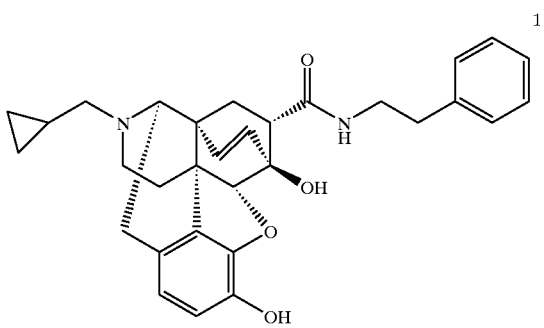

is named N-cyclopropylmethyl-7α-phenethylcarbamoyl-6,14-endoethenotetrahydronormorphide.

Among the compounds represented by the formula (I), the Compound 2 wherein Y is double bond, $R^1$ is methoxy, $R^2$, $R^3$ and $R^4$ are hydrogen, A is α-X(=O)—$NR^6$—, X is carbon, $R^6$ is hydrogen, B is —(CH$_2$)$_2$—, $R^5$ is phenyl and $R^8$ is cyclopropylmethyl, represented by the formula:

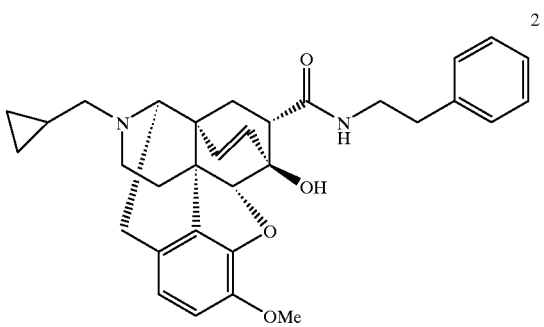

is named N-cyclopropylmethyl-7α-phenethylcarbamoyl-6,14-endoethenotetrahydronorcodide.

Among the compounds represented by the formula (I), the Compound 3 wherein Y is single bond, $R^1$ is hydroxy, $R^2$ is methyl, $R^3$ and $R^4$ are hydrogen, A is α-$NR^6$—X(=O)—, X is carbon, $R^6$ is hydrogen, B is —(CH$_2$)$_2$—, $R^5$ is phenyl and $R^8$ is cyclopropylmethyl, represented by the formula:

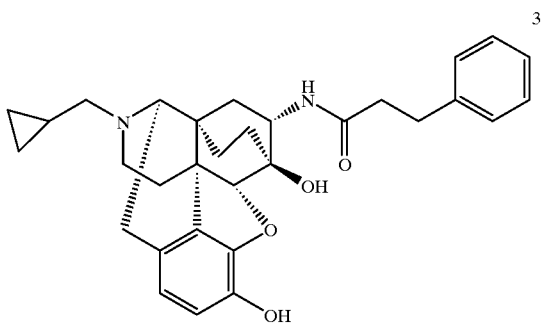

is named N-cyclopropylmethyl-7α-(3-phenylpropionylamino)-6,14-endoethanotetrahydronororipavine.

Among the compounds represented by the formula (I), the Compound 4 wherein Y is single bond, $R^1$ is methoxy, $R^2$ is methyl, $R^3$ and $R^4$ are hydrogen, A is α-$NR^6$—X(=O)—, X is carbon, $R^6$ is hydrogen, B is —(CH$_2$)$_2$—, $R^5$ is phenyl and $R^8$ is cyclopropylmethyl, represented by the formula:

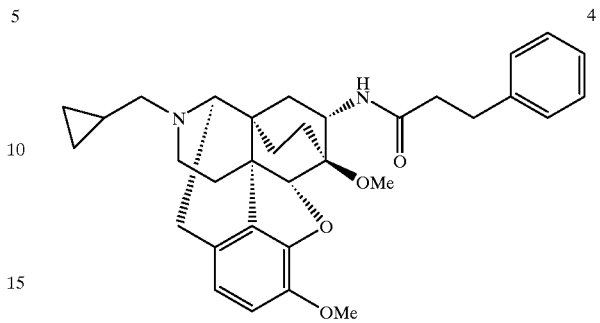

is named N-cyclopropylmethyl-7α-(3-phenylpropionylamino)-6,14-endoethanotetrahydronorthebaine.

According to these nomenclatures, specific examples of the compounds according to the present invention include N-cyclopropylmethyl-7α-phenylcarbamoyl-6,14-endoethenotetrahydronormorphide, N-cyclopropylmethyl-7β-phenylcarbamoyl-6,14-endoethenotetrahydronormorphide, N-cyclopropylmethyl-7α-phenylcarbamoyl-6,14-endoethanotetrahydronormorphide, N-cyclopropylmethyl-7β-phenylcarbamoyl-6,14-endoethanotetrahydronormorphide, N-cyclopropylmethyl-7α-phenylcarbamoyl-6,14-endoethenotetrahydronorcodide, N-cyclopropylmethyl-7β-phenylcarbamoyl-6,14-endoethenotetrahydronorcodide, N-cyclopropylmethyl-7α-phenylcarbamoyl-6,14-endoethanotetrahydronorcodide, N-cyclopropylmethyl-7β-phenylcarbamoyl-6,14-endoethanotetrahydronorcodide, N-cyclopropylmethyl-7α-phenylcarbamoyl-6,14-endoethenotetrahydronororipavine, N-cyclopropylmethyl-7β-phenylcarbamoyl-6,14-endoethenotetrahydronororipavine, N-cyclopropylmethyl-7α-phenylcarbamoyl-6,14-endoethanotetrahydronororipavine, N-cyclopropylmethyl-7β-phenylcarbamoyl-6,14-endoethanotetrahydronororipavine, N-cyclopropylmethyl-7α-phenylcarbamoyl-6,14-endoethenotetrahydronorthebaine, N-cyclopropylmethyl-7β-phenylcarbamoyl-6,14-endoethenotetrahydronorthebaine, N-cyclopropylmethyl-7α-phenylcarbamoyl-6,14-endoethanotetrahydronorthebaine, N-cyclopropylmethyl-7β-phenylcarbamoyl-6,14-endoethanotetrahydronorthebaine, N-cyclopropylmethyl-7α-benzylcarbamoyl-6,14-endoethenotetrahydronormorphide, N-cyclopropylmethyl-7β-benzylcarbamoyl-6,14-endoethenotetrahydronormorphide, N-cyclopropylmethyl-7α-benzylcarbamoyl-6,14-endoethanotetrahydronormorphide, N-cyclopropylmethyl-7β-benzylcarbamoyl-6,14-endoethanotetrahydronormorphide, N-cyclopropylmethyl-7α-benzylcarbamoyl-6,14-endoethenotetrahydronorcodide, N-cyclopropylmethyl-7β-benzylcarbamoyl-6,14-endoethenotetrahydronorcodide, N-cyclopropylmethyl-7α-benzylcarbamoyl-6,14-endoethanotetrahydronorcodide, N-cyclopropylmethyl-7β-benzylcarbamoyl-6,14-endoethanotetrahydronorcodide, N-cyclopropylmethyl-7α-benzylcarbamoyl-6,14-endoethenotetrahydronororipavine, N-cyclopropylmethyl-7β-benzylcarbamoyl-6,14- endoethenotetrahydronororipavine, N-cyclopropylmethyl-7α-benzylcarbamoyl-6,14-endoethanotetrahydronororipavine, N-cyclopropylmethyl-7β-benzylcarbamoyl-6,14-endoethanotetrahydronororipavine, N-cyclopropylmethyl-7α-benzylcarbamoyl-6,14-endoethenotetrahydronorthebaine, N-cyclopropylmethyl-7β-benzylcarbamoyl-6,14-endoethenotetrahydronorthebaine, N-cyclopropylmethyl-7α-benzylcarbamoyl-6,14-endoethanotetrahydronorthebaine, N-cyclopropylmethyl-7β-benzylcarbamoyl-6,14-endoethanotetrahydronorthebaine, N-cyclopropylmethyl-7α-phenethylcarbamoyl-6,14-endoethenotetrahydronormorphide, N-cyclopropylmethyl-7β-phenethylcarbamoyl-6,14-endoethenotetrahydronormorphide, N-cyclopropylmethyl-7α-phenethylcarbamoyl- 6,14-endoethanotetrahydronormorphide, N-cyclopropylmethyl-7β-phenethylcarbamoyl-6,14-endoethanotetrahydronormorphide, N-cyclopropylmethyl-7α-phenethylcarbamoyl-6,14-endoethenotetrahydronorcodide, N-cyclopropylmethyl-7β-phenethylcarbamoyl-6,14-endoethenotetrahydronorcodide, N-cyclopropylmethyl-7α-phenethylcarbamoyl-6,14-endoethanotetrahydronorcodide, N-cyclopropylmethyl-7β-phenethylcarbamoyl-6,14-endoethanotetrahydronorcodide, N-cyclopropylmethyl-7α-phenethylcarbamoyl-6,14-endoethenotetrahydronororipavine, N-cyclopropylmethyl-7β-phenethylcarbamoyl-6,14-endoethenotetrahydronororipavine, N-cyclopropylmethyl-7α-phenethylcarbamoyl-6,14-endoethanotetrahydronororipavine, N-cyclopropylmethyl-7β-phenethylcarbamoyl-6,14-endoethanotetrahydronororipavine, N-cyclopropylmethyl-7α-phenethylcarbamoyl-6,14-endoethenotetrahydronorthebaine, N-cyclopropylmethyl-7β-phenethylcarbamoyl-6,14-endoethenotetrahydronorthebaine, N-cyclopropylmethyl-7α-phenethylcarbamoyl 6,14-endoethanotetrahydronorthebaine, N-cyclopropylmethyl-7β-phenethylcarbamoyl-6,14-endoethanotetrahydronorthebaine, N-cyclopropylmethyl-7α-phenethylcarbamoyl-8β-methyl-6,14-endoethenotetrahydronormorphide, N-cyclopropylmethyl-7β-phenethylcarbamoyl-8β-methyl-6,14-endoethenotetrahydronormorphide, N-cyclopropylmethyl-7α-phenethylcarbamoyl-8β-methyl-6,14-endoethanotetrahydronormorphide, N-cyclopropylmethyl-7β-phenethylcarbamoyl-8α-methyl- 6,14-endoethanotetrahydronormorphide, N-cyclopropylmethyl-7α-phenethylcarbamoyl-8β-methyl-6,14-endoethenotetrahydronorcodide, N-cyclopropylmethyl-7β-phenethylcarbamoyl-8α-methyl-6,14-endoethenotetrahydronorcodide, N-cyclopropylmethyl-7α-phenethylcarbamoyl-8β-methyl-6,14-endoethanotetrahydronorcodide, N-cyclopropylmethyl-7β-phenethylcarbamoyl-8α-methyl-6,14-endoethanotetrahydronorcodide, N-cyclopropylmethyl-7α-phenethylcarbamoyl-8β-methyl-6,14-endoethenotetrahydronororipavine, N-cyclopropylmethyl-7β-phenethylcarbamoyl-8α-methyl-6,14-endoethenotetrahydronororipavine, N-cyclopropylmethyl-7α-phenethylcarbamoyl-8β-methyl-6,14-endoethanotetrahydronororipavine, N-cyclopropylmethyl-7β-phenethylcarbamoyl-8α-methyl-6,14-endoethanotetrahydronororipavine, N-cyclopropylmethyl-7α-phenethylcarbamoyl-8β-methyl-6,14-endoethenotetrahydronorthebaine, N-cyclopropylmethyl-7β-phenethylcarbamoyl-8α-methyl-6,14-endoethenotetrahydronorthebaine, N-cyclopropylmethyl-7α-phenethylcarbamoyl-8β-methyl-6,14-endoethanotetrahydronorthebaine, N-cyclopropylmethyl-7β-phenethylcarbamoyl-8α-methyl-6,14-endoethanotetrahydronorthebaine, N-cyclopropylmethyl-7β-methyl-7α-phenethylcarbamoyl-6,14-endoethenotetrahydronormorphide, N-cyclopropylmethyl-7α-methyl-7β-phenethylcarbamoyl-6,14-endoethenotetrahydronormorphide, N-cyclopropylmethyl-7β-methyl-7α-phenethylcarbamoyl-6,14-endoethanotetrahydronormorphide, N-cyclopropylmethyl-7α-methyl-7β-phenethylcarbamoyl-6,14-endoethanotetrahydronormorphide, N-cyclopropylmethyl-7β-methyl-7α-phenethylcarbamoyl-6,14-endoethenotetrahydronorcodide, N-cyclopropylmethyl-7α-methyl-7β-phenethylcarbamoyl-6,14-endoethenotetrahydronorcodide, N-cyclopropylmethyl-7β-methyl-7α-phenethylcarbamoyl-6,14-endoethanotetrahydronorcodide, N-cyclopropylmethyl-7α-methyl-7β-phenethylcarbamoyl-6,14-endoethanotetrahydronorcodide, N-cyclopropylmethyl-7β-methyl-7α-phenethylcarbamoyl-6,14-endoethenotetrahydronororipavine, N-cyclopropylmethyl-7α-methyl-7β-phenethylcarbamoyl-6,14-endoethenotetrahydronororipavine, N-cyclopropylmethyl-7β-methyl-7α-phenethylcarbamoyl-6,14-endoethanotetrahydronororipavine, N-cyclopropylmethyl-7α-methyl-7β-phenethylcarbamoyl-6,14-endoethanotetrahydronororipavine, N-cyclopropylmethyl-7β-methyl-7α-phenethylcarbamoyl-6,14-endoethenotetrahydronorthebaine, N-cyclopropylmethyl-7α-methyl-7β-phenethylcarbamoyl-6,14-endoethenotetrahydronorthebaine, N-cyclopropylmethyl-7β-methyl-7α-phenethylcarbamoyl- 6,14-endoethanotetrahydronorthebaine, N-cyclopropylmethyl-7α-methyl-7β-phenethylcarbamoyl-6,14-endoethanotetrahydronorthebaine, N-cyclopropylmethyl-7α-(4-methoxyphenethylcarbamoyl)-6,14-endoethenotetrahydronormorphide, N-cyclopropylmethyl-7β-(4-methoxyphenethylcarbamoyl)-6,14-endoethenotetrahydronormorphide, N-cyclopropylmethyl-7α-(4-methoxyphenethylcarbamoyl)-6,14-endoethanotetrahydronormorphide, N-cyclopropylmethyl-7β-(4-methoxyphenethylcarbamoyl)-6,14-endoethanotetrahydronormorphide, N-cyclopropylmethyl-7α-(4-methoxyphenethylcarbamoyl)-6,14-endoethenotetrahydronorcodide, N-cyclopropylmethyl-7β-(4-methoxyphenethylcarbamoyl)-6,14-endoethenotetrahydronorcodide, N-cyclopropylmethyl-7α-(4-methoxyphenethylcarbamoyl)-6,14-endoethanotetrahydronorcodide, N-cyclopropylmethyl-7β-(4-methoxyphenethylcarbamoyl)-6,14-endoethanotetrahydronorcodide, N-cyclopropylmethyl-7α-(4-methoxyphenethylcarbamoyl)-6,14-endoethenotetrahydronororipavine, N-cyclopropylmethyl-7β-(4-methoxyphenethylcarbamoyl)-6,14-endoethenotetrahydronororipavine, N-cyclopropylmethyl-7α-(4-methoxyphenethylcarbamoyl)-6,14-endoethanotetrahydronororipavine, N-cyclopropylmethyl-7β-(4-methoxyphenethylcarbamoyl)-6,14-endoethanotetrahydronororipavine, N-cyclopropylmethyl-7α-(4-methoxyphenethylcarbamoyl)-6,14-endoethenotetrahydronorthebaine, N-cyclopropylmethyl-7β-(4-methoxyphenethylcarbamoyl)-6,14- endoethenotetrahydronorthebaine, N-cyclopropylmethyl-7α-(4-methoxyphenethylcarbamoyl)-6,14-endoethanotetrahydronorthebaine, N-cyclopropylmethyl-7β-(4-methoxyphenethylcarbamoyl)-6,14-endoethanotetrahydronorthebaine, N-cyclopropylmethyl-7α-(4-methoxyphenethylcarbamoyl)-8β-methyl-6,14-endoethenotetrahydronormorphide, N-cyclopropylmethyl-7β-(4-methoxyphenethylcarbamoyl)-8α-methyl-6,14-endoethenotetrahydronormorphide, N-cyclopropylmethyl-7α-(4-methoxyphenethylcarbamoyl)-8β-methyl-6,14-endoethanotetrahydronormorphide, N-cyclopropylmethyl-7β-(4-methoxyphenethylcarbamoyl)-8α-methyl-6,14-endoethanotetrahydronormorphide, N-cyclopropylmethyl-7α-(4-methoxyphenethylcarbamoyl)-8β-methyl-6,14-endoethenotetrahydronorcodide, N-cyclopropylmethyl-7β-(4-methoxyphenethylcarbamoyl)-8α-methyl-6,14-endoethenotetrahydronorcodide, N-cyclopropylmethyl-7α-(4-methoxyphenethylcarbamoyl)-8β-methyl-6,14-endoethenotetrahydronorcodide, N-cyclopropylmethyl-7β-(4-methoxyphenethylcarbamoyl)-8α-methyl-6,14-endoethanotetrahydronorcodide, N-cyclopropylmethyl-7α-(4-methoxyphenethylcarbamoyl)-8β-methyl-6,14-endoethenotetrahydronororipavine, N-cyclopropylmethyl-7β-(4-methoxyphenethylcarbamoyl)-8α-methyl-6,14-endoethenotetrahydronororipavine, N-cyclopropylmethyl-7α-(4-methoxyphenethylcarbamoyl)-8β-methyl-6,14-endoethanotetrahydronororipavine, N-cyclopropylmethyl-7β-(4-methoxyphenethylcarbamoyl)-8α-methyl-6,14-endoethanotetrahydronororipavine, N-cyclopropylmethyl-7α-(4-methoxyphenethylcarbamoyl)-8β-methyl-6,14-endoethenotetrahydronorthebaine, N-cyclopropylmethyl-7β-(4-methoxyphenethylcarbamoyl)-8α-methyl-6,14-endoethenotetrahydronorthebaine, N-cyclopropylmethyl-7α-(4-methoxyphenethylcarbamoyl)-8β-methyl-6,14-endoethanotetrahydronorthebaine, N-cyclopropylmethyl-7β-(4-methoxyphenethylcarbamoyl)-8α-methyl-6,14-endoethanotetrahydronorthebaine, N-cyclopropylmethyl-7β-methyl-7α-(4-methoxyphenethylcarbamoyl)-6,14-endoethenotetrahydronormorphide, N-cyclopropylmethyl-7α-methyl-7β-(4-methoxyphenethylcarbamoyl)-6,14-endoethenotetrahydronormorphide, N-cyclopropylmethyl-7β-methyl-7α-(4-methoxyphenethylcarbamoyl)-6,14-endoethanotetrahydronormorphide, N-cyclopropylmethyl-7α-methyl-7β-(4-methoxyphenethylcarbamoyl)-6,14-endoethanotetrahydronormorphide, N-cyclopropylmethyl-7β-methyl-7α-(4-methoxyphenethylcarbamoyl)-6,14-endoethenotetrahydronorcodide, N-cyclopropylmethyl-7α-methyl-7β-(4-methoxyphenethylcarbamoyl)-6,14-endoethenotetrahydronorcodide, N-cyclopropylmethyl-7β-methyl-7α-(4-methoxyphenethylcarbamoyl)-6,14-endoethanotetrahydronorcodide, N-cyclopropylmethyl-7α-methyl-7β-(4-methoxyphenethylcarbamoyl)-6,14-endoethanotetrahydronorcodide, N-cyclopropylmethyl-7β-methyl-7α-(4-methoxyphenethylcarbamoyl)-6,14-endoethenotetrahydronororipavine, N-cyclopropylmethyl-7α-methyl-7β-(4-methoxyphenethylcarbamoyl)-6,14-endoethenotetrahydronororipavine, N-cyclopropylmethyl-7β-methyl-7α-(4-methoxyphenethylcarbamoyl)-6,14-endoethanotetrahydronororipavine, N-cyclopropylmethyl-7α-methyl-7β-(4-methoxyphenethylcarbamoyl)-6,14-endoethanotetrahydronororipavine, N-cyclopropylmethyl-7β-methyl-7α-(4-methoxyphenethylcarbamoyl)-6,14-endoethenotetrahydronorthebaine, N-cyclopropylmethyl-7α-methyl-7β-(4-methoxyphenethylcarbamoyl)-6,14-endoethenotetrahydronorthebaine, N-cyclopropylmethyl-7β-methyl-7α-(4-methoxyphenethylcarbamoyl)-6,14-endoethanotetrahydronorthebaine, N-cyclopropylmethyl-7α-methyl-7β-(4-methoxyphenethylcarbamoyl)-6,14-endoethanotetrahydronorthebaine, N-cyclopropylmethyl-7α-(4-bromophenethylcarbamoyl)-6,14-endoethenotetrahydronormorphide, N-cyclopropylmethyl-7β-(4-bromophenethylcarbamoyl)-6,14-endoethenotetrahydronormorphide, N-cyclopropylmethyl-7α-(4-bromophenethylcarbamoyl)-6,14-endoethanotetrahydronormorphide, N-cyclopropylmethyl-7β-(4-bromophenethylcarbamoyl)-6,14-endoethanotetrahydronormorphide, N-cyclopropylmethyl-7α-(4-bromophenethylcarbamoyl)-6,14-endoethenotetrahydronorcodide, N-cyclopropylmethyl-7β-(4-bromophenethylcarbamoyl)-6,14-endoethenotetrahydronorcodide, N-cyclopropylmethyl-7α-(4-bromophenethylcarbamoyl)-6,14-endoethanotetrahydronorcodide, N-cyclopropylmethyl-7β-(4-bromophenethylcarbamoyl)-6,14-endoethanotetrahydronorcodide, N-cyclopropylmethyl-7α-(4-bromophenethylcarbamoyl)-6,14-endoethenotetrahydronororipavine, N-cyclopropylmethyl-7β-(4-bromophenethylcarbamoyl)-6,14-endoethenotetrahydronororipavine, N-cyclopropylmethyl-7α-(4-bromophenethylcarbamoyl)-6,14-endoethanotetrahydronororipavine, N-cyclopropylmethyl-7β-(4-bromophenethylcarbamoyl)-6,14-endoethanotetrahydronororipavine, N-cyclopropylmethyl-7α-(4-bromophenethylcarbamoyl)-6,14-endoethenotetrahydronorthebaine, N-cyclopropylmethyl-7β-(4-bromophenethylcarbamoyl)-6,14-endoethenotetrahydronorthebaine, N-cyclopropylmethyl-7α-(4-bromophenethylcarbamoyl)-6,14-endoethanotetrahydronorthebaine, N-cyclopropylmethyl-7β-(4-bromophenethylcarbamoyl)-6,14-endoethanotetrahydronorthebaine, N-cyclopropylmethyl-7α-(4-bromophenethylcarbamoyl)-8β-methyl-6,14-endoethenotetrahydronormorphide, N-cyclopropylmethyl-7β-(4-bromophenethylcarbamoyl)-8α-methyl-6,14-endoethenotetrahydronormorphide, N-cyclopropylmethyl-7α-(4-bromophenethylcarbamoyl)-8β-methyl-6,14-endoethanotetrahydronormorphide, N-cyclopropylmethyl-7β-(4-bromophenethylcarbamoyl)-8α-methyl-6,14-endoethanotetrahydronormorphide, N-cyclopropylmethyl-7α-(4-bromophenethylcarbamoyl)-8β-methyl-6,14-endoethenotetrahydronorcodide, N-cyclopropylmethyl-7β-(4-bromophenethylcarbamoyl)-8α-methyl-6,14-endoethenotetrahydronorcodide, N-cyclopropylmethyl-7α-(4-bromophenethylcarbamoyl)-8β-methyl-6,14-endoethanotetrahydronorcodide, N-cyclopropylmethyl-7β-(4-bromophenethylcarbamoyl)-8α-methyl-6,14-endoethanotetrahydronorcodide, N-cyclopropylmethyl-7α-(4-bromophenethylcarbamoyl)-8β-methyl-6,14-endoethenotetrahydronororipavine, N-cyclopropylmethyl-7β-(4-bromophenethylcarbamoyl)-8α-methyl-6,14-endoethenotetrahydronororipavine, N-cyclopropylmethyl-7α-(4-bromophenethylcarbamoyl)-8β-methyl-6,14-endoethanotetrahydronororipavine, N-cyclopropylmethyl-7β-(4-bromophenethylcarbamoyl)-8α-methyl-6,14-endoethanotetrahydronororipavine, N-cyclopropylmethyl-7α-(4-bromophenethylcarbamoyl)-8β-methyl-6,14-endoethenotetrahydronorthebaine, N-cyclopropylmethyl-7β-(4-bromophenethylcarbamoyl)-8α-methyl-6,14-endoethenotetrahydronorthebaine, N-cyclopropylmethyl-7α-(4-bromophenethylcarbamoyl)-8β-methyl-6,14-endoethanotetrahydronorthebaine, N-cyclopropylmethyl-7β-(4-bromophenethylcarbamoyl)-8α-methyl-6,14-endoethanotetrahydronorthebaine, N-cyclopropylmethyl-7β-methyl-7α-(4-bromophenethylcarbamoyl)-6,14- endoethenotetrahydronormorphide, N-cyclopropylmethyl-7α-methyl-7β-(4-bromophenethylcarbamoyl)-6,14-endoethenotetrahydronormorphide, N-cyclopropylmethyl-7β-methyl-7α-(4-bromophenethylcarbamoyl)-6,14-endoethanotetrahydronormorphide, N-cyclopropylmethyl-7α-methyl-7β-(4-bromophenethylcarbamoyl)-6,14-endoethanotetrahydronormorphide, N-cyclopropylmethyl-7β-methyl-7α-(4-bromophenethylcarbamoyl)-6,14-endoethenotetrahydronorcodide, N-cyclopropylmethyl-7α-methyl-7β-(4-bromophenethylcarbamoyl)-6,14-endoethenotetrahydronorcodide, N-cyclopropylmethyl-7β-methyl-7α-(4-bromophenethylcarbamoyl)-6,14-endoethanotetrahydronorcodide, N-cyclopropylmethyl-7α-methyl-7β-(4-bromophenethylcarbamoyl)-6,14-endoethanotetrahydronorcodide, N-cyclopropylmethyl-7β-methyl-7α-(4-bromophenethylcarbamoyl)-6,14-endoethenotetrahydronororipavine, N-cyclopropylmethyl-7α-methyl-7β-(4-bromophenethylcarbamoyl)-6,14-endoethenotetrahydronororipavine, N-cyclopropylmethyl-7β-methyl-7α-(4-bromophenethylcarbamoyl)- 6,14-endoethanotetrahydronororipavine, N-cyclopropylmethyl-7α-methyl-7β-(4-bromophenethylcarbamoyl)-6,14-endoethanotetrahydronororipavine, N-cyclopropylmethyl-7β-methyl-7α-(4-bromophenethylcarbamoyl)-6,14-endoethenotetrahydronorthebaine, N-cyclopropylmethyl-7α-methyl-7β-(4-bromophenethylcarbamoyl)-6,14-endoethenotetrahydronorthebaine, N-cyclopropylmethyl-7β-methyl-7α-(4-bromophenethylcarbamoyl)-6,14-endoethanotetrahydronorthebaine, N-cyclopropylmethyl-7α-methyl-7β-(4-bromophenethylcarbamoyl)-6,14-endoethanotetrahydronorthebaine, N-cyclopropylmethyl-7α-(N-methylphenethylcarbamoyl)-6,14-endoethenotetrahydronormorphide, N-cyclopropylmethyl-7β-(N-methylphenethylcarbamoyl)-6,14-endoethenotetrahydronormorphide, N-cyclopropylmethyl-7α-(N-methylphenethylcarbamoyl)-6,14-endoethanotetrahydronormorphide, N-cyclopropylmethyl-7β-(N-methylphenethylcarbamoyl)-6,14-endoethanotetrahydronormorphide, N-cyclopropylmethyl-7α-(N-methylphenethylcarbamoyl)-6,14-endoethenotetrahydronorcodide, N-cyclopropylmethyl-7β-(N-methylphenethylcarbamoyl)-6,14-endoethenotetrahydronorcodide, N-cyclopropylmethyl-7α-(N-methylphenethylcarbamoyl)-6,14-endoethanotetrahydronorcodide, N-cyclopropylmethyl-7β-(N-methylphenethylcarbamoyl)- 6,14-endoethanotetrahydronorcodide, N-cyclopropylmethyl-7α-(N-methylphenethylcarbamoyl)-6,14-endoethenotetrahydronororipavine, N-cyclopropylmethyl-7β-(N-methylphenethylcarbamoyl)-6,14-endoethenotetrahydronororipavine, N-cyclopropylmethyl-7α-(N-methylphenethylcarbamoyl)-6,14-endoethanotetrahydronororipavine, N-cyclopropylmethyl-7β-(N-methylphenethylcarbamoyl)-6,14-endoethanotetrahydronororipavine, N-cyclopropylmethyl-7α-(N-methylphenethylcarbamoyl)-6,14-endoethenotetrahydronorthebaine, N-cyclopropylmethyl-7β-(N-methylphenethylcarbamoyl)-6,14-endoethenotetrahydronorthebaine, N-cyclopropylmethyl-7α-(N-methylphenethylcarbamoyl)-6,14-endoethanotetrahydronorthebaine, N-cyclopropylmethyl-7β-(N-methylphenethylcarbamoyl)-6,14-endoethanotetrahydronorthebaine, N-cyclopropylmethyl-7α-(N-methylphenethylcarbamoyl)-8β-methyl-6,14-endoethenotetrahydronormorphide, N-cyclopropylmethyl-7β-(N-methylphenethylcarbamoyl)-8α-methyl-6,14-endoethenotetrahydronormorphide, N-cyclopropylmethyl-7α-(N-methylphenethylcarbamoyl)-8β-methyl-6,14-endoethanotetrahydronormorphide, N-cyclopropylmethyl-7β-(N-methylphenethylcarbamoyl)-8α-methyl-6,14-endoethanotetrahydronormorphide, N-cyclopropylmethyl-7α-(N-methylphenethylcarbamoyl)-8β-methyl-6,14-endoethenotetrahydronorcodide, N-cyclopropylmethyl- 7β-(N-methylphenethylcarbamoyl)-8α-methyl-6,14-endoethenotetrahydronorcodide, N-cyclopropylmethyl-7α-(N-methylphenethylcarbamoyl)-8β-methyl-6,14-endoethanotetrahydronorcodide, N-cyclopropylmethyl-7β-(N-methylphenethylcarbamoyl)-8α-methyl-6,14-endoethanotetrahydronorcodide, N-cyclopropylmethyl-7α-(N-methylphenethylcarbamoyl)-8β-methyl-6,14-endoethenotetrahydronororipavine, N-cyclopropylmethyl-7β-(N-methylphenethylcarbamoyl)-8α-methyl-6,14-endoethenotetrahydronororipavine, N-cyclopropylmethyl-7α-(N-methylphenethylcarbamoyl)-8β-methyl-6,14-endoethanotetrahydronororipavine, N-cyclopropylmethyl-7β-(N-methylphenethylcarbamoyl)-8α-methyl-6,14-endoethanotetrahydronororipavine, N-cyclopropylmethyl-7α-(N-methylphenethylcarbamoyl)-8β-methyl-6,14-endoethenotetrahydronorthebaine, N-cyclopropylmethyl-7β-(N-methylphenethylcarbamoyl)-8α-methyl-6,14-endoethenotetrahydronorthebaine, N-cyclopropylmethyl-7α-(N-methylphenethylcarbamoyl)-8β-methyl-6,14-endoethanotetrahydronorthebaine, N-cyclopropylmethyl-7β-(N-methylphenethylcarbamoyl)-8α-methyl-6,14-endoethanotetrahydronorthebaine, N-cyclopropylmethyl-7β-methyl-7α-(N-methylphenethylcarbamoyl)-6,14-endoethenotetrahydronormorphide, N-cyclopropylmethyl-7α-methyl-7β-(N-methylphenethylcarbamoyl)-6,14-endoethenotetrahydronormorphide, N-cyclopropylmethyl-7β-methyl-7α-(N-methylphenethylcarbamoyl)-6,14-endoethanotetrahydronormorphide, N-cyclopropylmethyl-7α-methyl-7β-(N-methylphenethylcarbamoyl)-6,14-endoethanotetrahydronormorphide, N-cyclopropylmethyl-7β-methyl-7α-(N-methylphenethylcarbamoyl)-6,14-endoethenotetrahydronorcodide, N-cyclopropylmethyl-7α-methyl-7β-(N-methylphenethylcarbamoyl)-6,14-endoethenotetrahydronorcodide, N-cyclopropylmethyl-7β-methyl-7α-(N-methylphenethylcarbamoyl)-6,14-endoethanotetrahydronorcodide, N-cyclopropylmethyl-7α-methyl-7β-(N-methylphenethylcarbamoyl)-6,14-endoethanotetrahydronorcodide, N-cyclopropylmethyl-7β-methyl-7α-(N-methylphenethylcarbamoyl)-6,14-endoethenotetrahydronororipavine, N-cyclopropylmethyl-7α-methyl-7β-(N-methylphenethylcarbamoyl)-6,14-endoethenotetrahydronororipavine, N-cyclopropylmethyl-7β-methyl-7α-(N-methylphenethylcarbamoyl)-6,14-endoethanotetrahydronororipavine, N-cyclopropylmethyl-7α-methyl-7β-(N-methylphenethylcarbamoyl)-6,14-endoethanotetrahydronororipavine, N-cyclopropylmethyl-7β-methyl-7α-(N-methylphenethylcarbamoyl)-6,14-endoethenotetrahydronorthebaine, N-cyclopropylmethyl-7α-methyl-7β-(N-methylphenethylcarbamoyl)-6,14-endoethenotetrahydronorthebaine, N-cyclopropylmethyl-7β-methyl-7α-(N-methylphenethylcarbamoyl)- 6,14-endoethanotetrahydronorthebaine, N-cyclopropylmethyl-7α-methyl-7β-(N-methylphenethylcarbamoyl)-6,14-endoethanotetrahydronorthebaine, N-cyclopropylmethyl-7α-(N-methyl-4-methoxyphenethylcarbamoyl)-6,14-endoethenotetrahydronormorphide, N-cyclopropylmethyl-7β-(N-methyl-4-methoxyphenethylcarbamoyl)-6,14-endoethenotetrahydronormorphide, N-cyclopropylmethyl-7α-(N-methyl-4-methoxyphenethylcarbamoyl)-6,14-endoethanotetrahydronormorphide, N-cyclopropylmethyl-7β-(N-methyl-4-methoxyphenethylcarbamoyl)-6,14- endoethanotetrahydronormorphide, N-cyclopropylmethyl-7α-(N-methyl-4-methoxyphenethylcarbamoyl)-6,14-endoethenotetrahydronorcodide, N-cyclopropylmethyl-7β-(N-methyl-4-methoxyphenethylcarbamoyl)-6,14-endoethenotetrahydronorcodide, N-cyclopropylmethyl-7α-(N-methyl-4-methoxyphenethylcarbamoyl)-6,14-endoethanotetrahydronorcodide, N-cyclopropylmethyl-7β-(N-methyl-4-methoxyphenethylcarbamoyl)-6,14-endoethanotetrahydronorcodide, N-cyclopropylmethyl-7α-(N-methyl-4-methoxyphenethylcarbamoyl)-6,14-endoethenotetrahydronororipavine, N-cyclopropylmethyl-7β-(N-methyl-4-methoxyphenethylcarbamoyl)-6,14-endoethenotetrahydronororipavine, N-cyclopropylmethyl-7α-(N-methyl-4-methoxyphenethylcarbamoyl)-6,14-endoethanotetrahydronororipavine, N-cyclopropylmethyl-7β-(N-methyl-4-methoxyphenethylcarbamoyl)- 6,14-endoethanotetrahydronororipavine, N-cyclopropylmethyl-7α-(N-methyl-4-methoxyphenethylcarbamoyl)-6,14-endoethenotetrahydronorthebaine, N-cyclopropylmethyl-7β-(N-methyl-4-methoxyphenethylcarbamoyl)-6,14-endoethenotetrahydronorthebaine, N-cyclopropylmethyl-7α-(N-methyl-4-methoxyphenethylcarbamoyl)-6,14-endoethanotetrahydronorthebaine, N-cyclopropylmethyl-7β-(N-methyl-4-methoxyphenethylcarbamoyl)-6,14-endoethanotetrahydronorthebaine, N-cyclopropylmethyl-7α-(N-methyl-4-methoxyphenethylcarbamoyl)-8β-methyl-6,14-endoethenotetrahydronormorphide, N-cyclopropylmethyl-7β-(N-methyl-4-methoxyphenethylcarbamoyl)-8α-methyl-6,14-endoethenotetrahydronormorphide, N-cyclopropylmethyl-7α-(N-methyl-4-methoxyphenethylcarbamoyl)-8β-methyl-6,14-endoethanotetrahydronormorphide, N-cyclopropylmethyl-7β-(N-methyl-4-methoxyphenethylcarbamoyl)-8α-methyl-6,14-endoethanotetrahydronormorphide, N-cyclopropylmethyl-7α-(N-methyl-4-methoxyphenethylcarbamoyl)-8β-methyl-6,14-endoethenotetrahydronorcodide, N-cyclopropylmethyl-7β-(N-methyl-4-methoxyphenethylcarbamoyl)-8α-methyl-6,14-endoethenotetrahydronorcodide, N-cyclopropylmethyl-7α-(N-methyl-4-methoxyphenethylcarbamoyl)-8β-methyl-6,14-endoethanotetrahydronorcodide, N-cyclopropylmethyl-7β-(N-methyl-4-methoxyphenethylcarbamoyl)-8α-methyl-6,14-endoethanotetrahydronorcodide, N-cyclopropylmethyl-7α-(N-methyl-4-methoxyphenethylcarbamoyl)-8β-methyl-6,14-endoethenotetrahydronororipavine, N-cyclopropylmethyl-7β-(N-methyl-4-methoxyphenethylcarbamoyl)-8α-methyl-6,14-endoethenotetrahydronororipavine, N-cyclopropylmethyl-7α-(N-methyl-4-methoxyphenethylcarbamoyl)-8β-methyl-6,14-endoethanotetrahydronororipavine, N-cyclopropylmethyl-7β-(N-methyl-4-methoxyphenethylcarbamoyl)-8α-methyl-6,14-endoethanotetrahydronororipavine, N-cyclopropylmethyl-7α-(N-methyl-4-methoxyphenethylcarbamoyl)-8β-methyl-6,14-endoethenotetrahydronorthebaine, N-cyclopropylmethyl-7β-(N-methyl-4-methoxyphenethylcarbamoyl)-8α-methyl-6,14-endoethenotetrahydronorthebaine, N-cyclopropylmethyl-7α-(N-methyl-4-methoxyphenethylcarbamoyl)-8β-methyl-6,14-endoethanotetrahydronorthebaine, N-cyclopropylmethyl-7β-(N-methyl-4-methoxyphenethylcarbamoyl)-8α-methyl-6,14-endoethanotetrahydronorthebaine, N-cyclopropylmethyl-7β-methyl-7α-(N-methyl-4-methoxyphenethylcarbamoyl)-6,14-endoethenotetrahydronormorphide, N-cyclopropylmethyl-7α-methyl-7β-(N-methyl-4-methoxyphenethylcarbamoyl)-6,14-endoethenotetrahydronormorphide, N-cyclopropylmethyl-7β-methyl-7α-(N-methyl-4-methoxyphenethylcarbamoyl)-6,14-endoethanotetrahydronormorphide, N-cyclopropylmethyl-7α-methyl-7β-(N-methyl-4-methoxyphenethylcarbamoyl)-6,14-endoethanotetrahydronormorphide, N-cyclopropylmethyl-7β-methyl-7α-(N-methyl-4-methoxyphenethylcarbamoyl)-6,14-endoethenotetrahydronorcodide, N-cyclopropylmethyl-7α-methyl-7β-(N-methyl-4-methoxyphenethylcarbamoyl)-6,14-endoethenotetrahydronorcodide, N-cyclopropylmethyl-7β-methyl-7α-(N-methyl-4-methoxyphenethylcarbamoyl)-6,14-endoethanotetrahydronorcodide, N-cyclopropylmethyl-7α-methyl-7β-(N-methyl-4-methoxyphenethylcarbamoyl)-6,14-endoethanotetrahydronorcodide, N-cyclopropylmethyl-7β-methyl-7α-(N-methyl-4-methoxyphenethylcarbamoyl)-6,14-endoethenotetrahydronororipavine, N-cyclopropylmethyl-7α-methyl-7β-(N-methyl-4-methoxyphenethylcarbamoyl)-6,14-endoethenotetrahydronororipavine, N-cyclopropylmethyl-7β-methyl-7α-(N-methyl-4-methoxyphenethylcarbamoyl)-6,14-endoethanotetrahydronororipavine, N-cyclopropylmethyl-7α-methyl-7β-(N-methyl-4-methoxyphenethylcarbamoyl)-6,14-endoethanotetrahydronororipavine, N-cyclopropylmethyl-7β-methyl-7α-(N-methyl-4-methoxyphenethylcarbamoyl)-6,14-endoethenotetrahydronorthebaine, N-cyclopropylmethyl-7α-methyl-7β-(N-methyl-4-methoxyphenethylcarbamoyl)-6,14-endoethenotetrahydronorthebaine, N-cyclopropylmethyl-7β-methyl-7α-(N-methyl-4-methoxyphenethylcarbamoyl)-6,14-endoethanotetrahydronorthebaine, N-cyclopropylmethyl-7α-methyl-7β-(N-methyl-4-methoxyphenethylcarbamoyl)-6,14-endoethanotetrahydronorthebaine, N-cyclopropylmethyl-7α-(N-methyl-4-bromophenethylcarbamoyl)-6,14-endoethenotetrahydronormorphide, N-cyclopropylmethyl-7β-(N-methyl-4-bromophenethylcarbamoyl)- 6,14-endoethenotetrahydronormorphide, N-cyclopropylmethyl-7α-(N-methyl-4-bromophenethylcarbamoyl)-6,14-endoethanotetrahydronormorphide, N-cyclopropylmethyl-7β-(N-methyl-4-bromophenethylcarbamoyl)-6,14-endoethanotetrahydronormorphide, N-cyclopropylmethyl-7α-(N-methyl-4-bromophenethylcarbamoyl)-6,14-endoethenotetrahydronorcodide, N-cyclopropylmethyl-7β-(N-methyl-4-bromophenethylcarbamoyl)-6,14-endoethenotetrahydronorcodide, N-cyclopropylmethyl-7α-(N-methyl-4-bromophenethylcarbamoyl)-6,14-endoethanotetrahydronorcodide, N-cyclopropylmethyl-7β-(N-methyl-4-bromophenethylcarbamoyl)-6,14-endoethanotetrahydronorcodide, N-cyclopropylmethyl-7α-(N-methyl-4-bromophenethylcarbamoyl)-6,14-endoethenotetrahydronororipavine, N-cyclopropylmethyl-7β-(N-methyl-4-bromophenethylcarbamoyl)-6,14-endoethenotetrahydronororipavine, N-cyclopropylmethyl-7α-(N-methyl-4-bromophenethylcarbamoyl)-6,14-endoethanotetrahydronororipavine, N-cyclopropylmethyl-7β-(N-methyl-4-bromophenethylcarbamoyl)-6,14-endoethanotetrahydronororipavine, N-cyclopropylmethyl-7α-(N-methyl-4-bromophenethylcarbamoyl)-6,14-endoethenotetrahydronorthebaine, N-cyclopropylmethyl-7β-(N-methyl-4-bromophenethylcarbamoyl)-6,14-endoethenotetrahydronorthebaine, N-cyclopropylmethyl-7α-(N-methyl-4-bromophenethylcarbamoyl)-6,14-endoethanotetrahydronorthebaine, N-cyclopropylmethyl- 7β-(N-methyl-4-bromophenethylcarbamoyl)-6,14-endoethanotetrahydronorthebaine, N-cyclopropylmethyl-7α-(N-methyl-4-bromophenethylcarbamoyl)-8β-methyl-6,14-endoethenotetrahydronormorphide, N-cyclopropylmethyl-7β-(N-methyl-4-bromophenethylcarbamoyl)-8α-methyl-6,14-endoethenotetrahydronormorphide, N-cyclopropylmethyl-7α-(N-methyl-4-bromophenethylcarbamoyl)-8β-methyl-6,14-endoethanotetrahydronormorphide, N-cyclopropylmethyl-7β-(N-methyl-4-bromophenethylcarbamoyl)-8α-methyl-6,14-endoethanotetrahydronormorphide, N-cyclopropylmethyl-7α-(N-methyl-4-bromophenethylcarbamoyl)-8β-methyl-6,14-endoethenotetrahydronorcodide, N-cyclopropylmethyl-7β-(N-methyl-4-bromophenethylcarbamoyl)-8α-methyl-6,14-endoethenotetrahydronorcodide, N-cyclopropylmethyl-7α-(N-methyl-4-bromophenethylcarbamoyl)-8β-methyl-6,14-endoethanotetrahydronorcodide, N-cyclopropylmethyl-7β-(N-methyl-4-bromophenethylcarbamoyl)-8α-methyl-6,14-endoethanotetrahydronorcodide, N-cyclopropylmethyl-7α-(N-methyl-4-bromophenethylcarbamoyl)-8β-methyl-6,14-endoethenotetrahydronororipavine, N-cyclopropylmethyl-7β-(N-methyl-4-bromophenethylcarbamoyl)-8α-methyl-6,14-endoethenotetrahydronororipavine, N-cyclopropylmethyl-7α-(N-methyl-4-bromophenethylcarbamoyl)-8β-methyl-6,14-endoethanotetrahydronororipavine, N-cyclopropylmethyl-7β-(N-methyl-4-bromophenethylcarbamoyl)-8α-methyl-6,14-endoethanotetrahydronororipavine, N-cyclopropylmethyl-7α-(N-methyl-4-bromophenethylcarbamoyl)-8β-methyl-6,14-endoethenotetrahydronorthebaine, N-cyclopropylmethyl-7β-(N-methyl-4-bromophenethylcarbamoyl)-8α-methyl-6,14-endoethenotetrahydronorthebaine, N-cyclopropylmethyl-7α-(N-methyl-4-bromophenethylcarbamoyl)-8β-methyl-6,14-endoethanotetrahydronorthebaine, N-cyclopropylmethyl-7β-(N-methyl-4-bromophenethylcarbamoyl)-8α-methyl-6,14-endoethanotetrahydronorthebaine, N-cyclopropylmethyl-7β-methyl-7α-(N-methyl-4-bromophenethylcarbamoyl)-6,14-endoethenotetrahydronormorphide, N-cyclopropylmethyl-7α-methyl-7β-(N-methyl-4-bromophenethylcarbamoyl)-6,14-endoethenotetrahydronormorphide, N-cyclopropylmethyl-7β-methyl-7α-(N-methyl-4-bromophenethylcarbamoyl)-6,14-endoethanotetrahydronormorphide, N-cyclopropylmethyl-7α-methyl-7β-(N-methyl-4-bromophenethylcarbamoyl)-6,14-endoethanotetrahydronormorphide, N-cyclopropylmethyl-7β-methyl-7α-(N-methyl-4-bromophenethylcarbamoyl)-6,14-endoethenotetrahydronorcodide, N-cyclopropylmethyl-7α-methyl-7β-(N-methyl-4-bromophenethylcarbamoyl)-6,14-endoethenotetrahydronorcodide, N-cyclopropylmethyl-7β-methyl-7α-(N-methyl-4-bromophenethylcarbamoyl)-6,14-endoethanotetrahydronorcodide, N-cyclopropylmethyl-7α-methyl-7β-(N-methyl-4-bromophenethylcarbamoyl)-6,14-endoethanotetrahydronorcodide, N-cyclopropylmethyl-7β-methyl-7α-(N-methyl-4-bromophenethylcarbamoyl)-6,14-endoethenotetrahydronororipavine, N-cyclopropylmethyl-7α-methyl-7β-(N-methyl-4-bromophenethylcarbamoyl)-6,14-endoethenotetrahydronororipavine, N-cyclopropylmethyl-7β-methyl-7α-(N-methyl-4-bromophenethylcarbamoyl)-6,14-endoethanotetrahydronororipavine, N-cyclopropylmethyl-7α-methyl-7β-(N-methyl-4-bromophenethylcarbamoyl)-6,14-endoethanotetrahydronororipavine, N-cyclopropylmethyl-7β-methyl-7α-(N-methyl-4-bromophenethylcarbamoyl)-6,14-endoethenotetrahydronorthebaine, N-cyclopropylmethyl-7α-methyl-7β-(N-methyl-4-bromophenethylcarbamoyl)-6,14-endoethenotetrahydronorthebaine, N-cyclopropylmethyl-7β-methyl-7α-(N-methyl-4-bromophenethylcarbamoyl)-6,14-endoethanotetrahydronorthebaine, N-cyclopropylmethyl-7α-methyl-7β-(N-methyl-4-bromophenethylcarbamoyl)-6,14-endoethanotetrahydronorthebaine, N-cyclopropylmethyl-7α-(N-ethylphenethylcarbamoyl)-6,14-endoethenotetrahydronormorphide, N-cyclopropylmethyl-7β-(N-ethylphenethylcarbamoyl)-6,14-endoethenotetrahydronormorphide, N-cyclopropylmethyl-7α-(N-ethylphenethylcarbamoyl)-6,14-endoethanotetrahydronormorphide, N-cyclopropylmethyl-7β-(N-ethylphenethylcarbamoyl)-6,14-endoethanotetrahydronormorphide, N-cyclopropylmethyl-7α-(N-ethylphenethylcarbamoyl)- 6,14-endoethenotetrahydronorcodide, N-cyclopropylmethyl-7β-(N-ethylphenethylcarbamoyl)-6,14-endoethenotetrahydronorcodide, N-cyclopropylmethyl-7α-(N-ethylphenethylcarbamoyl)-6,14-endoethanotetrahydronorcodide, N-cyclopropylmethyl-7β-(N-ethylphenethylcarbamoyl)-6,14-endoethanotetrahydronorcodide, N-cyclopropylmethyl-7α-(N-ethylphenethylcarbamoyl)-6,14-endoethenotetrahydronororipavine, N-cyclopropylmethyl-7β-(N-ethylphenethylcarbamoyl)-6,14-endoethenotetrahydronororipavine, N-cyclopropylmethyl-7α-(N-ethylphenethylcarbamoyl)-6,14-endoethanotetrahydronororipavine, N-cyclopropylmethyl-7β-(N-ethylphenethylcarbamoyl)-6,14-endoethanotetrahydronororipavine, N-cyclopropylmethyl-7α-(N-ethylphenethylcarbamoyl)-6,14-endoethenotetrahydronorthebaine, N-cyclopropylmethyl-7β-(N-ethylphenethylcarbamoyl)-6,14-endoethenotetrahydronorthebaine, N-cyclopropylmethyl-7α-(N-ethylphenethylcarbamoyl)-6,14-endoethanotetrahydronorthebaine, N-cyclopropylmethyl-7β-(N-ethylphenethylcarbamoyl)-6,14-endoethanotetrahydronorthebaine, N-cyclopropylmethyl-7α-(N-ethylphenethylcarbamoyl)-8β-methyl-6,14-endoethenotetrahydronormorphide, N-cyclopropylmethyl-7β-(N-ethylphenethylcarbamoyl)-8α-methyl-6,14-endoethenotetrahydronormorphide, N-cyclopropylmethyl-7α-(N-ethylphenethylcarbamoyl)-8β-methyl-6,14-endoethanotetrahydronormorphide, N-cyclopropylmethyl-7β-(N-ethylphenethylcarbamoyl)-8α-methyl-6,14-endoethanotetrahydronormorphide, N-cyclopropylmethyl-7α-(N-ethylphenethylcarbamoyl)-8β-methyl-6,14-endoethenotetrahydronorcodide, N-cyclopropylmethyl-7β-(N-ethylphenethylcarbamoyl)-8α-methyl-6,14-endoethenotetrahydronorcodide, N-cyclopropylmethyl-7α-(N-ethylphenethylcarbamoyl)-8β-methyl-6,14-endoethanotetrahydronorcodide, N-cyclopropylmethyl-7β-(N-ethylphenethylcarbamoyl)-8α-methyl-6,14-endoethanotetrahydronorcodide, N-cyclopropylmethyl-7α-(N-ethylphenethylcarbamoyl)-8β-methyl-6,14-endoethenotetrahydronororipavine, N-cyclopropylmethyl-7β-(N-ethylphenethylcarbamoyl)-8α-methyl-6,14-endoethenotetrahydronororipavine, N-cyclopropylmethyl-7α-(N-ethylphenethylcarbamoyl)-8β-methyl-6,14-endoethanotetrahydronororipavine, N-cyclopropylmethyl-7β-(N-ethylphenethylcarbamoyl)-8α-methyl-6,14-endoethanotetrahydronororipavine, N-cyclopropylmethyl- 7α-(N-ethylphenethylcarbamoyl)-8β-methyl-6,14-endoethenotetrahydronorthebaine, N-cyclopropylmethyl-7β-(N-ethylphenethylcarbamoyl)-8α-methyl-6,14-endoethenotetrahydronorthebaine, N-cyclopropylmethyl-7α-(N-ethylphenethylcarbamoyl)-8β-methyl-6,14-endoethanotetrahydronorthebaine, N-cyclopropylmethyl-7β-(N-ethylphenethylcarbamoyl)-8α-methyl-6,14-endoethanotetrahydronorthebaine, N-cyclopropylmethyl-7β-methyl-7α-(N-ethylphenethylcarbamoyl)-6,14-endoethenotetrahydronormorphide, N-cyclopropylmethyl-7α-methyl-7β-(N-ethylphenethylcarbamoyl)-6,14-endoethenotetrahydronormorphide, N-cyclopropylmethyl-7β-methyl-7α-(N-ethylphenethylcarbamoyl)-6,14-endoethanotetrahydronormorphide, N-cyclopropylmethyl-7α-methyl-7β-(N-ethylphenethylcarbamoyl)-6,14-endoethanotetrahydronormorphide, N-cyclopropylmethyl-7β-methyl-7α-(N-ethylphenethylcarbamoyl)-6,14-endoethenotetrahydronorcodide, N-cyclopropylmethyl-7α-methyl-7β-(N-ethylphenethylcarbamoyl)-6,14-endoethenotetrahydronorcodide, N-cyclopropylmethyl-7β-methyl-7α-(N-ethylphenethylcarbamoyl)-6,14-endoethanotetrahydronorcodide, N-cyclopropylmethyl-7α-methyl-7β-(N-ethylphenethylcarbamoyl)-6,14-endoethanotetrahydronorcodide, N-cyclopropylmethyl-7β-methyl-7α-(N-ethylphenethylcarbamoyl)-6,14-endoethenotetrahydronororipavine, N-cyclopropylmethyl-7α-methyl-7β-(N-ethylphenethylcarbamoyl)-6,14-endoethenotetrahydronororipavine, N-cyclopropylmethyl-7β-methyl-7α-(N-ethylphenethylcarbamoyl)-6,14-endoethanotetrahydronororipavine, N-cyclopropylmethyl-7α-methyl-7β-(N-ethylphenethylcarbamoyl)-6,14-endoethanotetrahydronororipavine, N-cyclopropylmethyl-7β-methyl-7α-(N-ethylphenethylcarbamoyl)-6,14-endoethenotetrahydronorthebaine, N-cyclopropylmethyl-7α-methyl-7β-(N-ethylphenethylcarbamoyl)-6,14-endoethenotetrahydronorthebaine, N-cyclopropylmethyl-7β-methyl-7α-(N-ethylphenethylcarbamoyl)-6,14-endoethanotetrahydronorthebaine, N-cyclopropylmethyl-7α-methyl-7β-(N-ethylphenethylcarbamoyl)-6,14-endoethanotetrahydronorthebaine, N-cyclopropylmethyl-7α-(N-ethyl-4-methoxyphenethylcarbamoyl)-6,14-endoethenotetrahydronormorphide, N-cyclopropylmethyl-7β-(N-ethyl-4-methoxyphenethylcarbamoyl)-6,14-endoethenotetrahydronormorphide, N-cyclopropylmethyl-7α-(N-ethyl-4-methoxyphenethylcarbamoyl)-6,14-endoethanotetrahydronormorphide, N-cyclopropylmethyl-7β-(N-ethyl-4-methoxyphenethylcarbamoyl)-6,14-endoethanotetrahydronormorphide, N-cyclopropylmethyl-7α-(N-ethyl-4-methoxyphenethylcarbamoyl)-6,14-endoethenotetrahydronorcodide, N-cyclopropylmethyl-7β-(N-ethyl-4-methoxyphenethylcarbamoyl)-6,14-endoethenotetrahydronorcodide, N-cyclopropylmethyl-7α-(N-ethyl-4-methoxyphenethylcarbamoyl)-6,14-endoethanotetrahydronorcodide, N-cyclopropylmethyl-7β-(N-ethyl-4-methoxyphenethylcarbamoyl)-6,14-endoethanotetrahydronorcodide, N-cyclopropylmethyl-7α-(N-ethyl-4-methoxyphenethylcarbamoyl)-6,14-endoethenotetrahydronororipavine, N-cyclopropylmethyl-7β-(N-ethyl-4-methoxyphenethylcarbamoyl)-6,14-endoethenotetrahydronororipavine, N-cyclopropylmethyl-7α-(N-ethyl-4-methoxyphenethylcarbamoyl)-6,14-endoethanotetrahydronororipavine, N-cyclopropylmethyl-7β-(N-ethyl-4-methoxyphenethylcarbamoyl)-6,14-endoethanotetrahydronororipavine, N-cyclopropylmethyl-7α-(N-ethyl-4-methoxyphenethylcarbamoyl)-6,14-endoethenotetrahydronorthebaine, N-cyclopropylmethyl-7β-(N-ethyl-4-methoxyphenethylcarbamoyl)-6,14-endoethenotetrahydronorthebaine, N-cyclopropylmethyl-7α-(N-ethyl-4-methoxyphenethylcarbamoyl)-6,14-endoethanotetrahydronorthebaine, N-cyclopropylmethyl-7β-(N-ethyl-4-methoxyphenethylcarbamoyl)-6,14-endoethanotetrahydronorthebaine, N-cyclopropylmethyl-7α-(N-ethyl-4-methoxyphenethylcarbamoyl)-8β-methyl-6,14-endoethenotetrahydronormorphide, N-cyclopropylmethyl-7β-(N-ethyl-4-methoxyphenethylcarbamoyl)-8α-methyl-6,14-endoethenotetrahydronormorphide, N-cyclopropylmethyl-7α-(N-ethyl-4-methoxyphenethylcarbamoyl)-8β-methyl-6,14-endoethanotetrahydronormorphide, N-cyclopropylmethyl-7β-(N-ethyl-4-methoxyphenethylcarbamoyl)-8α-methyl-6,14-endoethanotetrahydronormorphide, N-cyclopropylmethyl-7α-(N-ethyl-4-methoxyphenethylcarbamoyl)-8β-methyl-6,14-endoethenotetrahydronorcodide, N-cyclopropylmethyl-7β-(N-ethyl-4-methoxyphenethylcarbamoyl)-8α-methyl-6,14-endoethenotetrahydronorcodide, N-cyclopropylmethyl-7α-(N-ethyl-4-methoxyphenethylcarbamoyl)-8β-methyl-6,14-endoethanotetrahydronorcodide, N-cyclopropylmethyl-7β-(N-ethyl-4-methoxyphenethylcarbamoyl)-8α-methyl-6,14-endoethanotetrahydronorcodide, N-cyclopropylmethyl-7α-(N-ethyl-4-methoxyphenethylcarbamoyl)-8β-methyl-6,14-endoethenotetrahydronororipavine, N-cyclopropylmethyl-7β-(N-ethyl-4-methoxyphenethylcarbamoyl)-8α-methyl-6,14-endoethenotetrahydronororipavine, N-cyclopropylmethyl-7α-(N-ethyl-4-methoxyphenethylcarbamoyl)-8β-methyl-6,14-endoethanotetrahydronororipavine, N-cyclopropylmethyl-7β-(N-ethyl-4-methoxyphenethylcarbamoyl)-8α-methyl-6,14-endoethanotetrahydronororipavine, N-cyclopropylmethyl-7α-(N-ethyl-4-methoxyphenethylcarbamoyl)-8β-methyl-6,14-endoethenotetrahydronorthebaine, N-cyclopropylmethyl-7β-(N-ethyl-4-methoxyphenethylcarbamoyl)-8α-methyl-6,14-endoethenotetrahydronorthebaine, N-cyclopropylmethyl-7α-(N-ethyl-4-methoxyphenethylcarbamoyl)-8β-methyl-6,14-endoethanotetrahydronorthebaine, N-cyclopropylmethyl-7β-(N-ethyl-4-methoxyphenethylcarbamoyl)-8α-methyl-6,14-endoethanotetrahydronorthebaine, N-cyclopropylmethyl-7β-methyl-7α-(N-ethyl-4-methoxyphenethylcarbamoyl)-6,14-endoethenotetrahydronormorphide, N-cyclopropylmethyl-7α-methyl-7β-(N-ethyl-4-methoxyphenethylcarbamoyl)-6,14-endoethenotetrahydronormorphide, N-cyclopropylmethyl-7β-methyl-7α-(N-ethyl-4-methoxyphenethylcarbamoyl)-6,14-endoethanotetrahydronormorphide, N-cyclopropylmethyl-7α-methyl-7β-(N-ethyl-4-methoxyphenethylcarbamoyl)-6,14-endoethanotetrahydronormorphide, N-cyclopropylmethyl-7β-methyl-7α-(N-ethyl-4-methoxyphenethylcarbamoyl)-6,14-endoethenotetrahydronorcodide, N-cyclopropylmethyl-7α-methyl-7β-(N-ethyl-4-methoxyphenethylcarbamoyl)-6,14-endoethenotetrahydronorcodide, N-cyclopropylmethyl-7β-methyl-7α-(N-ethyl-4-methoxyphenethylcarbamoyl)-6,14-endoethanotetrahydronorcodide, N-cyclopropylmethyl-7α-methyl-7β-(N-ethyl-4-methoxyphenethylcarbamoyl)-6,14-endoethanotetrahydronorcodide, N-cyclopropylmethyl-7β-methyl-7α-(N-ethyl-4-methoxyphenethylcarbamoyl)-6,14-endoethenotetrahydronororipavine, N-cyclopropylmethyl-7α-methyl-7β-(N-ethyl-4-methoxyphenethylcarbamoyl)-6,14-endoethenotetrahydronororipavine, N-cyclopropylmethyl-7β-methyl-7α-(N-ethyl-4- methoxyphenethylcarbamoyl)-6,14-endoethanotetrahydronororipavine, N-cyclopropylmethyl-7α-methyl-7β-(N-ethyl-4-methoxyphenethylcarbamoyl)-6,14-endoethanotetrahydronororipavine, N-cyclopropylmethyl-7β-methyl-7α-(N-ethyl-4-methoxyphenethylcarbamoyl)-6,14-endoethenotetrahydronorthebaine, N-cyclopropylmethyl-7α-methyl-7β-(N-ethyl-4-methoxyphenethylcarbamoyl)-6,14-endoethenotetrahydronorthebaine, N-cyclopropylmethyl-7β-methyl-7α-(N-ethyl-4-methoxyphenethylcarbamoyl)- 6,14-endoethanotetrahydronorthebaine, N-cyclopropylmethyl-7α-methyl-7β-(N-ethyl-4-methoxyphenethylcarbamoyl)-6,14-endoethanotetrahydronorthebaine, N-cyclopropylmethyl-7α-(N-ethyl-4-bromophenethylcarbamoyl)-6,14-endoethenotetrahydronormorphide, N-cyclopropylmethyl-7β-(N-ethyl-4-bromophenethylcarbamoyl)-6,14-endoethenotetrahydronormorphide, N-cyclopropylmethyl-7α-(N-ethyl-4-bromophenethylcarbamoyl)-6,14-endoethanotetrahydronormorphide, N-cyclopropylmethyl-7β-(N-ethyl-4-bromophenethylcarbamoyl)-6,14-endoethanotetrahydronormorphide, N-cyclopropylmethyl-7α-(N-ethyl-4-bromophenethylcarbamoyl)-6,14-endoethenotetrahydronorcodide, N-cyclopropylmethyl-7β-(N-ethyl-4-bromophenethylcarbamoyl)-6,14-endoethenotetrahydronorcodide, N-cyclopropylmethyl-7α-(N-ethyl-4-bromophenethylcarbamoyl)-6,14-endoethanotetrahydronorcodide, N-cyclopropylmethyl-7β-(N-ethyl-4-bromophenethylcarbamoyl)-6,14-endoethanotetrahydronorcodide, N-cyclopropylmethyl-7α-(N-ethyl-4-bromophenethylcarbamoyl)-6,14-endoethenotetrahydronororipavine, N-cyclopropylmethyl-7β-(N-ethyl-4-bromophenethylcarbamoyl)-6,14-endoethenotetrahydronororipavine, N-cyclopropylmethyl-7α-(N-ethyl-4-bromophenethylcarbamoyl)-6,14-endoethanotetrahydronororipavine, N-cyclopropylmethyl-7β-(N-ethyl-4-bromophenethylcarbamoyl)- 6,14-endoethanotetrahydronororipavine, N-cyclopropylmethyl-7α-(N-ethyl-4-bromophenethylcarbamoyl)-6,14-endoethenotetrahydronorthebaine, N-cyclopropylmethyl-7β-(N-ethyl-4-bromophenethylcarbamoyl)-6,14-endoethenotetrahydronorthebaine, N-cyclopropylmethyl-7α-(N-ethyl-4-bromophenethylcarbamoyl)-6,14-endoethanotetrahydronorthebaine, N-cyclopropylmethyl-7β-(N-ethyl-4-bromophenethylcarbamoyl)-6,14-endoethanotetrahydronorthebaine, N-cyclopropylmethyl-7α-(N-ethyl-4-bromophenethylcarbamoyl)-8β-methyl-6,14-endoethenotetrahydronormorphide, N-cyclopropylmethyl-7β-(N-ethyl-4-bromophenethylcarbamoyl)-8α-methyl-6,14-endoethenotetrahydronormorphide, N-cyclopropylmethyl-7α-(N-ethyl-4-bromophenethylcarbamoyl)-8β-methyl-6,14-endoethanotetrahydronormorphide, N-cyclopropylmethyl-7β-(N-ethyl-4-bromophenethylcarbamoyl)-8α-methyl-6,14-endoethanotetrahydronormorphide, N-cyclopropylmethyl-7α-(N-ethyl-4-bromophenethylcarbamoyl)-8β-methyl-6,14-endoethenotetrahydronorcodide, N-cyclopropylmethyl-7β-(N-ethyl-4-bromophenethylcarbamoyl)-8α-methyl-6,14-endoethenotetrahydronorcodide, N-cyclopropylmethyl-7α-(N-ethyl-4-bromophenethylcarbamoyl)-8β-methyl-6,14-endoethanotetrahydronorcodide, N-cyclopropylmethyl-7β-(N-ethyl-4-bromophenethylcarbamoyl)-8α-methyl-6,14-endoethanotetrahydronorcodide, N-cyclopropylmethyl-7α-(N-ethyl- 4-bromophenethylcarbamoyl)-8β-methyl-6,14-endoethenotetrahydronororipavine, N-cyclopropylmethyl-7β-(N-ethyl-4-bromophenethylcarbamoyl)-8α-methyl-6,14-endoethenotetrahydronororipavine, N-cyclopropylmethyl-7α-(N-ethyl-4-bromophenethylcarbamoyl)-8β-methyl-6,14-endoethanotetrahydronororipavine, N-cyclopropylmethyl-7β-(N-ethyl-4-bromophenethylcarbamoyl)-8α-methyl-6,14-endoethanotetrahydronororipavine, N-cyclopropylmethyl-7α-(N-ethyl-4-bromophenethylcarbamoyl)-8β-methyl-6,14-endoethenotetrahydronorthebaine, N-cyclopropylmethyl-7β-(N-ethyl-4-bromophenethylcarbamoyl)-8α-methyl-6,14-endoethenotetrahydronorthebaine, N-cyclopropylmethyl-7α-(N-ethyl-4-bromophenethylcarbamoyl)-8β-methyl-6,14-endoethanotetrahydronorthebaine, N-cyclopropylmethyl-7β-(N-ethyl-4-bromophenethylcarbamoyl)-8α-methyl-6,14-endoethanotetrahydronorthebaine, N-cyclopropylmethyl-7β-methyl-7α-(N-ethyl-4-bromophenethylcarbamoyl)-6,14-endoethenotetrahydronormorphide, N-cyclopropylmethyl-7α-methyl-7β-(N-ethyl-4-bromophenethylcarbamoyl)-6,14-endoethenotetrahydronormorphide, N-cyclopropylmethyl-7β-methyl-7α-(N-ethyl-4-bromophenethylcarbamoyl)-6,14-endoethanotetrahydronormorphide, N-cyclopropylmethyl-7α-methyl-7β-(N-ethyl-4-bromophenethylcarbamoyl)-6,14-endoethanotetrahydronormorphide, N-cyclopropylmethyl-7β-methyl-7α-(N-ethyl-4-bromophenethylcarbamoyl)-6,14-endoethenotetrahydronorcodide, N-cyclopropylmethyl-7α-methyl-7β-(N-ethyl-4-bromophenethylcarbamoyl)-6,14-endoethenotetrahydronorcodide, N-cyclopropylmethyl-7β-methyl-7α-(N-ethyl-4-bromophenethylcarbamoyl)-6,14-endoethanotetrahydronorcodide, N-cyclopropylmethyl-7α-methyl-7β-(N-ethyl-4-bromophenethylcarbamoyl)-6,14-endoethanotetrahydronorcodide, N-cyclopropylmethyl-7β-methyl-7α-(N-ethyl-4-bromophenethylcarbamoyl)-6,14-endoethenotetrahydronororipavine, N-cyclopropylmethyl-7α-methyl-7β-(N-ethyl-4-bromophenethylcarbamoyl)-6,14-endoethenotetrahydronororipavine, N-cyclopropylmethyl-7β-methyl-7α-(N-ethyl-4-bromophenethylcarbamoyl)-6,14-endoethanotetrahydronororipavine, N-cyclopropylmethyl-7α-methyl-7β-(N-ethyl-4-bromophenethylcarbamoyl)-6,14-endoethanotetrahydronororipavine, N-cyclopropylmethyl-7β-methyl-7α-(N-ethyl-4-bromophenethylcarbamoyl)-6,14-endoethenotetrahydronorthebaine, N-cyclopropylmethyl-7α-methyl-7β-(N-ethyl-4-bromophenethylcarbamoyl)-6,14-endoethenotetrahydronorthebaine, N-cyclopropylmethyl-7β-methyl-7α-(N-ethyl-4-bromophenethylcarbamoyl)-6,14-endoethanotetrahydronorthebaine, N-cyclopropylmethyl-7α-methyl-7β-(N-ethyl-4-bromophenethylcarbamoyl)-6,14-endoethanotetrahydronorthebaine, N-cyclopropylmethyl-7α-(3-phenylpropylcarbamoyl)-6,14-endoethenotetrahydronormorphide, N-cyclopropylmethyl-7β-(3-phenylpropylcarbamoyl)- 6,14-endoethenotetrahydronormorphide, N-cyclopropylmethyl-7α-(3-phenylpropylcarbamoyl)-6,14-endoethanotetrahydronormorphide, N-cyclopropylmethyl-7β-(3-phenylpropylcarbamoyl)-6,14-endoethanotetrahydronormorphide, N-cyclopropylmethyl-7α-(3-phenylpropylcarbamoyl)-6,14-endoethenotetrahydronorcodide, N-cyclopropylmethyl-7β-(3-phenylpropylcarbamoyl)-6,14- endoethenotetrahydronorcodide, N-cyclopropylmethyl-7α-(3-phenylpropylcarbamoyl)-6,14-endoethanotetrahydronorcodide, N-cyclopropylmethyl-7β-(3-phenylpropylcarbamoyl)-6,14-endoethanotetrahydronorcodide, N-cyclopropylmethyl-7β-(3-phenylpropylcarbamoyl)-6,14-endoethenotetrahydronororipavine, N-cyclopropylmethyl-7β-(3-phenylpropylcarbamoyl)-6,14-endoethenotetrahydronororipavine, N-cyclopropylmethyl-7α-(3-phenylpropylcarbamoyl)-6,14-endoethanotetrahydronororipavine, N-cyclopropylmethyl-7β-(3-phenylpropylcarbamoyl)-6,14-endoethanotetrahydronororipavine, N-cyclopropylmethyl-7α-(3-phenylpropylcarbamoyl)-6,14-endoethenotetrahydronorthebaine, N-cyclopropylmethyl-7β-(3-phenylpropylcarbamoyl)-6,14-endoethenotetrahydronorthebaine, N-cyclopropylmethyl-7α-(3-phenylpropylcarbamoyl)-6,14-endoethanotetrahydronorthebaine, N-cyclopropylmethyl-7β-(3-phenylpropylcarbamoyl)-6,14-endoethanotetrahydronorthebaine, N-cyclopropylmethyl-7α-(4-phenylbutylcarbamoyl)-6,14-endoethenotetrahydronormorphide, N-cyclopropylmethyl-7β-(4-phenylbutylcarbamoyl)-6,14-endoethenotetrahydronormorphide, N-cyclopropylmethyl-7α-(4-phenylbutylcarbamoyl)-6,14-endoethanotetrahydronormorphide, N-cyclopropylmethyl-7β-(4-phenylbutylcarbamoyl)-6,14-endoethanotetrahydronormorphide, N-cyclopropylmethyl-7α-(4-phenylbutylcarbamoyl)-6,14-endoethenotetrahydronorcodide, N-cyclopropylmethyl-7β-(4-phenylbutylcarbamoyl)-6,14-endoethenotetrahydronorcodide, N-cyclopropylmethyl-7α-(4-phenylbutylcarbamoyl)-6,14-endoethanotetrahydronorcodide, N-cyclopropylmethyl-7β-(4-phenylbutylcarbamoyl)-6,14-endoethanotetrahydronorcodide, N-cyclopropylmethyl-7α-(4-phenylbutylcarbamoyl)-6,14-endoethenotetrahydronororipavine, N-cyclopropylmethyl-7β-(4-phenylbutylcarbamoyl)-6,14-endoethenotetrahydronororipavine, N-cyclopropylmethyl-7α-(4-phenylbutylcarbamoyl)-6,14-endoethanotetrahydronororipavine, N-cyclopropylmethyl-7β-(4-phenylbutylcarbamoyl)-6,14-endoethanotetrahydronororipavine, N-cyclopropylmethyl-7α-(4-phenylbutylcarbamoyl)-6,14-endoethenotetrahydronorthebaine, N-cyclopropylmethyl-7β-(4-phenylbutylcarbamoyl)-6,14-endoethenotetrahydronorthebaine, N-cyclopropylmethyl-7α-(4-phenylbutylcarbamoyl)-6,14-endoethanotetrahydronorthebaine, N-cyclopropylmethyl-7β-(4-phenylbutylcarbamoyl)-6,14-endoethanotetrahydronorthebaine, N-cyclopropylmethyl-7α-(10-phenyldecylcarbamoyl)-6,14-endoethenotetrahydronormorphide, N-cyclopropylmethyl-7β-(10-phenyldecylcarbamoyl)-6,14-endoethenotetrahydronormorphide, N-cyclopropylmethyl-7α-(10-phenyldecylcarbamoyl)-6,14-endoethanotetrahydronormorphide, N-cyclopropylmethyl-7β-(10-phenyldecylcarbamoyl)-6,14-endoethanotetrahydronormorphide, N-cyclopropylmethyl-7α-(10-phenyldecylcarbamoyl)-6,14-endoethenotetrahydronorcodide, N-cyclopropylmethyl-7β-(10-phenyldecylcarbamoyl)-6,14-endoethenotetrahydronorcodide, N-cyclopropylmethyl-7α-(10-phenyldecylcarbamoyl)-6,14-endoethanotetrahydronorcodide, N-cyclopropylmethyl-7β-(10-phenyldecylcarbamoyl)-6,14-endoethanotetrahydronorcodide, N-cyclopropylmethyl-7α-(10-phenyldecylcarbamoyl)-6,14-endoethenotetrahydronororipavine, N-cyclopropylmethyl-7β-(10-phenyldecylcarbamoyl)-6,14-endoethenotetrahydronororipavine, N-cyclopropylmethyl-7α-(10-phenyldecylcarbamoyl)-6,14-endoethanotetrahydronororipavine, N-cyclopropylmethyl-7β-(10-phenyldecylcarbamoyl)-6,14-endoethanotetrahydronororipavine, N-cyclopropylmethyl-7α-(10-phenyldecylcarbamoyl)-6,14-endoethenotetrahydronorthebaine, N-cyclopropylmethyl-7β-(10-phenyldecylcarbamoyl)-6,14-endoethenotetrahydronorthebaine, N-cyclopropylmethyl-7α-(10-phenyldecylcarbamoyl)-6,14-endoethanotetrahydronorthebaine, N-cyclopropylmethyl-7β-(10-phenyldecylcarbamoyl)-6,14-endoethanotetrahydronorthebaine, N-cyclopropylmethyl-7α-decylcarbamoyl-6,14-endoethenotetrahydronormorphide, N-cyclopropylmethyl-7β-decylcarbamoyl-6,14-endoethenotetrahydronormorphide, N-cyclopropylmethyl-7α-decylcarbamoyl-6,14-endoethanotetrahydronormorphide, N-cyclopropylmethyl-7β-decylcarbamoyl-6,14-endoethanotetrahydronormorphide, N-cyclopropylmethyl-7α-decylcarbamoyl-6,14-endoethenotetrahydronorcodide, N-cyclopropylmethyl-7β-decylcarbamoyl-6,14-endoethenotetrahydronorcodide, N-cyclopropylmethyl-7α-decylcarbamoyl-6,14-endoethanotetrahydronorcodide, N-cyclopropylmethyl-7β-decylcarbamoyl-6,14-endoethanotetrahydronorcodide, N-cyclopropylmethyl-7α-decylcarbamoyl-6,14-endoethenotetrahydronororipavine, N-cyclopropylmethyl-7β-decylcarbamoyl-6,14-endoethenotetrahydronororipavine, N-cyclopropylmethyl-7α-decylcarbamoyl-6,14-endoethanotetrahydronororipavine, N-cyclopropylmethyl-7β-decylcarbamoyl-6,14-endoethanotetrahydronororipavine, N-cyclopropylmethyl-7α-decylcarbamoyl-6,14-endoethenotetrahydronorthebaine, N-cyclopropylmethyl-7β-decylcarbamoyl-6,14-endoethenotetrahydronorthebaine, N-cyclopropylmethyl-7α-decylcarbamoyl-6,14-endoethanotetrahydronorthebaine, N-cyclopropylmethyl-7β-decylcarbamoyl-6,14-endoethanotetrahydronorthebaine, N-cyclopropylmethyl-7α-allylcarbamoyl-6,14-endoethenotetrahydronormorphide, N-cyclopropylmethyl-7β-allylcarbamoyl-6,14-endoethenotetrahydronormorphide, N-cyclopropylmethyl-7α-allylcarbamoyl-6,14-endoethanotetrahydronormorphide, N-cyclopropylmethyl-7β-allylcarbamoyl-6,14-endoethanotetrahydronormorphide, N-cyclopropylmethyl-7α-allylcarbamoyl-6,14-endoethenotetrahydronorcodide, N-cyclopropylmethyl-7β-allylcarbamoyl-6,14-endoethenotetrahydronorcodide, N-cyclopropylmethyl-7α-allylcarbamoyl-6,14-endoethanotetrahydronorcodide, N-cyclopropylmethyl-7β-allylcarbamoyl-6,14-endoethanotetrahydronorcodide, N-cyclopropylmethyl-7α-allylcarbamoyl-6,14-endoethenotetrahydronororipavine, N-cyclopropylmethyl-7β-allylcarbamoyl-6,14-endoethenotetrahydronororipavine, N-cyclopropylmethyl-7α-allylcarbamoyl-6,14-endoethanotetrahydronororipavine, N-cyclopropylmethyl-7β-allylcarbamoyl-6,14-endoethanotetrahydronororipavine, N-cyclopropylmethyl-7α-allylcarbamoyl-6,14-endoethenotetrahydronorthebaine, N-cyclopropylmethyl-7β-allylcarbamoyl-6,14-endoethenotetrahydronorthebaine, N-cyclopropylmethyl-7α-allylcarbamoyl-6,14- endoethanotetrahydronorthebaine, N-cyclopropylmethyl-7β-allylcarbamoyl-6,14-endoethanotetrahydronorthebaine, N-cyclopropylmethyl-7α-propargylcarbamoyl-6,14-endoethenotetrahydronormorphide, N-cyclopropylmethyl-7β-propargylcarbamoyl-6,14-endoethenotetrahydronormorphide, N-cyclopropylmethyl-7α-propargylcarbamoyl-6,14-endoethanotetrahydronormorphide, N-cyclopropylmethyl-7β-propargylcarbamoyl-6,14-endoethanotetrahydronormorphide, N-cyclopropylmethyl-7α-propargylcarbamoyl-6,14-endoethenotetrahydronorcodide, N-cyclopropylmethyl-7β-propargylcarbamoyl-6,14-endoethenotetrahydronorcodide, N-cyclopropylmethyl-7α-propargylcarbamoyl-6,14-endoethanotetrahydronorcodide, N-cyclopropylmethyl-7β-propargylcarbamoyl-6,14-endoethanotetrahydronorcodide, N-cyclopropylmethyl-7α-propargylcarbamoyl-6,14-endoethenotetrahydronororipavine, N-cyclopropylmethyl-7β-propargylcarbamoyl-6,14-endoethenotetrahydronororipavine, N-cyclopropylmethyl-7α-propargylcarbamoyl-6,14-endoethanotetrahydronororipavine, N-cyclopropylmethyl-7β-propargylcarbamoyl-6,14-endoethanotetrahydronororipavine, N-cyclopropylmethyl-7α-propargylcarbamoyl-6,14-endoethenotetrahydronorthebaine, N-cyclopropylmethyl-7β-propargylcarbamoyl-6,14-endoethenotetrahydronorthebaine, N-cyclopropylmethyl-7α-propargylcarbamoyl-6,14-endoethanotetrahydronorthebaine, N-cyclopropylmethyl-7β-propargylcarbamoyl-6,14-endoethanotetrahydronorthebaine, N-cyclopropylmethyl-7α-(N-allylmethylcarbamoyl)- 6,14-endoethenotetrahydronormorphide, N-cyclopropylmethyl-7β-(N-allylmethylcarbamoyl)-6,14-endoethenotetrahydronormorphide, N-cyclopropylmethyl-7α-(N-allylmethylcarbamoyl)-6,14-endoethanotetrahydronormorphide, N-cyclopropylmethyl-7β-(N-allylmethylcarbamoyl)-6,14-endoethanotetrahydronormorphide, N-cyclopropylmethyl-7α-(N-allylmethylcarbamoyl)-6,14-endoethenotetrahydronorcodide, N-cyclopropylmethyl-7β-(N-allylmethylcarbamoyl)-6,14-endoethenotetrahydronorcodide, N-cyclopropylmethyl-7α-(N-allylmethylcarbamoyl)-6,14-endoethanotetrahydronorcodide, N-cyclopropylmethyl-7β-(N-allylmethylcarbamoyl)-6,14-endoethanotetrahydronorcodide, N-cyclopropylmethyl-7α-(N-allylmethylcarbamoyl)-6,14-endoethenotetrahydronororipavine, N-cyclopropylmethyl-7β-(N-allylmethylcarbamoyl)-6,14-endoethenotetrahydronororipavine, N-cyclopropylmethyl-7α-(N-allylmethylcarbamoyl)-6,14-endoethanotetrahydronororipavine, N-cyclopropylmethyl-7β-(N-allylmethylcarbamoyl)-6,14-endoethanotetrahydronororipavine, N-cyclopropylmethyl-7α-(N-allylmethylcarbamoyl)-6,14-endoethenotetrahydronorthebaine, N-cyclopropylmethyl-7β-(N-allylmethylcarbamoyl)-6,14-endoethenotetrahydronorthebaine, N-cyclopropylmethyl-7α-(N-allylmethylcarbamoyl)-6,14-endoethanotetrahydronorthebaine, N-cyclopropylmethyl-7β-(N-allylmethylcarbamoyl)-6,14-endoethanotetrahydronorthebaine, N-cyclopropylmethyl-7α-(N,N-(2,3-benzopentamethylene)carbamoyl)-6,14-endoethenotetrahydronormorphide, N-cyclopropylmethyl-7β-(N,N-(2,3-benzopentamethylene)carbamoyl)-6,14-endoethenotetrahydronormorphide, N-cyclopropylmethyl-7α-(N,N-(2,3-benzopentamethylene)carbamoyl)-6,14-endoethanotetrahydronormorphide, N-cyclopropylmethyl-7β-(N,N-(2,3-benzopentamethylene)carbamoyl)-6,14-endoethanotetrahydronormorphide, N-cyclopropylmethyl-7α-(N,N-(2,3-benzopentamethylene)carbamoyl)-6,14-endoethenotetrahydronorcodide, N-cyclopropylmethyl-7β-(N,N-(2,3-benzopentamethylene)carbamoyl)-6,14-endoethenotetrahydronorcodide, N-cyclopropylmethyl-7α-(N,N-(2,3-benzopentamethylene)carbamoyl)-6,14-endoethanotetrahydronorcodide, N-cyclopropylmethyl-7β-(N,N-(2,3-benzopentamethylene)carbamoyl)-6,14-endoethanotetrahydronorcodide, N-cyclopropylmethyl-7α-(N,N-(2,3-benzopentamethylene)carbamoyl)-6,14-endoethenotetrahydronororipavine, N-cyclopropylmethyl-7β-(N,N-(2,3-benzopentamethylene)carbamoyl)-6,14-endoethenotetrahydronororipavine, N-cyclopropylmethyl-7α-(N,N-(2,3-benzopentamethylene)carbamoyl)-6,14-endoethanotetrahydronororipavine, N-cyclopropylmethyl-7β-(N,N-(2,3-benzopentamethylene)carbamoyl)-6,14-endoethanotetrahydronororipavine, N-cyclopropylmethyl-7α-(N,N-(2,3-benzopentamethylene)carbamoyl)-6,14-endoethenotetrahydronorthebaine, N-cyclopropylmethyl-7β-(N,N-(2,3-benzopentamethylene)carbamoyl)-6,14-endoethenotetrahydronorthebaine, N-cyclopropylmethyl-7α-(N,N-(2,3-benzopentamethylene)carbamoyl)-6,14-endoethanotetrahydronorthebaine, N-cyclopropylmethyl-7β-(N,N-(2,3-benzopentamethylene)carbamoyl)-6,14-endoethanotetrahydronorthebaine, N-cyclopropylmethyl-7α-benzoylamino-6,14-endoethenotetrahydronormorphide, N-cyclopropylmethyl-7β-benzoylamino-6,14-endoethenotetrahydronormorphide, N-cyclopropylmethyl-7α-benzoylamino-6,14-endoethanotetrahydronormorphide, N-cyclopropylmethyl-7β-benzoylamino-6,14-endoethanotetrahydronormorphide, N-cyclopropylmethyl-7α-benzoylamino-6,14-endoethenotetrahydronorcodide, N-cyclopropylmethyl-7β-benzoylamino-6,14-endoethenotetrahydronorcodide, N-cyclopropylmethyl-7α-benzoylamino-6,14-endoethanotetrahydronorcodide, N-cyclopropylmethyl-7β-benzoylamino-6,14-endoethanotetrahydronorcodide, N-cyclopropylmethyl-7α-benzoylamino-6,14-endoethenotetrahydronororipavine, N-cyclopropylmethyl-7β-benzoylamino-6,14-endoethenotetrahydronororipavine, N-cyclopropylmethyl-7α-benzoylamino-6,14-endoethanotetrahydronororipavine, N-cyclopropylmethyl-7β-benzoylamino-6,14-endoethanotetrahydronororipavine, N-cyclopropylmethyl-7α-benzoylamino-6,14-endoethenotetrahydronorthebaine, N-cyclopropylmethyl-7β-benzoylamino-6,14-endoethenotetrahydronorthebaine, N-cyclopropylmethyl-7α-benzoylamino-6,14-endoethanotetrahydronorthebaine, N-cyclopropylmethyl-7β-benzoylamino-6,14-endoethanotetrahydronorthebaine, N-cyclopropylmethyl-7α-(3-phenylpropionylamino)-6,14-endoethenotetrahydronormorphide, N-cyclopropylmethyl-7β-(3-phenylpropionylamino)-6,14-endoethenotetrahydronormorphide, N-cyclopropylmethyl-7α-(3-phenylpropionylamino)-6,14-endoethanotetrahydronormorphide, N-cyclopropylmethyl-7β-(3-phenylpropionylamino)-6,14-endoethanotetrahydronormorphide, N-cyclopropylmethyl-7α-(3-phenylpropionylamino)-6,14-endoethenotetrahydronorcodide, N-cyclopropylmethyl-7β-(3-phenylpropionylamino)-6,14-endoethenotetrahydronorcodide, N-cyclopropylmethyl-7α-(3-phenylpropionylamino)-6,14-endoethanotetrahydronorcodide, N-cyclopropylmethyl-7β-

(3-phenylpropionylamino)-6,14-endoethanotetrahydronorcodide, N-cyclopropylmethyl-7α-(3-phenylpropionylamino)-6,14-endoethenotetrahydronororipavine, N-cyclopropylmethyl-7β-(3-phenylpropionylamino)-6,14-endoethenotetrahydronororipavine, N-cyclopropylmethyl-7α-(3-phenylpropionylamino)-6,14-endoethanotetrahydronororipavine, N-cyclopropylmethyl-7β-(3-phenylpropionylamino)-6,14-endoethanotetrahydronororipavine, N-cyclopropylmethyl-7α-(3-phenylpropionylamino)-6,14-endoethenotetrahydronorthebaine, N-cyclopropylmethyl-7β-(3-phenylpropionylamino)-6,14-endoethenotetrahydronorthebaine, N-cyclopropylmethyl-7α-(3-phenylpropionylamino)-6,14-endoethanotetrahydronorthebaine, N-cyclopropylmethyl-7β-(3-phenylpropionylamino)-6,14-endoethanotetrahydronorthebaine, N-cyclopropylmethyl-7α-(5-phenylvalerylamino)-6,14-endoethenotetrahydronormorphide, N-cyclopropylmethyl-7β-(5-phenylvalerylamino)-6,14-endoethenotetrahydronormorphide, N-cyclopropylmethyl-7α-(5-phenylvalerylamino)-6,14-endoethanotetrahydronormorphide, N-cyclopropylmethyl-7β-(5-phenylvalerylamino)-6,14-endoethanotetrahydronormorphide, N-cyclopropylmethyl-7α-(5-phenylvalerylamino)-6,14-endoethenotetrahydronorcodide, N-cyclopropylmethyl-7β-(5-phenylvalerylamino)-6,14-endoethenotetrahydronorcodide, N-cyclopropylmethyl-7α-(5-phenylvalerylamino)-6,14-endoethanotetrahydronorcodide, N-cyclopropylmethyl-7β-(5-phenylvalerylamino)-6,14-endoethanotetrahydronorcodide, N-cyclopropylmethyl-7α-(5-phenylvalerylamino)-6,14-endoethenotetrahydronororipavine, N-cyclopropylmethyl-7β-(5-phenylvalerylamino)-6,14-endoethenotetrahydronororipavine, N-cyclopropylmethyl-7α-(5-phenylvalerylamino)-6,14-endoethanotetrahydronororipavine, N-cyclopropylmethyl-7β-(5-phenylvalerylamino)-6,14-endoethanotetrahydronororipavine, N-cyclopropylmethyl-7α-(5-phenylvalerylamino)-6,14-endoethenotetrahydronorthebaine, N-cyclopropylmethyl-7β-(5-phenylvalerylamino)-6,14-endoethenotetrahydronorthebaine, N-cyclopropylmethyl-7α-(5-phenylvalerylamino)-6,14-endoethanotetrahydronorthebaine, N-cyclopropylmethyl-7β-(5-phenylvalerylamino)-6,14-endoethanotetrahydronorthebaine, N-cyclopropylmethyl-7α-cinnamoylamino-6,14-endoethenotetrahydronormorphide, N-cyclopropylmethyl-7β-cinnamoylamino-6,14-endoethenotetrahydronormorphide, N-cyclopropylmethyl-7α-cinnamoylamino-6,14-endoethanotetrahydronormorphide, N-cyclopropylmethyl-7β-cinnamoylamino-6,14-endoethanotetrahydronormorphide, N-cyclopropylmethyl-7α-cinnamoylamino-6,14-endoethenotetrahydronorcodide, N-cyclopropylmethyl-7β-cinnamoylamino-6,14-endoethenotetrahydronorcodide, N-cyclopropylmethyl-7α-cinnamoylamino-6,14-endoethanotetrahydronorcodide, N-cyclopropylmethyl-7β-cinnamoylamino-6,14-endoethanotetrahydronorcodide, N-cyclopropylmethyl-7α-cinnamoylamino-6,14-endoethenotetrahydronororipavine, N-cyclopropylmethyl-7β-cinnamoylamino-6,14-endoethenotetrahydronororipavine, N-cyclopropylmethyl-7α-cinnamoylamino-6,14-endoethanotetrahydronororipavine, N-cyclopropylmethyl-7β-cinnamoylamino-6,14-endoethanotetrahydronororipavine, N-cyclopropylmethyl-7α-cinnamoylamino-6,14-endoethenotetrahydronorthebaine, N-cyclopropylmethyl-7β-cinnamoylamino-6,14-endoethenotetrahydronorthebaine, N-cyclopropylmethyl-7α-cinnamoylamino-6,14-endoethanotetrahydronorthebaine, N-cyclopropylmethyl-7β-cinnamoylamino-6,14-endoethanotetrahydronorthebaine, N-cyclopropylmethyl-7α-(5-phenyl-2,4-pentadienoylamino)-6,14-endoethenotetrahydronormorphide, N-cyclopropylmethyl-7β-(5-phenyl-2,4-pentadienoylamino)-6,14-endoethenotetrahydronormorphide, N-cyclopropylmethyl-7α-(5-phenyl-2,4-pentadienoylamino)-6,14-endoethanotetrahydronormorphide, N-cyclopropylmethyl-7β-(5-phenyl-2,4-pentadienoylamino)-6,14-endoethanotetrahydronormorphide, N-cyclopropylmethyl-7α-(5-phenyl-2,4-pentadienoylamino)-6,14-endoethenotetrahydronorcodide, N-cyclopropylmethyl-7β-(5-phenyl-2,4-pentadienoylamino)-6,14-endoethenotetrahydronorcodide, N-cyclopropylmethyl-7α-(5-phenyl-2,4-pentadienoylamino)-6,14-endoethanotetrahydronorcodide, N-cyclopropylmethyl-7β-(5-phenyl-2,4-pentadienoylamino)-6,14-endoethanotetrahydronorcodide, N-cyclopropylmethyl-7α-(5-phenyl-2,4-pentadienoylamino)-6,14-endoethenotetrahydronororipavine, N-cyclopropylmethyl-7β-(5-phenyl-2,4-pentadienoylamino)-6,14-endoethenotetrahydronororipavine, N-cyclopropylmethyl-7α-(5-phenyl-2,4-pentadienoylamino)-6,14-endoethanotetrahydronororipavine, N-cyclopropylmethyl-7β-(5-phenyl-2,4-pentadienoylamino)-6,14-endoethanotetrahydronororipavine, N-cyclopropylmethyl-7α-(5-phenyl-2,4-pentadienoylamino)-6,14-endoethenotetrahydronorthebaine, N-cyclopropylmethyl-7β-(5-phenyl-2,4-pentadienoylamino)-6,14-endoethenotetrahydronorthebaine, N-cyclopropylmethyl-7α-(5-phenyl-2,4-pentadienoylamino)-6,14-endoethanotetrahydronorthebaine, N-cyclopropylmethyl-7β-(5-phenyl-2,4-pentadienoylamino)-6,14-endoethanotetrahydronorthebaine, N-cyclopropylmethyl-7α-(4-phenylbenzoylamino)-6,14-endoethenotetrahydronormorphide, N-cyclopropylmethyl-7β-(4-phenylbenzoylamino)-6,14-endoethenotetrahydronormorphide, N-cyclopropylmethyl-7α-(4-phenylbenzoylamino)-6,14-endoethanotetrahydronormorphide, N-cyclopropylmethyl-7β-(4-phenylbenzoylamino)-6,14-endoethanotetrahydronormorphide, N-cyclopropylmethyl-7α-(4-phenylbenzoylamino)-6,14-endoethenotetrahydronorcodide, N-cyclopropylmethyl-7β-(4-phenylbenzoylamino)-6,14-endoethenotetrahydronorcodide, N-cyclopropylmethyl-7α-(4-phenylbenzoylamino)-6,14-endoethanotetrahydronorcodide, N-cyclopropylmethyl-7β-(4-phenylbenzoylamino)-6,14-endoethanotetrahydronorcodide, N-cyclopropylmethyl-7α-(4-phenylbenzoylamino)-6,14-endoethenotetrahydronororipavine, N-cyclopropylmethyl-7β-(4-phenylbenzoylamino)-6,14-endoethenotetrahydronororipavine, N-cyclopropylmethyl-7α-(4-phenylbenzoylamino)-6,14-endoethanotetrahydronororipavine, N-cyclopropylmethyl-7β-(4-phenylbenzoylamino)-6,14- endoethanotetrahydronororipavine, N-cyclopropylmethyl-7α-(4-phenylbenzoylamino)-6,14-endoethenotetrahydronorthebaine, N-cyclopropylmethyl-7β-(4-phenylbenzoylamino)-6,14-endoethenotetrahydronorthebaine, N-cyclopropylmethyl-7α-(4-phenylbenzoylamino)-6,14-endoethanotetrahydronorthebaine, N-cyclopropylmethyl-7β-(4-phenylbenzoylamino)-6,14-endoethanotetrahydronorthebaine, N-cyclopropylmethyl-7α-benzylsulfonylamino-6,14-endoethenotetrahydronormorphide, N-cyclopropylmethyl-7β-benzylsulfonylamino-6,14-endoethenotetrahydronormorphide, N-cyclopropylmethyl-7α-benzylsulfonylamino-6,14-endoethanotetrahydronormorphide, N-cyclopropylmethyl-7β-benzylsulfonylamino-6,14-endoethanotetrahydronormorphide, N-cyclopropylmethyl-7α-benzylsulfonylamino-6,14-endoethenotetrahydronorcodide, N-cyclopropylmethyl-7β-benzylsulfonylamino-6,14-endoethenotetrahydronorcodide, N-cyclopropylmethyl-7α-benzylsulfonylamino-6,14-endoethanotetrahydronorcodide, N-cyclopropylmethyl-7β-benzylsulfonylamino-6,14-endoethanotetrahydronorcodide, N-cyclopropylmethyl-7α-benzylsulfonylamino-6,14-endoethenotetrahydronororipavine, N-cyclopropylmethyl-7β-benzylsulfonylamino-6,14-endoethenotetrahydronororipavine, N-cyclopropylmethyl-7α-benzylsulfonylamino-6,14-endoethanotetrahydronororipavine, N-cyclopropylmethyl-7β-benzylsulfonylamino-6,14-endoethanotetrahydronororipavine, N-cyclopropylmethyl-7β-benzylsulfonylamino-6,14-endoethenotetrahydronorthebaine, N-cyclopropylmethyl-7β-benzylsulfonylamino-6,14-endoethenotetrahydronorthebaine, N-cyclopropylmethyl-7α-benzylsulfonylamino-6,14-endoethanotetrahydronorthebaine, N-cyclopropylmethyl-7β-benzylsulfonylamino-6,14-endoethanotetrahydronorthebaine, N-phenethyl-7α-phenethylcarbamoyl-6,14-endoethenotetrahydronormorphide, N-phenethyl-7β-phenethylcarbamoyl-6,14-endoethenotetrahydronormorphide, N-phenethyl-7α-phenethylcarbamoyl-6,14-endoethanotetrahydronormorphide, N-phenethyl-7β-phenethylcarbamoyl-6,14-endoethanotetrahydronormorphide, N-phenethyl-7α-phenethylcarbamoyl-6,14-endoethenotetrahydronorcodide, N-phenethyl-7β-phenethylcarbamoyl-6,14-endoethenotetrahydronorcodide, N-phenethyl-7α-phenethylcarbamoyl-6,14-endoethanotetrahydronorcodide, N-phenethyl-7β-phenethylcarbamoyl-6,14-endoethanotetrahydronorcodide, N-phenethyl-7α-phenethylcarbamoyl-6,14-endoethenotetrahydronororipavine, N-phenethyl-7β-phenethylcarbamoyl-6,14-endoethenotetrahydronororipavine, N-phenethyl-7α-phenethylcarbamoyl-6,14-endoethanotetrahydronororipavine, N-phenethyl-7β-phenethylcarbamoyl-6,14-endoethanotetrahydronororipavine, N-phenethyl-7α-phenethylcarbamoyl-6,14-endoethenotetrahydronorthebaine, N-phenethyl-7β-phenethylcarbamoyl-6,14-endoethenotetrahydronorthebaine, N-phenethyl-7α-phenethylcarbamoyl-6,14-endoethanotetrahydronorthebaine, N-phenethyl-7β-phenethylcarbamoyl-6,14-endoethanotetrahydronorthebaine, N-phenethyl-7α-allylcarbamoyl-6,14-endoethenotetrahydronormorphide, N-phenethyl-7β-allylcarbamoyl-6,14-endoethenotetrahydronormorphide, N-phenethyl-7α-allylcarbamoyl-6,14-endoethanotetrahydronormorphide, N-phenethyl-7β-allylcarbamoyl-6,14-endoethanotetrahydronormorphide, N-phenethyl-7α-allylcarbamoyl-6,14-endoethenotetrahydronorcodide, N-phenethyl-7β-allylcarbamoyl-6,14-endoethenotetrahydronorcodide, N-phenethyl-7α-allylcarbamoyl-6,14-endoethanotetrahydronorcodide, N-phenethyl-7β-allylcarbamoyl-6,14-endoethanotetrahydronorcodide, N-phenethyl-7α-allylcarbamoyl-6,14-endoethenotetrahydronororipavine, N-phenethyl-7β-allylcarbamoyl-6,14-endoethenotetrahydronororipavine, N-phenethyl-7α-allylcarbamoyl- 6,14-endoethanotetrahydronororipavine, N-phenethyl-7β-allylcarbamoyl-6,14-endoethanotetrahydronororipavine, N-phenethyl-7α-allylcarbamoyl-6,14-endoethenotetrahydronorthebaine, N-phenethyl-7β-allylcarbamoyl-6,14-endoethenotetrahydronorthebaine, N-phenethyl-7α-allylcarbamoyl-6,14-endoethanotetrahydronorthebaine, N-phenethyl-7β-allylcarbamoyl-6,14-endoethanotetrahydronorthebaine, N-phenethyl-7α-(N-methylphenethylcarbamoyl)-6,14-endoethenotetrahydronormorphide, N-phenethyl-7β-(N-methylphenethylcarbamoyl)-6,14-endoethenotetrahydronormorphide, N-phenethyl-7α-(N-methylphenethylcarbamoyl)-6,14-endoethanotetrahydronormorphide, N-phenethyl-7β-(N-methylphenethylcarbamoyl)-6,14-endoethanotetrahydronormorphide, N-phenethyl-7α-(N-methylphenethylcarbamoyl)-6,14-endoethenotetrahydronorcodide, N-phenethyl-7β-(N-methylphenethylcarbamoyl)-6,14-endoethenotetrahydronorcodide, N-phenethyl-7α-(N-methylphenethylcarbamoyl)-6,14-endoethanotetrahydronorcodide, N-phenethyl-7β-(N-methylphenethylcarbamoyl)-6,14-endoethanotetrahydronorcodide, N-phenethyl-7α-(N-methylphenethylcarbamoyl)-6,14-endoethenotetrahydronororipavine, N-phenethyl-7β-(N-methylphenethylcarbamoyl)- 6,14-endoethenotetrahydronororipavine, N-phenethyl-7α-(N-methylphenethylcarbamoyl)-6,14-endoethanotetrahydronororipavine, N-phenethyl-7β-(N-methylphenethylcarbamoyl)-6,14-endoethanotetrahydronororipavine, N-phenethyl-7α-(N-methylphenethylcarbamoyl)-6,14-endoethenotetrahydronorthebaine, N-phenethyl-7β-(N-methylphenethylcarbamoyl)-6,14-endoethenotetrahydronorthebaine, N-phenethyl-7α-(N-methylphenethylcarbamoyl)-6,14-endoethanotetrahydronorthebaine, N-phenethyl-7β-(N-methylphenethylcarbamoyl)-6,14-endoethanotetrahydronorthebaine, N-phenethyl-7α-(N-allylmethylcarbamoyl)-6,14- endoethenotetrahydronormorphide, N-phenethyl-7β-(N-allylmethylcarbamoyl)-6,14-endoethenotetrahydronormorphide, N-phenethyl-7α-(N-allylmethylcarbamoyl)-6,14-endoethanotetrahydronormorphide, N-phenethyl-7β-(N-allylmethylcarbamoyl)-6,14-endoethanotetrahydronormorphide, N-phenethyl-7α-(N-allylmethylcarbamoyl)-6,14-endoethenotetrahydronorcodide, N-phenethyl-7β-(N-allylmethylcarbamoyl)-6,14-endoethenotetrahydronorcodide, N-phenethyl-7α-(N-allylmethylcarbamoyl)-6,14-endoethanotetrahydronorcodide, N-phenethyl-7β-(N-allylmethylcarbamoyl)-6,14-endoethanotetrahydronorcodide, N-phenethyl-7α-(N-allylmethylcarbamoyl)-6,14-endoethenotetrahydronororipavine, N-phenethyl-7β-(N-allylmethylcarbamoyl)-6,14-endoethenotetrahydronororipavine, N-phenethyl-7α-(N-allylmethylcarbamoyl)-6,14-endoethanotetrahydronororipavine, N-phenethyl-7β-(N-allylmethylcarbamoyl)-6,14-endoethanotetrahydronororipavine, N-phenethyl-7α-(N-allylmethylcarbamoyl)-6,14-endoethenotetrahydronorthebaine, N-phenethyl-7β-(N-allylmethylcarbamoyl)-6,14-endoethenotetrahydronorthebaine, N-phenethyl-7α-(N-allylmethylcarbamoyl)-6,14-endoethanotetrahydronorthebaine and N-phenethyl-7β-(N-allylmethylcarbamoyl)-6,14-endoethanotetrahydronorthebaine, although the compounds according to the present invention are not restricted to these compounds.

The compounds represented by formula (I) may be obtained concretely by the following methods.

Among the compounds represented by formula (I), those in which A is —X(=O)—NR$^6$— (wherein X and R$^6$ represent the same meanings as described above) may be obtained concretely by the following methods.

In general, the compounds represented by the formula (Ia) (wherein B, R$^5$, R$^6$ and R$^8$ represent the same meanings as described above) may be prepared by the method by Bentley et al., (J. Am. Chem. Soc. 89, 3265 (1967), Japanese Patent Publication (Kokai) No. 44-23095).

A compound (Ia) may also be obtained by carrying out Diels-Alder reaction of a compound (II) with a compound (III). In this case, 7α isomer and 7β isomer may be separated and purified by column chromatography. In cases where Diels-Alder reaction is carried out, as the reaction solvent, aromatic hydrocarbon solvents such as benzene, toluene, xylene or dichlorobenzene, as well as ether solvents such as THF, ether, DME or dioxane, or halogen-containing solvents such as dichloroethane may be used. Among these, aromatic hydrocarbon solvents, especially xylene or dichlorobenzene, are preferred. In cases where the amide (III) which is a dienophile is dissolved on heating, the amide (III) may be used as both a dienophile and a solvent. Although the reaction may be carried out at 50 to 300° C., preferably 100 to 200° C., satisfactory results may usually be obtained under the refluxing condition of xylene (about 140° C.) or dichlorobenzene (about 180° C.). Although the reaction time is not restricted and may be appropriately selected depending on the reaction temperature, the reaction time may usually be 5 hours to 10 days, preferably 5 hours to 2 days. The amide (III) may be used in an amount of 1 to 30 equivalents, preferably 1 to 10 equivalents, unless it is used as the reaction solvent.

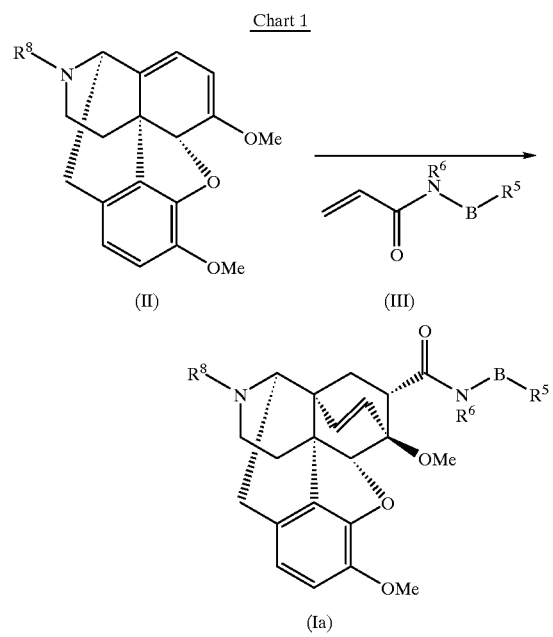

Chart 1

In general, as shown in Chart 2, a compound (Ib) or a compound (Ic) may be obtained by the selective demethylation of the compound (Ia). That is, the compound (Ib) may be obtained by demethylating the compound (Ia) with 2 to 10 times by mole of boron tribromide. In this reaction, as the reaction solvent, halogen-containing solvents such as chloroform or dichloromethane may preferably be used. The reaction may be carried out at −80° C. to room temperature, and satisfactory results may usually be obtained at 0° C. The reaction time is not restricted and may be appropriately selected depending on the reaction temperature. Usually, the reaction time may be about 5 minutes to 10 hours, preferably about 5 minutes to 3 hours. In place of the boron tribromide, boron tribromide dimethylsulfide complex, 9-bromo-9-borabicyclo[3.3.0]nonane(9-Br-BBN), or dimethylboron bromide may be employed. In this case, the reaction may be carried out at a temperature between room temperature and 100° C. Further, in this case, the reaction time is not restricted and may be appropriately selected depending on the reaction temperature. Usually, the reaction time may be about 10 minutes to 50 hours, preferably about 1 hour to 10 hours. On the other hand, compound (Ic) may be obtained by demethylating the compound (Ia) with an alkylmercaptane such as ethanethiol, propanethiol or butanethiol in the presence of excess Lewis acid such as boron trifluoride diethyl ether complex. The Lewis acid may be used in an amount of 3 to 50 equivalents, preferably 3 to 20 equivalents, and the alkylmercaptane may be used in an amount of 10 to 100 equivalents, preferably 10 to 30 equivalents. As the reaction solvent, halogen-containing solvents such as chloroform or dichloromethane may preferably be used. The reaction may be carried out at a temperature between room temperature and 100° C., and satisfactory results may usually be obtained at room temperature. The reaction time is not restricted and may be appropriately selected depending on the reaction temperature. Usually, the reaction time may be about 12 hours to 20 days, preferably about 1 day to 10 days.

Chart 2

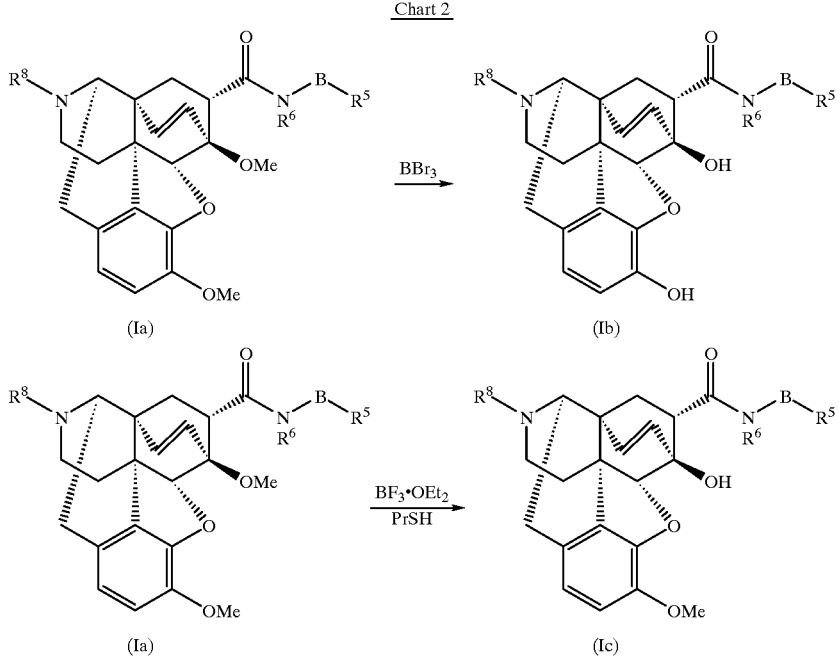

Among the compounds represented by the formula (I), those in which A is —NR⁶—X(=O)— (wherein X and R⁶ represent the same meanings as described above), may be obtained concretely by the following method.

In general, as shown in Chart 3, a compound (IVb) (wherein $R^6$ is $C_1$–$C_5$ alkyl, $C_3$–$C_7$ alkenyl or $C_7$–$C_{13}$ aralkyl) may be obtained by condensing the compound (IVa) obtained by the method by Bentley et al., (J. Chem. Soc. (C), 2235 (1969)) and an acid chloride (V) (wherein $R^7$ is $C_2$–$C_4$ alkyl, $C_2$–$C_6$ alkenyl, $C_6$–$C_{12}$ aryl or $C_7$–$C_{12}$ aralkyl) in the presence of a base such as triethylamine, and then reducing the resultant with a reducing agent such as lithium aluminum hydride. In the condensation reaction, as the solvent, halogen-containing solvents such as chloroform or dichloromethane; ether solvents such as ether, THF, DME or dioxane; pyridine; or water, as well as mixtures thereof may be employed. Among these, chloroform or THF-water mixed solvent are preferred. As the base, tertiary amines such as triethylamine or diisopropylethylamine; organic bases such as pyridine, dimethylaminopyridine or imidazole; and inorganic bases such as potassium carbonate, sodium carbonate, sodium hydrogen carbonate, sodium hydroxide or potassium hydroxide may be employed. Among these, triethylamine, potassium carbonate, sodium carbonate or sodium hydrogen carbonate may preferably be used in an amount of 1 to 20 equivalents, preferably 1 to 5 equivalents. The acid chloride (V) may preferably be used in an amount of 1 to 20 equivalents, more preferably 1 to 5 equivalents. The reaction may be carried out at −80° C. to 100° C., and preferable results may be obtained at about 0° C. to room temperature. The reaction time is not restricted and may be appropriately selected depending on the reaction temperature. Usually, the reaction time may be about 5 minutes to 30 hours, preferably about 5 minutes to 10 hours.

In the reduction reaction, ether solvents such as ether, THF, DME or dioxane may preferably be used. As the reducing agent, lithium aluminum hydride, diisobutyl aluminum hydride, borane or the like may be employed. The amount of the reducing agent may preferably be 1 to 30 equivalents, more preferably 1 to 10 equivalents. The reaction may be carried out at −80° C. to 100° C., and preferable results may be obtained at 0° C. to room temperature. The reaction time is not restricted and may be appropriately selected depending on the reaction temperature. The reaction time may usually be about 0.5 to 30 hours, preferably about 0.5 to 10 hours.

Chart 3

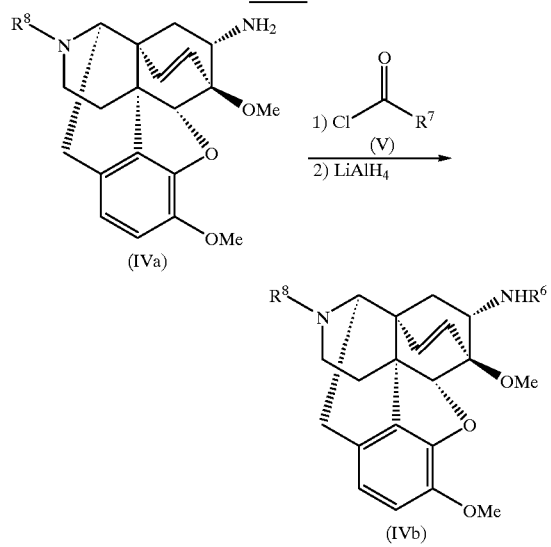

Thereafter, the compound (Id) may be obtained by condensing the compound (IVb) with an acid chloride (VI) (wherein B and $R^5$ represent the same meanings as described above), as shown in Chart 4. As the reaction solvent, halogen-containing solvents such as chloroform or dichloromethane; ether solvents such as ether, THF, DME or dioxane; pyridine; or water, as well as mixture thereof may be employed. Among these, chloroform or THF-water mixed solvent are preferred. As the base, tertiary amines such as triethylamine or diisopropylethylamine; organic bases such as pyridine, dimethylaminopyridine and imidazole; and inorganic bases such as potassium carbonate, sodium carbonate, sodium hydrogen carbonate, sodium hydroxide or potassium hydroxide may be employed. Among these, triethylamine, potassium carbonate, sodium carbonate or sodium hydrogen carbonate may preferably be used in an amount of 1 to 20 equivalents, preferably 1 to 5 equivalents. The acid chloride (VI) may preferably be used in an amount of 1 to 20 equivalents, more preferably 1 to 5 equivalents. The reaction may be carried out at −80° C. to 100° C., and preferable results may be obtained at about 0° C. to room temperature. The reaction time is not restricted and may be appropriately selected depending on the reaction temperature. Usually, the reaction time may be about 5 minutes to 30 hours, preferably about 5 minutes to 10 hours. In this case, by using sulfonyl chloride in place of the acid chloride (VI), 7α-sulfonylamino compound may be obtained.

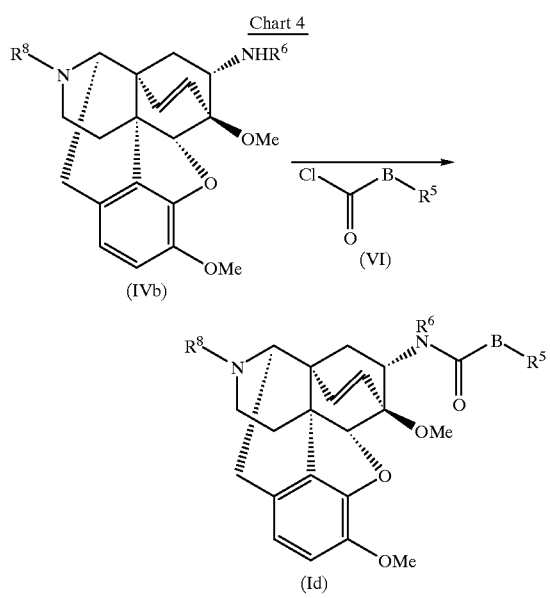

A compound (Ie) may be obtained by condensing a compound (IVc) with the acid chloride (VI), and hydrolyzing the product with a base such as potassium carbonate, as shown in Chart 5. The condensation reaction may be carried out in the same manner as in the reaction shown in Chart 4. In cases where the reactant has a phenolic hydroxyl group as the compound (IVc), if the condensation reaction is carried out in the same manner as in the reaction shown in Chart 4, the phenolic hydroxyl group may also be reacted, so that the desired product (Ie) may be obtained by hydrolyzing the reaction product by alkali treatment. As the reaction solvent used for the alkali treatment, water; alcohol solvents such as methanol or ethanol; or ether solvents such as ether, THF, DME or dioxane; as well as mixtures thereof may be used. If the desired solubility is not attained, a halogen-containing solvent such as chloroform or dichloromethane may be added appropriately. As the base, inorganic bases such as potassium carbonate, sodium carbonate, sodium hydrogen carbonate, sodium hydroxide or potassium hydroxide may be used. Usually, potassium carbonate or sodium hydroxide may be used in an amount of 1 to 20 equivalents, preferably 1 to 10 equivalents. The reaction may be carried out at −80° C. to 100° C., and preferable results may be obtained at 0 to 50° C. The reaction time is not restricted, and may be appropriately selected depending on the reaction temperature. Usually, the reaction time may be about 10 minutes to 10 hours, preferably about 10 minutes to 3 hours. Before the alkali treatment, purification of the condensation product is not necessary.

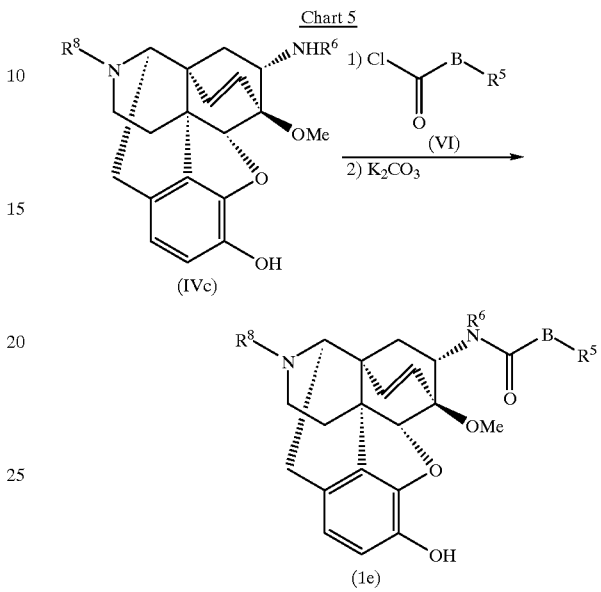

In general, a compound (If) or compound (Ig) may be obtained by selectively demethylating the compound (Id), as shown in Chart 6. That is, a compound (If) may be obtained by demethylating the compound (Id) with 2 to 10 times by mole of boron tribromide. In this reaction, as the reaction solvent, halogen-containing solvents such as chloroform or dichloromethane may preferably be used. The reaction may be carried out at −80° C. to room temperature, and satisfactory results may usually be obtained at 0° C. The reaction time is not restricted and may be appropriately selected depending on the reaction temperature. Usually, the reaction time may be about 5 minutes to 10 hours, preferably about 5 minutes to 3 hours. In place of the boron tribromide, boron tribromide dimethylsulfide complex, 9-bromo-9-borabicyclo[3.3.0]nonane(9-Br-BBN), or dimethylboron bromide may be employed. In this case, the reaction may be carried out at a temperature between room temperature and 100° C. Further, in this case, the reaction time is not restricted and may be appropriately selected depending on the reaction temperature. Usually, the reaction time may be about 10 minutes to 50 hours, preferably about 1 hour to 10 hours. On the other hand, compound (Ig) may be obtained by demethylating the compound (Id) with excess alkylmercaptane such as ethanethiol, propanethiol or butanethiol in the presence of excess Lewis acid such as boron trifluoride diethyl ether complex. The Lewis acid may be used in an amount of 3 to 50 equivalents, preferably 3 to 20 equivalents, and the alkylmercaptane may be used in an amount of 10 to 100 equivalents, preferably 10 to 30 equivalents. As the reaction solvent, halogen-containing solvents such as chloroform or dichloromethane may preferably be used. The reaction may be carried out at a temperature between room temperature and 100° C., and satisfactory results may usually be obtained at room temperature. The reaction time is not restricted and may be appropriately selected depending on the reaction temperature. Usually, the reaction time may be about 12 hours to 20 days, preferably about 1 day to 10 days. By the demethylation reaction with boron tribromide, the compound (Ie) may be often obtained as a side product in addition to the compound (If). In such a case, both of the compounds (If) and (Ie) may be obtained by column chromatography.

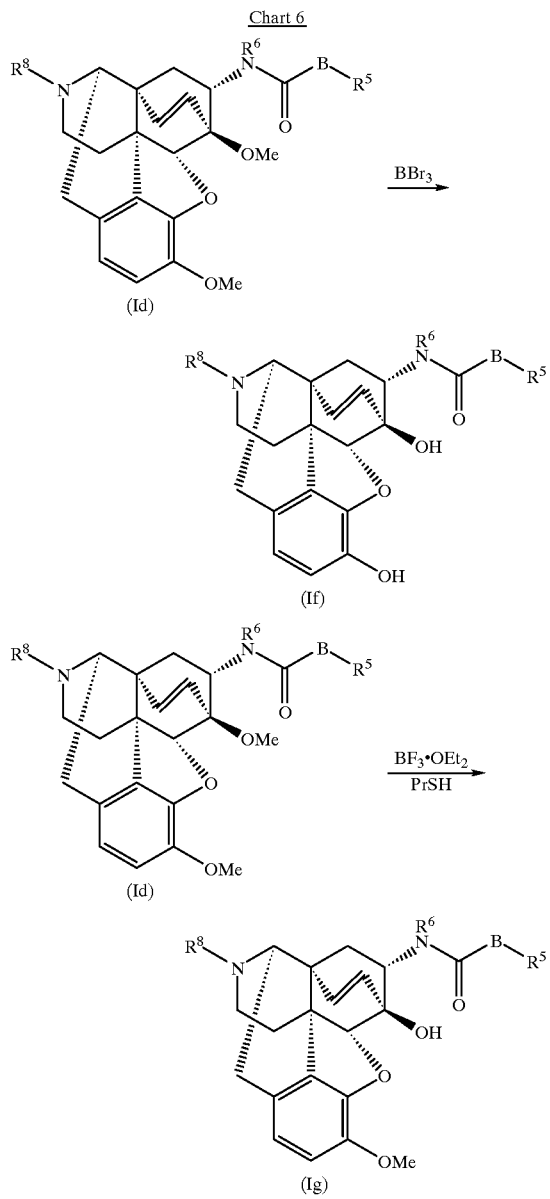

Chart 6

(Id)

(If)

(Id)

(Ig)

In general, as shown in Chart 7, a compound (Ii) may be obtained by hydrogenation of a compound (Ih). As the reaction solvent, alcohol solvents such as methanol or ethanol; ether solvents such as ether, THF, DME or dioxane; aromatic hydrocarbon solvents such as benzene or toluene may be employed. Among these, alcohol solvents, especially methanol or ethanol, are preferred. Examples of the acid to be used include inorganic acids such as hydrochloric acid, hydrobromic acid, sulfuric acid or phosphoric acid; organic sulfonic acids such as methanesulfonic acid or p-toluenesulfonic acid; or organic carboxylic acids such as benzoic acid, acetic acid or oxalic acid. Among these, hydrochloric acid, sulfuric acid, methanesulfonic acid or acetic acid are preferred. As the metal catalyst, any of the catalysts generally used for hydrogenation reactions, including palladium catalysts such as palladium hydroxide or palladium-carbon; platinum catalysts such as platinum oxide or platinum hydroxide; or nickel catalysts such as Raney nickel may be employed. Among these, palladium-carbon or platinum oxide may preferably be used. The reaction may be carried out at $-30°$ C. to $100°$ C., preferably $-10°$ C. to $50°$ C. under a hydrogen gas pressure of 1 to 100 atm, preferably 1 to 30 atm. Usually, preferable results may be obtained at room temperature under normal pressure. The reaction time is not restricted and may be appropriately selected depending on the reaction temperature. Usually, the reaction time may be about 1 hour to 10 days, preferably about 12 hours to 5 days.

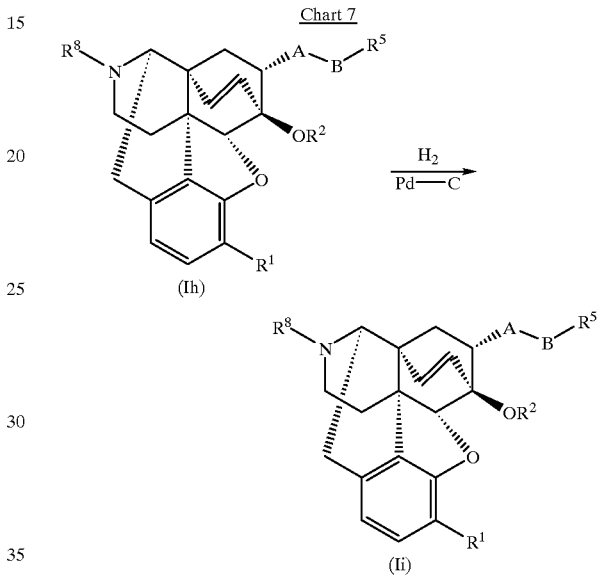

Chart 7

(Ih)

(Ii)

It has been discovered that the compounds represented by the formula (I) according to the present invention have agonist or antagonist activities as the compounds having abilities to bind to opioid ε-receptor as a result of both in vitro and in vivo assays. Opioid ε-receptor agonists are useful as analgesics and may be applicable not only to a pain such as postoperative pain or cancer pain, but also widely to general pains. Opioid ε-receptor antagonists may be used as important tools in the pharmacological studies of this receptor.

In cases where the compound according to the present invention is clinically used, the free base or the salt per se may be administered. Alternatively, the compound may be appropriately mixed with an excipient such as stabilizer, buffer agent, diluent, isotonic agent or antiseptic. Examples of the dosage form include injection; oral preparations such as tablet, capsule, granules, powder or syrup; rectal preparations such as suppository; or topical preparations such as ointment, cream or patch. In cases where the compound according to the present invention is used as a drug, it may contain the effective component described above preferably in an amount of 0.00001 to 50% by weight, more preferably 0.001 to 10% by weight. The dosage may be appropriately selected depending on the symptom, age, body weight and administration method. In case of injection, the effective component may be administered in an amount of 0.01 μg to 1 g per day, and in case of oral preparation, the effective component may be administered in an amount of 0.1 μg to 10 g per day. The drug may be administered in one time or in several times per day.

EXAMPLES

Although the present invention will now be described by way of specific examples thereof, the present invention is not restricted thereto. Unless otherwise specified, reactions were carried out under argon atmosphere. The physical properties of the compounds are shown below in summary.

Example 1
N-cyclopropylmethyl-7α-carbamoyl-6,14-endoethenotetrahydronorthebaine 5

To 2.30 g of N-cyclopropylmethylnorthebaine, 9.38 g of acrylamide was added and the resulting mixture was heated at 100° C. for 12 hours. To this mixture, 10 ml of ethanol and 100 ml of water were added, and the resultant was extracted 3 times with 50 ml each of ethyl acetate. The organic phases were combined and washed with 50 ml of brine. The resultant was dried over anhydrous magnesium sulfate and concentrated. The obtained crude product was purified by silica gel column chromatography to obtain 2.50 g of the captioned compound in a 91% yield.

Reference Example 1
N-cyclopropylmethyl-7α-ethoxycarbonyl-6,14-endoethenotetrahydronorthebaine 6

In 20 ml of ethyl acrylate, 6.66 g of N-cyclopropylmethylnorthebaine was dissolved and the mixture was heated to reflux for 15 hours. After cooling to room temperature, the mixture was concentrated and recrystallized from ethyl acetate solution to obtain 5.88 g of the captioned compound as colorless transparent prism crystals in a 69% yield.

Reference Example 2

The same procedure as in Reference Example 1 was repeated except that 3-O-benzyl-N-cyclopropylmethylnorolipabin was used in place of N-cyclopropylmethylnorthebaine to obtain 3-O-benzyl-N-cyclopropylmethyl-7α-ethoxycarbonyl-6,14-endoethenotetrahydronorolipabin 7 (96%).

Reference Example 3
N-cyclopropylmethyl-7α-carboxyl-6,14-endoethenotetrahydronorthebaine 8.hydrochloric acid salt In 30 ml of 6N hydrochloric acid, 2.02 g of N-cyclopropylmethyl-7α-ethoxycarbonyl-6,14-endoethenotetrahydronorthebaine 6 was dissolved and the mixture was heated to reflux for 7 hours. After cooling to room temperature, the mixture was placed in an ice bath and 20 ml of cold water was added to precipitate crystals. The crude crystals obtained by filtration were recrystallized from methanol solution to obtain 1.56 g of the captioned compound in a 76% yield.

Example 2
N-cyclopropylmethyl-7α-phenylcarbamoyl-6,14-endoethenotetrahydronorthebaine 9

In 10 ml of toluene, 410 mg of N-cyclopropylmethylnorthebaine was dissolved and 266 mg of N-phenylacrylamide was added, followed by heating the mixture to reflux for 100 hours. After cooling to room temperature, 30 ml of water was added and phase-separated, followed by extraction twice with 20 ml each of ethyl acetate. The organic layers were combined and dried over anhydrous magnesium sulfate, followed by concentrating the mixture. The obtained crude product was purified by silica gel column chromatography to obtain 410 mg of the captioned compound as colorless amorphous powder in a 70% yield.

Example 3
N-cyclopropylmethyl-7α-phenylcarbamoyl-6,14-endoethenotetrahydronormorphide 10.methanesulfonic acid salt In 10 ml of dichloromethane, 265 mg of N-cyclopropylmethyl-7α-phenylcarbamoyl-6,14-endoethenotetrahydronorthebaine 9 was dissolved, and 3.2 ml of 1.0 M boron tribromide solution in dichloromethane was added dropwise while cooling the mixture in an ice bath. After completion of the dropping, the ice bath was removed and the mixture was stirred. One hour later, the mixture was again placed in an ice bath and 50 ml of 6% aqueous ammonia was added, followed by vigorously stirring the mixture at room temperature. After confirming that suspended matters are no longer observed, the mixture was phase-separated and extracted twice with 30 ml each of chloroform. The organic layers were combined and dried over anhydrous magnesium sulfate, followed by concentrating the resultant. The obtained crude crystals were recrystallized from chloroform/methanol solution to obtain 159 mg of free base of the captioned compound as white cotton-like crystals in a 47% yield. The free base of the captioned compound was suspended in methanol, and methanesulfonic acid was added while cooling the mixture in an ice bath to form a salt. Ethyl acetate was added to the solution and the salt was precipitated to obtain 135 mg of methanesulfonic acid salt of the captioned compound.

Example 4
N-cyclopropylmethyl-7α-benzylcarbamoyl-6,14-endoethenotetrahydronorthebaine 11

In 10 ml of chloroform, 300 mg of N-cyclopropylmethyl-7α-carboxyl-6,14-endoethenotetrahydronorthebaine 8.hydrochloric acid salt was suspended, and 0.2 ml of oxalyl chloride was added thereto, followed by heating the mixture to reflux for 2 hours. After cooling to room temperature, the resultant was concentrated and the remaining solvent and oxalyl chloride were evaporated off by using a vacuum pump to prepare N-cyclopropylmethyl-7α-chlorocarbonyl-6,14-endoethenotetrahydronorthebaine. To a solution containing 291 mg of benzylamine in 5 ml of chloroform, 0.18 ml of triethylamine was added and a solution containing the prepared N-cyclopropylmethyl-7α-chlorocarbonyl-6,14-endoethenotetrahydronorthebaine in 5 ml of chloroform was added while cooling the mixture in an ice bath. After removing the ice bath, the mixture was stirred for 1 hour and 50 ml of saturated aqueous sodium hydrogen carbonate was added, followed by phase-separation. The resultant was extracted twice with 20 ml each of chloroform and the organic layers were combined. The resultant was dried over anhydrous magnesium sulfate and concentrated, followed by purifying the obtained crude product by silica gel chromatography to obtain 307 mg of the captioned compound as white amorphous powder in a 92% yield.

Examples 5–10

The same procedure as in Example 4 was repeated except that phenethylamine, allylamine, 3-phenylpropylamine, N-allylmethylamine, N-methylphenethylamine and propargylamine were used, respectively, in place of benzylamine to obtain N-cyclopropylmethyl-7α-phenethylcarbamoyl-6,14-endoethenotetrahydronorthebaine 12 (100%), N-cyclopropylmethyl-7α-allylcarbamoyl-6,14-endoethenotetrahydronorthebaine 13 (79%), N-cyclopropylmethyl-7α-(3-phenylpropylcarbamoyl)-6,14-endoethenotetrahydronorthebaine 14 (100%), N-cyclopropylmethyl-7α-(N-allylmethylcarbamoyl)-6,14-

39 endoethenotetrahydronorthebaine 15 (100%), N-cyclopropylmethyl-7α-(N-methylphenethylcarbamoyl)-6,14-endoethenotetrahydronorthebaine 16 (100%), and N-cyclopropylmethyl-7α-propargylcarbamoyl-6,14-endoethenotetrahydronorthebaine 17 (100%), respectively.

Example 11

The same procedure as in Example 3 was repeated except that N-cyclopropylmethyl-7α-benzylcarbamoyl-6,14-endoethenotetrahydronorthebaine 11 was used in place of N-cyclopropylmethyl-7α-phenylcarbamoyl-6,14-endoethenotetrahydronorthebaine 9, and that silica gel column chromatography was used for the purification in place of recrystallization to obtain N-cyclopropylmethyl-7α-benzylcarbamoyl-6,14-endoethenotetrahydronormorphide 18.methanesulfonic acid salt (49%).

Examples 12–17

The same procedure as in Example 11 was repeated except that N-cyclopropylmethyl-7α-phenethylcarbamoyl-6,14-endoethenotetrahydronorthebaine 12, N-cyclopropylmethyl-7α-allylcarbamoyl-6,14-endoethenotetrahydronorthebaine 13, N-cyclopropylmethyl-7α-(3-phenylpropylcarbamoyl)-6,14-endoethenotetrahydronorthebaine 14, N-cyclopropylmethyl-7α-(N-allylmethylcarbamoyl)-6,14-endoethenotetrahydronorthebaine 15, N-cyclopropylmethyl-7α-(N-methylphenethylcarbamoyl)-6,14-endoethenotetrahydronorthebaine 16, and N-cyclopropylmethyl-7α-propargylcarbamoyl-6,14-endoethenotetrahydronorthebaine 17 were used, respectively, in place of N-cyclopropylmethyl-7α-benzylcarbamoyl-6,14-endoethenotetrahydronorthebaine 11, to obtain N-cyclopropylmethyl-7α-phenethylcarbamoyl-6,14-endoethenotetrahydronormorphide 1.methanesulfonic acid salt (69%), N-cyclopropylmethyl-7α-allylcarbamoyl-6,14-endoethenotetrahydronormorphide 19.methanesulfonic acid salt (66%), N-cyclopropylmethyl-7α-(3-phenylpropylcarbamoyl)-6,14-endoethenotetrahydronormorphide 20.methanesulfonic acid salt (58%), N-cyclopropylmethyl-7α-(N-allylmethylcarbamoyl)-6,14-endoethenotetrahydronormorphide 21.methanesulfonic acid salt (61%), N-cyclopropylmethyl-7α-(N-methylphenethylcarbamoyl)-6,14-endoethenotetrahydronormorphide 22.methanesulfonic acid salt (76%), and N-cyclopropylmethyl-7α-propargylcarbamoyl-6,14-endoethenotetrahydronormorphide 23.methanesulfonic acid salt (56%), respectively.

Example 18

N-cyclopropylmethyl-7α-decylcarbamoyl-6,14-endoethenotetrahydronorthebaine was synthesized following the method of Example 2 except that N-decylacrylamide was used in place of N-phenylacrylamide and that xylene was used in place of toluene, with a reaction time of 24 hours. Without isolating the obtained product, the same procedure as in Example 11 was repeated except that the crudely purified N-cyclopropylmethyl-7α-decylcarbamoyl-6,14-endoethenotetrahydronorthebaine was used in place of N-cyclopropylmethyl-7α-benzylcarbamoyl-6,14-endoethenotetrahydronorthebaine 11 to obtain N-cyclopropylmethyl-7α-decylcarbamoyl-6,14-endoethenotetrahydronormorphide 24.methanesulfonic acid salt (37%).

40

Examples 19–22

The same procedure as in Example 18 was repeated except that N-(4-phenylbutyl)acrylamide, N-(10-phenyldecyl)acrylamide and N-phenethylacrylamide were used, respectively, in place of N-decylacrylamide to obtain N-cyclopropylmethyl-7α-(4-phenylbutylcarbamoyl)-6,14-endoethenotetrahydronormorphide 25.methanesulfonic acid salt (39%), N-cyclopropylmethyl-7β-(4-phenylbutylcarbamoyl)-6,14-endoethenotetrahydronormorphide 26.methanesulfonic acid salt (5%), N-cyclopropylmethyl-7α-(10-phenyldecylcarbamoyl)-6,14-endoethenotetrahydronormorphide 27.methanesulfonic acid salt (21%), and N-cyclopropylmethyl-7β-phenethylcarbamoyl-6,14-endoethenotetrahydronormorphide 28.methanesulfonic acid salt (3%), respectively.

Example 23

N-clopropylmethyl-7α-phenylcarbamoyl-6,14-endoethenotetrahydronorolipabin 29.methanesulfonic acid salt In 30 ml of xylene, 825 mg of 3-O-benzyl-N-cyclopropylmethylnorolipabin was dissolved and 563 mg of N-phenylacrylamide was added thereto, followed by heating the mixture to reflux for 20 hours. After cooling to room temperature, 50 ml of water was added and phases were separated. The resultant was extracted 3 times with 30 ml each of ethyl acetate. The organic layers were combined and dried over anhydrous magnesium sulfate, followed by concentrating the resultant. The obtained crude product was purified by silica gel column chromatography, and 507 mg of the thus obtained crudely purified product was dissolved in 14 ml of acetic acid and 7.5 ml of concentrated hydrochloric acid, followed by heating the obtained mixture at 80° C. Four hours later, heating was stopped and the mixture was cooled to room temperature, followed by evaporation of the solvent under reduced pressure. To the resultant, 50 ml of 14% aqueous ammonia was added and the mixture was extracted 3 times with 30 ml each of diethyl ether. The organic layers were combined and dried over anhydrous magnesium sulfate, followed by concentrating the resultant. The obtained crude product was purified by silica gel column chromatography to obtain 244 mg of the free base of the captioned compound in a 52% two-step yield, and then 238 mg of the methanesulfonic acid salt of the captioned compound.

Example 24

N-cyclopropylmethyl-7α-phenylcarbamoyl- 6,14-endoethanotetrahydronorolipabin 30.methanesulfonic acid salt In 30 ml of xylene, 825 mg of 3-O-benzyl-N-cyclopropylmethylnorolipabin was dissolved and 563 mg of N-phenylacrylamide was added thereto, followed by heating the mixture to reflux for 20 hours. After cooling to room temperature, 50 ml of water was added and phases were separated. The resultant was extracted 3 times with 30 ml each of ethyl acetate and organic layers were combined. The resultant was dried over anhydrous magnesium sulfate and concentrated. The obtained crude product was crudely purified by silica gel chromatography and 495 mg of the obtained crude product was dissolved in methanol, followed by addition of 0.2 ml of methanesulfonic acid. To the resultant, 100 mg of 10% palladium-carbon (50% wet) was added and the atmosphere was replaced with hydrogen, followed by stirring the resultant at room temperature for 4 hours. The mixture was then filtered through celite and the filtrate was concentrated, followed by dissolving the product in a small amount of methanol. To the resultant, 50 ml of saturated aqueous sodium hydrogen carbonate was added and the mixture was extracted 3 times with 30 ml each of ethyl acetate. The organic layers were combined and dried over anhydrous magnesium sulfate, followed by concentrating the resultant. The obtained crude product was purified by silica gel column chromatography to obtain 180 mg of the free base of the captioned compound in a 39% two-step yield, and then 160 mg of the methanesulfonic acid salt of the captioned compound.

Example 25
N-cyclopropylmethyl-7α-hydrazinocarbonyl-6,14-endoethenotetrahydronorthebaine 31

In 10 ml of 2-ethoxyethanol, 870 mg of N-cyclopropylmethyl-7α-ethoxycarbonyl-6,14-endoethenotetrahydronorthebaine 6 was dissolved and 10 ml of hydrazine monohydrate was added thereto, followed by heating the mixture to reflux for 30 hours. After allowing the mixture to cool, 100 ml of water was added and the mixture was extracted 3 times with 50 ml each of ethyl acetate. The organic layers were combined and dried over anhydrous magnesium sulfate, followed by concentrating the resultant. The obtained crude product was purified by silica gel column chromatography to obtain 763 mg of the captioned compound as colorless amorphous powder in 91% a yield.

Example 26

The same procedure as in Example 25 was repeated except that 3-O-benzyl-N-cyclopropylmethyl-7α-ethoxycarbonyl-6,14-endoethenotetrahydronorolipabin 7 was used in place of N-cyclopropylmethyl-7α-ethoxycarbonyl-6,14-endoethenotetrahydronorthebaine 6 to obtain 3-O-benzyl-N-cyclopropylmethyl-7α-hydrazinocarbonyl-6,14-endoethenotetrahydronorolipabin 32 (81%).

Example 27
N-cyclopropylmethyl-7α-benzyloxycarbonylamino-6,14-endoethenotetrahydronorthebaine 33.hydrochloric acid salt In 10 ml of 6N hydrochloric acid, 752 mg of N-cyclopropylmethyl-7α-hydrazinocarbonyl-6,14-endoethenotetrahydronorthebaine 31 was dissolved and 15 ml of diethyl ether was added thereto, followed by slowly adding dropwise 200 mg of aqueous sodium nitrite under vigorous stirring while cooling the mixture in an ice bath. Thirty minutes later, sodium hydrogen carbonate was added and the resultant was extracted twice with 30 ml each of diethyl ether. The organic layers were combined and dried over anhydrous magnesium sulfate. To the resultant, 5 ml of benzyl alcohol was added and diethyl ether was evaporated, followed by heating the remaining benzyl alcohol solution to reflux for 1 hour. After cooling to room temperature, 30 ml of water was added and the mixture was extracted 3 times with 30 ml each of ethyl acetate. The organic layers were combined and dried over anhydrous magnesium sulfate, followed by concentrating the resultant. The obtained crude product was purified by silica gel column chromatography, and the obtained product was suspended in methanol. The product was then converted to a salt with hydrochloric acid/methanol while cooling the mixture in an ice bath to obtain 696 mg of hydrochloric acid salt of the captioned compound as a pale yellow amorphous powder in a 72% yield.

Example 28

The same procedure as in Example 27 was repeated except that 3-O-benzyl-N-cyclopropylmethyl-7α-hydrazinocarbonyl-6,14-endoethenotetrahydronorolipabin 32 was used in place of N-cyclopropylmethyl-7α-hydrazinocarbonyl-6,14-endoethenotetrahydronorthebaine 31 to obtain 3-O-benzyl-N-cyclopropylmethyl-7α-benzyloxycarbonylamino-6,14-endoethenotetrahydronorolipabin 34 (89%).

Reference Example 4
N-cyclopropylmethyl-7α-amino-6,14-endoethenotetrahydronorthebaine 35

In 15 ml of acetic acid and 7.5 ml of concentrated hydrochloric acid, 300 mg of N-cyclopropylmethyl-7α-benzyloxycarbonylamino-6,14-endoethenotetrahydronorthebaine 33.hydrochloric acid salt was dissolved and the mixture was heated at 80° C. for 1 hour. After cooling to room temperature, the mixture was concentrated and 50 ml of 14% aqueous ammonia was added thereto, followed by extraction of the mixture 3 times with 30 ml each of ethyl acetate. The organic layers were combined and dried over anhydrous magnesium sulfate, followed by concentrating the resultant. The obtained crude product was purified by silica gel column chromatography to obtain 171 mg of the captioned compound in a 82% yield.

Reference Examples 5–6

The same procedure as in Reference Example 4 was repeated except that 3-O-benzyl-N-cyclopropylmethyl-7α-benzyloxycarbonylamino-6,14-endoethenotetrahydronorolipabin 34 was used in place of N-cyclopropylmethyl-7α-benzyloxycarbonylamino-6,14-endoethenotetrahydronorthebaine 33.hydrochloric acid salt to obtain N-cyclopropylmethyl-7α-amino-6,14-endoethenotetrahydronorolipabin 36 (73%) and N-cyclopropylmethyl-7β-amino-6,14-endoethenotetrahydronorolipabin 37 (11%).

Example 29
N-cyclopropylmethyl-7α-benzoylamino-6,14-endoethenotetrahydronorthebaine 38

In 10 ml of dichloromethane, 148 mg of N-cyclopropylmethyl-7α-amino-6,14-endoethenotetrahydronorthebaine 35.hydrochloric acid salt was suspended and 0.08 ml of triethylamine was added thereto, followed by adding to the mixture 0.046 ml of benzoyl chloride while cooling the mixture in an ice bath. After stirring the mixture at room temperature for 1 hour, 30 ml of water was added and phases were separated. The resultant was extracted twice with 10 ml each of dichloromethane. The organic layers were combined and dried over anhydrous magnesium sulfate, followed by concentrating the resultant. The obtained crude product was purified by silica gel column chromatography to quantitatively obtain 187 mg of the captioned compound.

Example 30

The same procedure as in Example 29 was repeated except that cinnamoyl chloride was used in place of benzoyl chloride to obtain N-cyclopropylmethyl-7α-cinnamoylamino-6,14-endoethenotetrahydronorthebaine 39 (96%).

Example 31
N-cyclopropylmethyl-7α-(5-phenylvalerylamino)-6,14-endoethenotetrahydronorthebaine 40

In 10 ml of dichloromethane, 180 mg of 5-phenyl valeric acid was suspended and 0.26 ml of oxalyl chloride was added dropwise while cooling the mixture in an ice bath.

After stirring the mixture at room temperature for 1 hour, the mixture was concentrated and the remaining solvent and oxalyl chloride were evaporated off by using a vacuum pump to prepare 5-phenylvaleryl chloride. In 10 ml of dichloromethane, 190 mg of N-cyclopropylmethyl-7α-amino-6,14-endoethenotetrahydronorthebaine 35.hydrochloric acid salt was suspended and 0.4 ml of triethylamine was added thereto, followed by adding 10 ml of dichloromethane solution of the prepared 5-phenylvaleryl chloride while cooling the mixture in an ice bath. After stirring the mixture at room temperature for 1 hour, 50 ml of water was added and the phases were separated. The resultant was extracted twice with 30 ml each of ethyl acetate. The organic layers were combined and dried over anhydrous magnesium sulfate, and the resultant was concentrated. The obtained crude product was purified by silica gel column chromatography to obtain 154 mg of the captioned compound in a 58% yield.

Examples 32–34

The same procedure as in Example 31 was repeated except that 4-phenylbenzoic acid, 5-phenyl-2,4-pentadienoic acid and 3-phenylpropionic acid were used, respectively, in place of 5-phenylvaleric acid to obtain N-cyclopropylmethyl-7α-(4-phenylbenzoylamino)-6,14-endoethenotetrahydronorthebaine 41 (88%), N-cyclopropylmethyl-7α-(5-phenyl-2,4-bentadienoylamino)-6,14-endoethenotetrahydronorthebaine 42 (94%) and N-cyclopropylmethyl-7α-(3-phenylpropionylamino)-6,14-endoethenotetrahydronorthebaine 43 (84%), respectively.

Examples 35–40

The same procedure as in Example 11 was repeated except that N-cyclopropylmethyl-7α-benzoylamino-6,14-endoethenotetrahydronorthebaine 38, N-cyclopropylmethyl-7α-(5-phenylvalerylamino)-6,14-endoethenotetrahydronorthebaine 40, N-cyclopropylmethyl-7α-(4-phenylbenzoylamino)-6,14-endoethenotetrahydronorthebaine 41, N-cyclopropylmethyl-7α-(5-phenyl-2,4-pentadienoylamino)-6,14-endoethenotetrahydronorthebaine 42 and N-cyclopropylmethyl-7α-(3-phenylpropionylamino)-6,14-endoethenotetrahydronorthebaine 43 were used, respectively, in place of N-cyclopropylmethyl-7α-benzylcarbamoyl-6,14-endoethenotetrahydronorthebaine 11 to obtain N-cyclopropylmethyl-7α-benzoylamino-6,14-endoethenotetrahydronormorphide 44.methanesulfonic acid salt (82%), N-cyclopropylmethyl-7α-(5-phenylvalerylamino)-6,14-endoethenotetrahydronormorphide 45.methanesulfonic acid salt (61%), N-cyclopropylmethyl-7α-(4-phenylbenzoylamino)-6,14-endoethenotetrahydronormorphide 46.methanesulfonic acid salt (33%), N-cyclopropylmethyl-7α-(5-phenyl-2,4-pentadienoylamino)-6,14-endoethenotetrahydronormorphide 47.methanesulfonic acid salt (33%), N-cyclopropylmethyl-7α-(3-phenylpropionylamino)-6,14-endoethenotetrahydronorolipabin 48.methanesulfonic acid salt (50%) and N-cyclopropylmethyl-7α-(3-phenylpropionylamino)-6,14-endoethenotetrahydronormorphide 49.methanesulfonic acid salt (23%), respectively.

Reference Example 7
N-cyclopropylmethyl-7α-(5-phenyl-2,4-pentadienoylamino)-3-O-(5-phenyl-2,4-pentadienoyl)-6,14-endoethenotetrahydronorolipabin 50

In 5 ml of dichloromethane, 0.42 g of 5-phenyl-2,4-pentadienoic acid was suspended. While cooling the suspension in an ice bath, 0.6 ml of oxalyl chloride was added dropwise and the mixture was stirred at room temperature for 1 hour, followed by concentrating the mixture. The remaining solvent and oxalyl chloride were evaporated by using a vacuum pump to prepare 5-phenyl-2,4-pentadienoyl chloride. In 10 ml of dichloromethane, 206 mg of N-cyclopropylmethyl-7α-amino-6,14-endoethenotetrahydronorolipabin 36 was suspended and 0.4 ml of triethylamine was added thereto, followed by adding 5 ml of dichloromethane solution of the prepared 5-phenyl-2,4-pentadienoyl chloride. After stirring the mixture at room temperature for 1 hour, 50 ml of saturated aqueous sodium hydrogen carbonate was added and phases were separated. The resultant was extracted twice with 30 ml each of ethyl acetate. The organic layers were combined and dried over anhydrous magnesium sulfate, followed by concentrating the resultant. The obtained crude product was purified by silica gel column chromatography to obtain 332 mg of the captioned compound in a 89% yield.

Example 41
N-cyclopropylmethyl-7α-(5-phenyl-2,4-pentadienoylamino)-6,14-endoethenotetrahydronorolipabin 51.methanesulfonic acid salt In a mixed solvent of 5 ml of chloroform and 10 ml of methanol, 327 mg of N-cyclopropylmethyl-7α-(5-phenyl-2,4-pentadienoylamino)-3-O-(5-phenyl-2,4-pentadienoyl)-6,14-endoethenotetrahydronorolipabin 50 was dissolved and 83 mg of potassium carbonate was added thereto, followed by stirring the mixture at room temperature for 1.5 hours. To the mixture, 30 ml of saturated aqueous sodium hydrogen carbonate solution was added and phases were separated. The resultant was extracted twice with 20 ml each of ethyl acetate. The organic layers were combined and dried over anhydrous magnesium sulfate, followed by concentrating the resultant. The obtained crude product was purified by silica gel column chromatography to obtain 239 mg of the free base of the captioned compound in a 94% yield and 206 mg of methanesulfonic acid salt of the captioned compound.

Example 42

The same procedure as in Reference Example 7 was repeated except that 5-phenylvaleric acid was used in place of 5-phenyl-2,4-pentadienoic acid and that N-cyclopropylmethyl-7β-amino-6,14-endoethenotetrahydronorolipabin 37 was used in place of N-cyclopropylmethyl-7α-amino-6,14-endoethenotetrahydronorolipabin 36 to obtain N-cyclopropylmethyl-7β-(5-phenylvalerylamino)-3-O-(5-phenylvaleryl)-6,14-endoethenotetrahydronorolipabin. The same procedure as in Example 41 was repeated except that the thus obtained product was used without isolation in place of N-cyclopropylmethyl-7α-(5-phenyl-2,4-pentadienoylamino)-3-O-(5-phenyl-2,4-pentadienoyl)-6,14-endoethenotetrahydronorolipabin 50 to obtain N-cyclopropylmethyl-7β-(5-phenylvalerylamino)-6,14-endoethenotetrahydronorolipabin 52 (79%).

Example 43

The same procedure as in Example 42 was repeated except that N-cyclopropylmethyl-7α-amino-6,14-endoethenotetrahydronorolipabin 36 was used in place of N-cyclopropylmethyl-7β-amino-6,14-endoethenotetrahydronorolipabin 37 to obtain N-cyclopropylmethyl-7α-(5-phenylvalerylamino)-6,14-endoethenotetrahydronorolipabin 53 (87%).

Example 44
N-cyclopropylmethyl-7α-phenylcarbamoyl-6,14-endoethanotetrahydronormorphide 54.phosphoric acid salt In 30 ml of methanol, 343 mg of N-cyclopropylmethyl-7α-phenylcarbamoyl-6,14-endoethenotetrahydronormorphide 10 was suspended and 0.1 ml of methanesulfonic acid was added thereto. To the resultant, 58 mg of 10% palladium-carbon (50% wet) was added and the atmosphere was replaced with hydrogen, followed by stirring the resultant at room temperature for 24 hours. The mixture was then filtered through celite and the filtrate was concentrated. The obtained crude product was purified by Sephadex column chromatography. The methanesulfonic acid salt was converted to phosphoric acid salt to obtain 203 mg of phosphoric acid salt of the captioned compound in a 46% yield.

Examples 45–47

The same procedure as in Example 44 was repeated except that N-cyclopropylmethyl-7α-(3-phenylpropionylamino)-6,14-endoethenotetrahydronormorphide 49, N-cyclopropylmethyl-7α-(3-phenylpropionylamino)-6,14-endoethenotetrahydronorolipabin 48 and N-cyclopropylmethyl-7α-phenethylcarbamoyl-6,14-endoethenotetrahydronormorphide 1 were used, respectively, in place of N-cyclopropylmethyl-7α-phenylcarbamoyl-6,14-endoethenotetrahydronormorphide 10 and that the conversion of the salt was not carried out, to obtain N-cyclopropylmethyl-7α-(3-phenylpropionylamino)-6,14-endoethanotetrahydronormorphide 55.methanesulfonic acid salt (84%), N-cyclopropylmethyl-7α-(3-phenylpropionylamino)-6,14-endoethanotetrahydronorolipabin 3.methanesulfonic acid salt (74%) and N-cyclopropylmethyl-7α-phenethylcarbamoyl-6,14-endoethanotetrahydronorolipabin 56.methanesulfonic acid salt (51%), respectively.

Example 48
N-cyclopropylmethyl-7α-cinnamoylamino-6,14-endoethenotetrahydronorcodide 57

In 5 ml of dichloromethane, 323 mg of N-cyclopropylmethyl-7α-cinnamoylamino-6,14-endoethenotetrahydronorthebaine 39 was dissolved and 1 ml of propanethiol and 0.8 ml of boron trifluoride.diethyl ether complex were added thereto, followed by stirring the mixture at room temperature for 7 days. To the mixture, 30 ml of water was added and the mixture was extracted 3 times with 20 ml each of ethyl acetate. The resultant was dried over anhydrous magnesium sulfate and then concentrated. The obtained crude product was purified by silica gel column chromatography to obtain 169 mg of the captioned compound in a 54% yield.

Example 49

The same procedure as in Example 11 was repeated except that N-cyclopropylmethyl-7α-cinnamoylamino-6,14-endoethenotetrahydronorcodide 57 was used in place of N-cyclopropylmethyl-7α-benzylcarbamoyl-6,14-endoethenotetrahydronorthebaine 11 to obtain N-cyclopropylmethyl-7α-cinnamoylamino-6,14-endoethenotetrahydronormorphide 58.methanesulfonic acid salt (62%).

Example 50

The same procedure as in Example 44 was repeated except that N-cyclopropylmethyl-7α-(N-methylphenethylcarbamoyl)-6,14-endoethenotetrahydronormorphide 22 was used in place of N-cyclopropylmethyl-7α-phenylcarbamoyl-6,14-endoethenotetrahydronormorphide 10 and that the conversion of the salt was not carried out, to obtain N-cyclopropylmethyl-7α-(N-methylphenethylcarbamoyl)-6,14-endoethanotetrahydronormorphide 59.methanesulfonic acid salt (53%).

Reference Example 8

The same procedure as in Reference Example 1 was repeated except that N-phenethylnorthebaine was used in place of N-cyclopropylmethylnorthebaine to obtain N-phenethyl-7α-ethoxycarbonyl-6,14-endoethenotetrahydronorthebaine 60 (64%).

Reference Example 9

The same procedure as in Reference Example 3 was repeated except that N-phenethyl-7α-ethoxycarbonyl-6,14-endoethenotetrahydronorthebaine 60 was used in place of N-cyclopropylmethyl-7α-ethoxycarbonyl-6,14-endoethenotetrahydronorthebaine 6 to obtain N-phenethyl-7α-carboxyl-6,14-endoethenotetrahydronorthebaine 61.hydrochloric acid salt (65%).

Examples 51 and 52

The same procedure as in Example 4 was repeated except that N-phenethyl-7α-carboxyl-6,14-endoethenotetrahydronorthebaine 61.hydrochloric acid salt was used in place of N-cyclopropylmethyl-7α-carboxyl-6,14-endoethenotetrahydronorthebaine 8.hydrochloric acid salt was used and that allylamine and N-methylphenethylamine were used, respectively, in place of benzylamine to obtain N-phenethyl-7α-allylcarbamoyl-6,14-endoethenotetrahydronorthebaine 62 (83%) and N-phenethyl-7α-(N-methylphenethylcarbamoyl)-6,14-endoethenotetrahydronorthebaine 63 (89%), respectively.

Examples 53 and 54

The same procedure as in Example 11 was repeated except that N-phenethyl-7α-allylcarbamoyl-6,14-endoethenotetrahydronorthebaine 62 and N-phenethyl-7α-(N-methylphenethylcarbamoyl)-6,14-endoethenotetrahydronorthebaine 63 were used, respectively, in place of N-cyclopropylmethyl-7α-benzylcarbamoyl-6,14-endoethenotetrahydronorthebaine 11 to obtain N-phenethyl-7α-allylcarbamoyl-6,14-endoethenotetrahydronormorphide 64.methanesulfonic acid salt (76%) and N-phenethyl-7α-(N-methylphenethylcarbamoyl)-6,14-endoethenotetrahydronormorphide 65.methanesulfonic acid salt (60%), respectively.

The physical properties of the compounds obtained in Examples 1–54 and Reference Examples 1–9 are shown in summary in tables.

-continued

| | | |
|---|---|---|
| Compound 8 hydrochloric acid salt Yield 76(%) | NMR (ppm) (300 MHz, DMSO-d6) 0.36–0.48(1H, m), 0.54–0.78(3H, m), 1.07–1.22(1H, m), 1.44(1H, dd, J=6.0, 12.6Hz), 1.97(1H, d, J=12.5Hz), 2.32(1H, dt, J=3.7, 13.9Hz), 2.79–3.26(5H, m), 3.32–3.54(3H, m), 3.46(3H, s), 3.72(3H, s), 4.43(1H, d, J=6.2Hz), 4.94(1H, s), 5.59(1H, d, J=8.8Hz), 5.62(1H, d, J=8.8Hz), 6.60(1H, d, J=8.4Hz), 6.73(1H, d, J=8.1Hz), 9.76(1H, br s), 12.27(1H, br s) | m.p. 180–185(dec) (° C.). Elemental Analysis Chemical Formula Calcd. Found IR (cm$^{-1}$) (KBr) 3596, 3320, 2932, 2666, 2634, 1736, 1702, 1632, 1508, 1475, 1458, 1437, 1292, 1270, 1214, 1195, 1172, 1127, 1104, 1054, 948, 816 Mass (FAB) 424 ((M+H)+) |
| Compound 9 Yield 70(%) | NMR (ppm) (400 MHz, CDCl3) 0.08–0.18(2H, m), 0.46–0.56(2H, m), 0.79–0.90(1H, m), 1.77(1H, dd, J=6.1, 13.4Hz), 1.87(1H, dd, J=2.4, 13.2Hz), 2.05(1H, d, J=5.9, 12.7Hz), 2.33(1H, dd, J=6.6, 12.5Hz), 2.37–2.49(3H, m), 2.69–2.78(2H, m), 3.12(1H, m, J=18.1Hz), 3.19(1H, dd, J=9.8, 13.2Hz), 3.61(1H, d, J=6.4Hz), 3.70(3H, s), 3.83(3H, s), 4.60(1H, s), 5.64(1H, d, J=8.8Hz), 5.96(1H, d, J=8.8Hz), 6.53(1H, d, J=8.3Hz), 6.63(1H, d, J=8.3Hz), 7.07(1H, t, J=7.3Hz), 7.29(2H, t, J=8.1Hz), 7.48(2H, d, J=7.8Hz), 8.19(1H,s) | m.p. (° C.), Elemental Analysis Chemical Formula Calcd. Found IR (cm$^{-1}$) (KBr) 3306, 2926, 1665, 1601, 1547, 1499, 1441, 1311, 1255, 1209, 1166, 1102, 758, 692 Mass (EI) 498 (M+) |
| Compound 10 methanesulfonic acid salt Yield 47(%) | NMR (ppm) (400 MHz, DMSO-d6) 0.39–0.52(2H, m), 0.60–0.78(2H, m), 1.07–1.17(1H, m), 1.64(1H, dd, J=8.5, 17.3Hz), 2.11(1H, br d, J=5.9Hz), 2.33(3.6H, s), 2.76–2.90(2H, m), 2.92–3.11(3H, m), 3.28–3.42(2H, m), 3.48(1H, dd, J=7.1, 13.4Hz), 4.36(1H, s), 4.43(1H, d, J=6.8Hz), 5.54(1H, d, J=8.8Hz), 5.65(1H, d, J=8.8Hz), 5.92(1H, br s), 6.50(1H, d, J=8.3Hz), 6.57(1H, d, J=8.3Hz), 7.05(1H, t, J=7.3Hz), 7.30(2H, t, J=7.8Hz), 7.59(2H, d, J=8.3Hz), 8.41(1H, br s), 9.13(1H, br s), 9.84(1H, s) | m.p. 215(dec) (° C.), Elemental Analysis C.F.* $C_{29}H_{30}N_2O_4 \cdot 0.4H_2O \cdot 1.2MeSO_3H$ Calcd. C, 61.16; H, 6.05; N, 4.72; S, 6.49 Found C, 61.05; H, 6.13; N, 4.84; S, 6.45 IR (cm$^{-1}$) (KBr) 3400, 1678, 1671, 1657, 1601, 1545, 1499, 1446, 1321, 1209, 1195, 1048 Mass (FAB) 471 |

-continued

| | | |
|---|---|---|
| Compound 11 Yield 92(%) 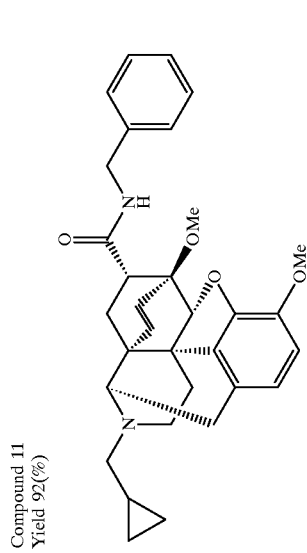 | NMR (ppm) (300 MHz, CDCl3) 0.06–0.19(2H, m), 0.43–0.58(2H, m), 0.76–0.90(1H, m), 1.60(1H, dd, J=6.0, 13.5Hz), 1.84(1H, dd, J=2.2, 12.9Hz), 2.00(1H, dt, J=5.4, 12.6Hz), 2.27–2.48(4H, m), 2.63–2.76(2H, m), 3.11(1H, d, J=19.0Hz), 3.18(1H, dd, J=9.7, 13.3Hz), 3.57(1H, d, J=6.6Hz), 3.61(3H, s), 3.82(3H, s), 4.41(1H, dd, J=5.5, 14.6Hz), 4.46(1H, dd, J=5.5, 14.6Hz), 4.56(1H, d, J=1.1Hz), 5.60(1H, d, J=8.8Hz), 5.90(1H, d, J=8.8Hz), 6.33–6.42(1H, m), 6.52(1H, d, J=8.0Hz), 6.61(1H, d, J=8.2Hz), 7.21–7.35(5H, m) | m.p. (° C.). Elemental Analysis Chemical Formula Calcd. Found IR (cm$^{-1}$) (neat) 3316, 3000, 2934, 2836, 1654, 1534, 1499, 1452, 1284, 1259, 1210, 1167, 1105, 1056, 745, 699 Mass (EI) 512 (M+) |
| Compound 12 Yield 100(%) 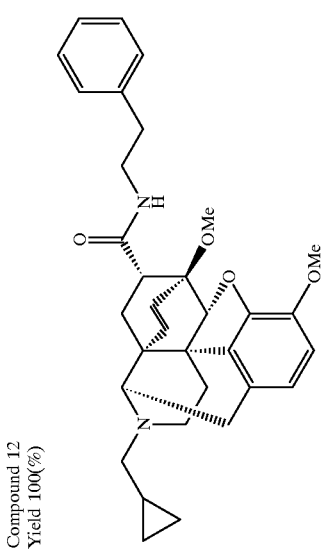 | NMR (ppm) (300 MHz, CDCl3) 0.07–0.18(2H, m), 0.44–0.56(2H, m), 0.77–0.88(1H, m), 1.48(1H, d, J=6.3, 13.2Hz), 1.81(1H, dd, J=2.7, 13.4Hz), 1.97(1H, dt, J=6.1, 12.7Hz), 2.26–2.46(4H, m), 2.59(1H, dd, J=6.3, 9.6Hz), 2.70(1H, dd, J=4.4, 11.8Hz), 2.79(2H, t, J=6.7Hz), 3.09(1H, d, J=18.4Hz), 3.14(1H, dd, J=9.5, 13.3Hz), 3.41–3.58(3H, m), 3.50(3H, s), 3.81(3H, s), 4.52(1H, d, J=1.4Hz), 5.51(1H, m), 5.51(1H, d, J=8.2Hz), 6.62(1H, d, J=8.2Hz), 6.12–6.19(1H, m), 5.55(1H, d, J=8.8Hz), 7.16–7.24(3H, m), 7.26–7.33(2H, m) | m.p. (° C.). Elemental Analysis Chemical Formula Calcd. Found IR (cm$^{-1}$) (KBr) 3312, 3000, 2934, 2836, 1653, 1542, 1499, 1443, 1209, 1104, 750, 700 Mass (EI) 526 (M+) |
| Compound 13 Yield 79(%) 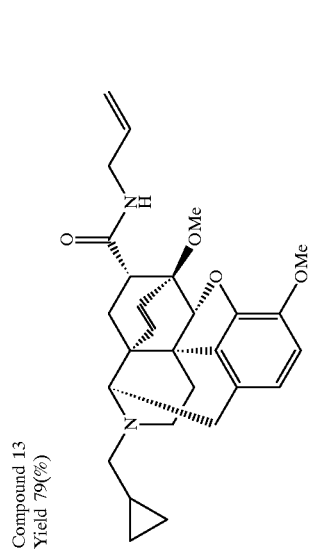 | NMR (ppm) (300 MHz, CDCl3) 0.06–0.18(2H, m), 0.43–0.56(2H, m), 0.78–0.89(1H, m), 1.57(1H, dd, J=6.0, 13.5Hz), 1.80–1.88(1H, m), 2.00(1H, dt, J=5.6, 12.7Hz), 2.27–2.48(4H, m), 2.61–2.75(2H, m), 3.11(1H, d, J=18.1Hz), 3.17(1H, dd, J=9.9, 13.2Hz), 3.57(1H, d, J=6.6Hz), 3.63(3H, s), 3.82(3H, s), 3.84–3.89(2H, m), 4.57(1H, d, J=1.6Hz), 5.10(1H, ddd, J=1.5, 3.0, 10.2Hz), 5.19(1H, ddd, J=1.8, 3.1, 17.3Hz), 5.37(1H, d, J=9.1Hz), 5.75–5.88(1H, m), 5.90(1H, d, J=8.8Hz), 6.14–6.23(1H, m), 6.53(1H, d, J=8.0Hz), 6.62(1H, d, J=8.2Hz) | m.p. (° C.). Elemental Analysis Chemical Formula Calcd. Found IR (cm$^{-1}$) (KBr) 3306, 2930, 2836, 1655, 1543, 1502, 1443, 1285, 1260, 1211, 1103 Mass (EI) 462 (M+) |

-continued

| | | |
|---|---|---|
| Compound 14 Yield 100(%) 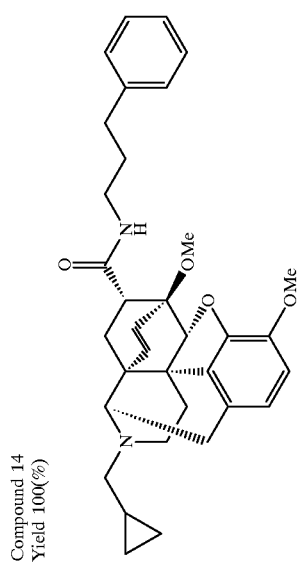 | NMR (ppm) (300 MHz, CDCl3) 0.08–0.17(2H, m), 0.45–0.56(2H, m), 0.76–0.89(1H, m), 1.53(1H, dd, J=6.0, 13.2Hz), 1.74–1.89(3H, m), 2.00(1H, dt, J=5.5, 12.5Hz), 2.28–2.49(4H, m), 2.57–2.75(4H, m), 3.10(1H, d, J=18.1Hz), 3.16(1H, dd, J=9.5, 13.5Hz), 3.26(2H, ddd, J=2.1, 7.0, 12.9Hz), 3.56(1H, d, J=6.3Hz), 3.62(3H, s), 3.82(3H, s), 4.56(1H, d, J=1.4Hz), 5.59(1H, d, J=8.8Hz), 5.89(1H, d, J=8.8Hz), 6.10–6.17(1H, m), 6.52(1H, d, J=8.2Hz), 6.62(1H, d, J=8.2Hz), 7.14–7.22(3H, m), 7.24–7.31(2H, m) | m.p. (° C.), Elemental Analysis Chemical Formula Calcd. Found IR (cm⁻¹) (KBr) 3388, 3314, 2932, 1651, 1545, 1500, 1443, 1285, 1259, 1210, 1104, 700 Mass (EI) 540 (M+) |
| Compound 15 Yield 100(%) 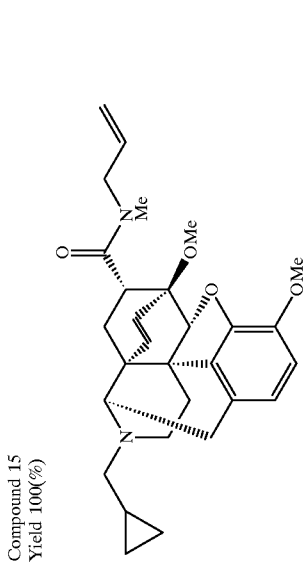 | NMR (ppm) (300 MHz, CDCl3) 0.06–0.18(2H, m), 0.41–0.56(2H, m), 0.73–0.89(1H, m), 1.44–1.60(1H, m), 1.78–2.07(2H, m), 2.26–2.49(4H, m), 2.68(1H, dt, J=4.9, 11.1Hz), 2.84–3.15(3H, m), 2.91(1.5H, s), 3.08(1.5H, s), 3.78(1H, t, J=6.3Hz), 3.62(1.5H, s), 3.63(1.5H, s), 3.82(1.5H, s), 3.83(1.5H, s), 3.82–3.94(1H, m), 4.04–4.15(0.5H, m), 4.29–4.40(0.5H, m), 4.43(0.5H, d, J=1.4Hz), 4.50(0.5H, d, J=1.4Hz), 5.10–5.29(2H, m), 5.55(0.5H, d, J=9.1Hz), 5.56(0.5H, d, J=9.1Hz), 5.65–5.93(1H, m), 6.08(0.5H, dd, J=1.1, 8.8Hz), 6.09(0.5H, dd, J=0.8, 8.8Hz), 6.51(0.5H, d, J=8.2Hz), 6.52(0.5H, d, J=8.2Hz), 6.62(0.5H, d, J=8.0Hz), 6.63(0.5H, d, J=8.0Hz) | m.p. (° C.), Elemental Analysis Chemical Formula Calcd. Found IR (cm⁻¹) (neat) 3080, 2838, 1634, 1504, 1444, 1284, 1261, 1210, 1154, 1104, 1058, 920, 733 Mass (EI) 476 (M+) |
| Compound 16 Yield 100(%) 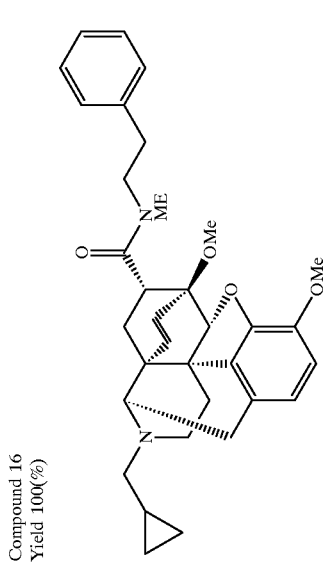 | NMR (ppm) (300 MHz, CDCl3) 0.08–0.20(2H, m), 0.44–0.58(2H, m), 0.75–0.90(1H, m), 1.36(0.5H, dd, J=6.6, 12.4Hz), 1.45(0.5H, dd, J=4.1, 10.2Hz), 1.73–1.81(1H, m), 1.85(0.5H, dd, J=2.5, 12.6Hz), 1.99(0.5H, dt, J=5.2, 12.5Hz), 2.28–2.58(4.5H, m), 2.62–2.74(1.5H, m), 2.82(1H, t, J=7.7Hz), 2.87–3.01(2H, m), 2.94(1.5H, s), 3.04(1.5H, s), 2.83(0.5H, d, J=11.5Hz), 3.11(0.5H, d, J=11.5Hz), 3.45–3.65(2.5H, m), 3.59(1.5H, s), 3.62(1.5H, s), 3.81(1.5H, s), 3.83(1.5H, s), 3.84–3.97(0.5H, m), 4.33(0.5H, d, J=1.4Hz), 4.49(0.5H, d, J=1.4Hz), 5.53(0.5H, d, J=9.1Hz), 5.55(0.5H, d, J=9.1Hz), 6.03(0.5H, d, J=8.8Hz), 6.12(0.5H, d, J=7.1Hz), 6.50(0.5H, d, J=8.5Hz), 6.50(0.5H, d, J=8.0Hz), 6.52(0.5H, d, J=7.1Hz), 6.61(0.5H, d, J=8.2Hz), 6.63(0.5H, d, J=8.2Hz), 7.16–7.34(5H, m) | m.p. (° C.), Elemental Analysis Chemical Formula Calcd. Found IR (cm⁻¹) (neat) 2932, 1637, 1499, 1453, 1284, 1259, 1209, 1167, 1106, 1057, 912, 733 Mass (EI) 540 (M+) |

-continued

| | | |
|---|---|---|
| Compound 17<br>Yield 100(%)<br>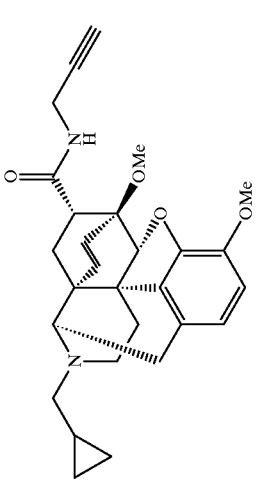 | NMR (ppm) (300 MHz, CDCl3)<br>0.07–0.18(2H, m), 0.44–0.57(2H, m), 0.76–0.90(1H, m), 1.60(1H, dd, J=6.0, 13.2Hz), 1.84(1H, dd, J=2.3, 13.0Hz), 2.00(1H, dt, J=5.6, 12.6Hz), 2.20(1H, t, J=2.6Hz), 2.27–2.48(4H, m), 2.63(1H, dd, J=6.0, 9.6Hz), 2.71(1H, dd, J=4.8, 12.2Hz), 3.05–3.20(2H, m), 3.57(1H, d, J=6.3Hz), 3.64(3H, s), 3.82(3H, s), 4.02(2H, ddd, J=1.8, 2.6, 5.2Hz), 4.555(1H, d, J=1.4Hz), 5.60(1H, d, J=8.8Hz), 5.90(1H, d, J=9.1Hz), 6.36–6.44(1H, m), 6.53(1H, d, J=8.2Hz), 6.63(1H, d, J=8.2Hz) | m.p. (° C.),<br>Elemental Analysis<br>Chemical Formula<br>Calcd.<br>Found<br>IR (cm$^{-1}$) (KBr)<br>3294, 3000, 2936, 2838, 1654, 1543, 1502, 1443, 1284, 1259, 1213, 1168, 1104, 1055, 1021, 946, 772<br>Mass (EI) 460 (M+) |
| Compound 18<br>methanesulfonic acid salt<br>Yield 49(%)<br>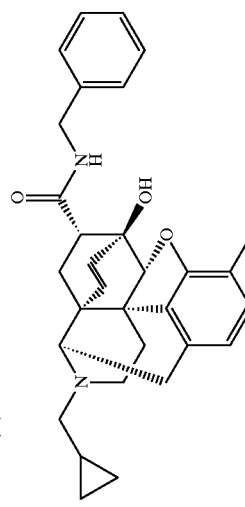 | NMR (ppm) (300 MHz, DMSO-d6)<br>0.37–0.54(2H, m), 0.57–0.77(2H, m), 1.04–1.18(1H, m), 1.56(1H, dd, J=6.2, 12.6Hz), 1.98–2.18(2H, m), 2.33(3H, s), 2.60–2.69(1H, m), 2.76–2.87(1H, m), 2.88–3.10(3H, m), 3.21–3.49(3H, m), 4.19–4.40(4H, m), 5.48(1H, d, J=8.7Hz), 5.65(1H, d, J=8.7Hz), 6.45(1H, d, J=8.1Hz), 6.54(1H, d, J=8.1Hz), 7.17–7.37(5H, m), 8.19(1H, br t, J=5.8Hz), 8.40(1H, br s), 9.13(1H, br s) | m.p. 190(dec) (° C.),<br>Elemental Analysis<br>C.F.* C$_{30}$H$_{32}$N$_2$O$_4$.0.4H$_2$O.MeSO$_3$H<br>Calcd. C, 63.33; H, 6.31; N, 4.76; S, 5.45<br>Found C, 63.18; H, 6.39; N, 4.68; S, 5.75<br>IR (cm$^{-1}$) (KBr)<br>3362, 3068, 2940, 1650, 1547, 1503, 1463, 1210, 1196, 1057, 1048, 781<br>Mass (FAB) 485 ((M+H)+) |
| Compound 1<br>methanesulfonic acid salt<br>Yield 69(%)<br>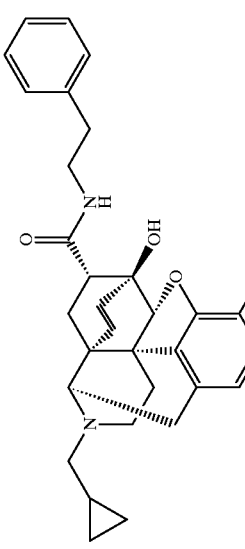 | NMR (ppm) (600 MHz, DMSO-d6)<br>0.40–0.45(1H, m), 0.41–0.42(1H, m), 0.61–0.67(1H, m), 0.70–0.76(1H, m), 1.07–1.15(1H, m), 1.52(1H, dd, J=6.4, 13.5Hz), 2.01–2.13(2H, m), 2.33(3.9H, s), 2.50–2.56(1H, m), 2.66–2.78(3H, m), 2.91–3.06(3H, m), 3.23(1H, dt, J=6.7, 12.8Hz), 3.27–3.40(3H, m), 3.48(1H, quintet, J=6.7Hz), 4.27(1H, s), 4.36(1H, d, J=7.0Hz), 5.46(1H, d, J=8.9Hz), 5.62(1H, d, J=8.9Hz), 5.72(1H, br s), 6.45(1H, d, J=7.9Hz), 6.53(1H, d, J=7.9Hz), 7.18–7.24(3H, m), 7.26–7.52(2H, m), 7.74(1H, br t, J=5.0Hz), 8.36(1H, br s), 9.10(1H, br s) | m.p. 160(dec) (° C.),<br>Elemental Analysis<br>C.F.* C$_{31}$H$_{34}$N$_2$O$_4$.0.2H$_2$O.1.3MeSO$_3$H<br>Calcd. C, 61.86; H, 6.36; N, 4.47; S, 6.65<br>Found C, 61.88; H, 6.56; N, 4.44; S, 6.51<br>IR (cm$^{-1}$) (KBr)<br>3422, 3057, 1657, 1649, 1638, 1562, 1543, 1460, 1323, 1199, 1048, 785, 555<br>Mass (FAB) 499 ((M+H)+) |

-continued

| | | |
|---|---|---|
| Compound 19<br>methanesulfonic acid salt<br>Yield 66(%)<br>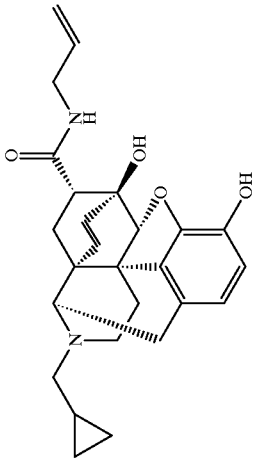 | NMR (ppm) (300 MHz, DMSO-d6)<br>0.36–0.564(2H, m), 0.56–0.77(2H, m), 1.03–1.18(1H, m), 1.53(1H, dd, J=6.1, 12.3Hz), 1.98–2.18(2H, m), 2.34(3.3H, s), 2.55–2.64(1H, m), 2.71–2.85(1H, m), 2.87–3.11(3H, m), 3.20–3.49(3H, m), 3.53–3.80(2H, m), 4.28(1H, s), 4.37(1H, d, J=6.6Hz), 5.04(1H, ddd, J=2.1, 3.9, 10.3Hz), 5.18(1H, ddd, J=2.1, 4.0, 17.2Hz), 5.47(1H, d, J=8.7Hz), 5.62(1H, d, J=8.7Hz), 5.71–5.86(1H, m), 6.45(1H, d, J=8.1Hz), 6.54(1H, d, J=8.1Hz), 7.83(1H, br t, J=5.8Hz), 8.41(1H, br s), 9.13(1H, br s) | m.p. 195(dec) (° C.).<br>Elemental Analysis<br>C.F.* $C_{26}H_{30}N_2O_4$·0.3$H_2O$·0.1MeSO$_3$H<br>Calcd. C, 59.65; H, 6.47; N, 5.13; S, 6.46<br>Found C, 59.70; H, 6.47; N, 5.13; S, 6.32<br>IR (cm$^{-1}$) (KBr)<br>3398, 1657, 1640, 1543, 1502, 1468, 1421, 1323, 1210, 1195, 1060, 1052, 785<br>Mass (FAB) 435 ((M+H)+) |
| Compound 20<br>methanesulfonic acid salt<br>Yield 58(%)<br>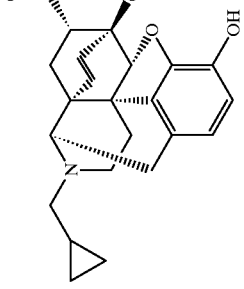 | NMR (ppm) (400 MHz, DMSO-d6)<br>0.38–0.53(2H, m), 0.59–0.77(1H, m), 1.05–1.18(1H, m), 1.55(1H, dd, J=6.6, 12.5Hz), 1.62–1.75(2H, m), 2.00–2.17(2H, m), 2.33(3H, s), 2.52–2.63(3H, m), 2.78(1H, dd, J=9.3, 12.2Hz), 2.90–3.12(5H, m), 3.26–3.52(3H, m), 4.28(1H, s), 4.37(1H, d, J=6.8Hz), 5.46(1H, d, J=8.8Hz), 5.62(1H, d, J=8.8Hz), 5.70(1H, br s), 6.45(1H, d, J=8.3Hz), 6.54(1H, d, J=8.3Hz), 7.13–7.24(3H, m), 7.324–7.32(2H, m), 7.70(1H, br t, J=5.4Hz), 8.37(1H, br s), 9.09(1H, br s) | m.p. 160(dec) (° C.).<br>Elemental Analysis<br>C.F.* $C_{32}H_{36}N_2O_4$·0.5$H_2O$·MeSO$_3$H<br>Calcd. C, 64.16; H, 6.69; N, 4.53; S, 5.19<br>Found C, 64.04; H, 6.84; N, 4.59; S, 5.28<br>IR (cm$^{-1}$) (KBr)<br>3356, 2938, 1645, 1547, 1502, 1461, 1321, 1210, 1195, 1046, 784, 556<br>Mass (FAB) 513 ((M+H)+) |
| Compound 21<br>methanesulfonic acid salt<br>Yield 61(%)<br>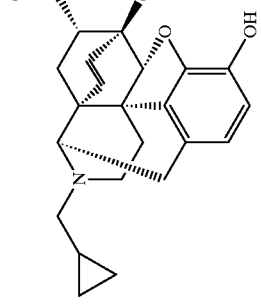 | NMR (ppm) (300 MHz, CDCl3) (data of free salt)<br>0.08–0.24(2H, m), 0.43–0.62(2H, m), 0.74–1.00(1H, m), 1.11–1.31(1H, m), 1.84–2.08(2H, m), 2.29–2.49(4H, m), 2.64–2.70(2H, m), 2.88(1.2H, s), 2.96–3.36(2H, m), 3.03(1.8H, s), 3.51(1H, d, J=6.3Hz), 3.90–4.05(2H, m), 4.41(0.4H, s), 4.45(0.6H, s), 4.65(1H, br s), 5.09–5.33(2H, m), 5.37(1H, d, J=8.5Hz), 5.44(1H, br s), 5.64–5.88(1H, m), 5.89–6.02(1H, m), 6.46(1H, d, J=8.0Hz), 6.61(0.4H, d, J=8.2Hz), 6.62(0.6H, d, J=8.0Hz) | m.p. 175(dec) (° C.).<br>Elemental Analysis<br>C.F.* $C_{27}H_{32}N_2O_4$·0.8$H_2O$·MeSO$_3$H<br>Calcd. C, 60.15; H, 6.78; N, 5.01; S, 5.74<br>Found C, 60.09; H, 6.65; N, 5.06; S, 5.90<br>IR (cm$^{-1}$) (KBr)<br>3424, 3022, 2942, 1627, 1503, 1471, 1418, 1321, 1209, 1195, 1059, 785, 561<br>Mass (FAB) 448 ((M+H)+) |

-continued

| | | |
|---|---|---|
| Compound 22<br>methanesulfonic acid salt<br>Yield 76(%) | 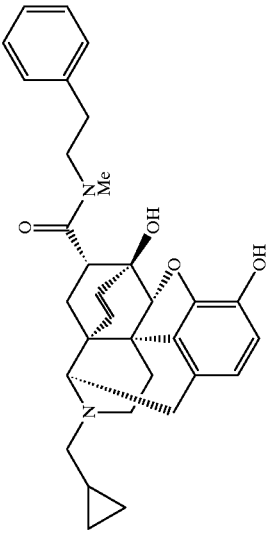 | NMR (ppm) (400 MHz, DMSO-d6)<br>0.4–0.54(2H, m), 0.6–0.68(1H, m), 0.70–0.77(1H, m),<br>1.06–1.15(1H, m), 1.30(0.6H, dd, J=6.4, 12.2Hz), 1.46(0.4H, dd, J=6.4, 12.2Hz), 1.98(0.6H, br d, J=11.7Hz), 2.04(0.4H, br d, J=11.7Hz), 2.18–2.37(1H, m), 2.32(1.8H, s), 2.33(1.2H, s), 2.67–2.78(1H, m), 2.75(1.2H, s), 2.82–3.08(5H, m), 3.05(1.8H, s), 3.12(0.6H, t, J=7.8Hz), 3.26–3.40(2.4H, m), 3.44–3.64(3.6H, m), 3.81–3.89(0.4H, m), 4.33(0.6H, d, J=6.8Hz), 4.36(0.4H, d, J=6.8Hz), 4.43(0.4H, s), 4.46(0.6H, s), 5.40(0.6H, d, J=8.8Hz), 5.43(0.4H, d, J=8.8Hz), 5.64(0.4H, d, J=8.8Hz), 5.70(0.6H, d, J=8.8Hz), 6.45(1H, d, J=8.3Hz), 6.54(0.6H, d, J=8.3Hz), 6.55(0.4H, d, J=8.3Hz), 7.17–7.38(5H, m), 8.36(1H, br s), 9.07(1H, br s) | m.p. 170(dec) (° C.).<br>Elemental Analysis<br>C.F.* $C_{32}H_{36}N_2O_4$·0.7$H_2O$·MeSO$_3$H<br>Calcd. C, 63.79; H, 6.72; N, 4.51; S, 5.16<br>Found C, 63.66; H, 6.79; N, 4.58; S, 5.29<br>IR (cm$^{-1}$) (KBr)<br>3422, 2940, 1629, 1501, 1464, 1414, 1320, 1209, 1194, 1119, 1057, 934, 783<br>Mass (FAB) 513 ((M+H)+) |
| Compound 23<br>methanesulfonic acid salt<br>Yield 56(%) | 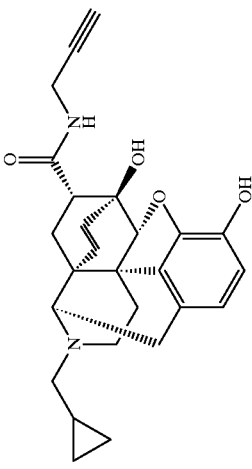 | NMR (ppm) (300 MHz, DMSO-d6)<br>0.36–0.54(2H, m), 0.58–0.78(1H, m), 1.03–1.19(1H, m), 1.52(1H, dd, J=6.3, 12.4Hz), 1.99–2.16(2H, m), 2.33(3H, s), 2.53–2.63(1H, m), 2.72–2.84(1H, m), 2.87–3.13(3H, m), 3.10(1H, t, J=2.5Hz), 3.25–3.55(3H, m), 3.78(1H, ddd, J=2.5, 5.0, 15.6Hz), 3.92(1H, ddd, J=2.5, 5.6, 15.6Hz), 4.26(1H, s), 4.37(1H, d, J=6.9Hz), 5.48(1H, d, J=8.5Hz), 5.62(1H, d, J=8.5Hz), 6.46(1H, d, J=8.2Hz), 6.54(1H, d, J=8.2Hz), 8.10(1H, t, J=5.3Hz), 8.38(1H, br s), 9.11(1H, br s) | m.p. 175(dec) (° C.).<br>Elemental Analysis<br>C.F.* $C_{26}H_{28}N_2O_4$·0.7$H_2O$·MeSO$_3$H<br>Calcd. C, 59.92; H, 6.22; N, 5.18; S, 5.92<br>Found C, 59.76; H, 6.34; N, 5.11; S, 6.00<br>IR (cm$^{-1}$) (KBr)<br>3442, 3394, 2944, 1657, 1541, 1504, 1471, 1321, 1209, 1193, 1049, 931, 783<br>Mass (EI) 432 (M+) (data of free salt) |
| Compound 24<br>methanesulfonic acid salt<br>Yield 37(%) | 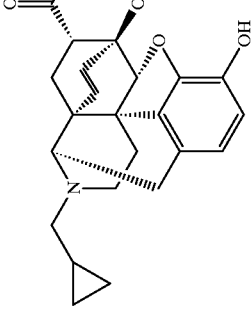 | NMR (ppm) (400 MHz, DMSO-d6)<br>0.38–0.53(2H, m), 0.57–0.77(2H, m), 0.86(3H, t, J=6.8Hz), 1.04–1.16(1H, m), 1.16–1.33(14H, m), 1.33–1.46(2H, m), 1.53(1H, dd, J=6.4, 12.7Hz), 1.99–2.15(2H, m), 2.35(3.9H, s), 2.49–2.56(1H, m), 2.71–2.83(1H, m), 2.89–3.14(5H, m), 3.26–3.53(3H, m), 4.26(1H, s), 4.36(1H, d, J=6.8Hz), 5.45(1H, d, J=8.8Hz), 5.61(1H, d, J=8.8Hz), 6.45(1H, d, J=8.3Hz), 6.54(1H, d, J=8.3Hz), 7.62(1H, t, J=5.6Hz), 8.37(1H, br s), 9.13(1H, br s) | m.p. 130(dec) (° C.).<br>Elemental Analysis<br>C.F.* $C_{33}H_{46}N_2O_4$·0.1$H_2O$·1.3MeSO$_3$H<br>Calcd. C, 62.28; H, 7.83; N, 4.23; S, 6.30<br>Found C, 62.12; H, 7.86; N, 4.43; S, 6.41<br>IR (cm$^{-1}$) (KBr)<br>3384, 2928, 2825, 1638, 1468, 1321, 1210, 1195, 1060, 785, 561, 536<br>Mass (FAB) 535 ((M+H)+) |

-continued

| | | |
|---|---|---|
| Compound 25<br>methanesulfonic acid salt<br>Yield 39(%) 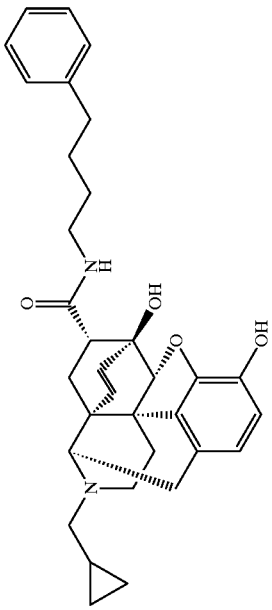 | NMR (ppm) (300 MHz, DMSO-d6)<br>0.37–0.53(2H, m), 0.57–0.78(2H, m), 1.04–1.17(1H, m),<br>1.33–1.46(2H, m), 1.47–1.64(3H, m), 1.97–2.12(2H, m),<br>2.35(4.5H, s), 2.50–2.61(3H, m), 2.75(1H, dd, J=8.5, 12.6Hz),<br>2.87–3.19(5H, m), 3.26–3.36(1H, m), 3.36(1H, d, J=19.2Hz),<br>3.40–3.54(1H, m), 4.26(1H, d, J=6.6Hz), 5.46(1H,<br>d, J=8.8Hz), 5.60(1H, d, J=8.8Hz), 6.45(1H, d, J=8.2Hz),<br>6.53(1H, d, J=8.0Hz), 7.12–7.23(3H, m), 7.23–7.33(2H, m),<br>7.66(1H, br t, J=5.4Hz), 8.36(1H, br s) | m.p. 125(dec) (° C.).<br>Elemental Analysis<br>C.F.* C$_{33}$H$_{38}$N$_2$O$_4$.0.6H$_2$O.1.5MeSO$_3$H<br>Calcd. C, 60.79; H, 6.68; N, 4.11; S, 7.06<br>Found C, 60.61; H, 6.61; N, 4.41; S, 7.06<br>IR (cm$^{-1}$) (KBr)<br>3450, 2938, 2368, 1649, 1638, 1562, 1460,<br>1323, 1209,<br>1195, 1046, 783, 555<br>Mass (FAB) 527 ((M+H)+) |
| Compound 26<br>methanesulfonic acid salt<br>Yield 5(%) 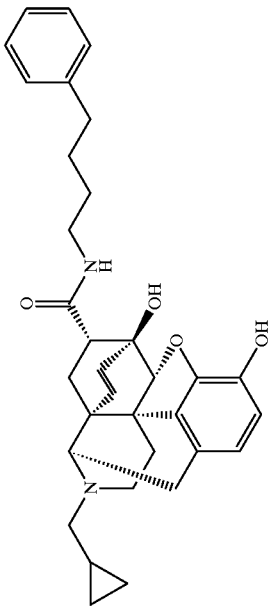 | NMR (ppm) (400 MHz, DMSO-d6)<br>0.36–0.54(2H, m), 0.56–0.76(2H, m), 1.01–1.15(1H, m),<br>1.38–1.52(3H, m), 1.56–1.68(2H, m), 1.78(1H, br d, J=12.5Hz),<br>2.31(4.5H, s), 2.41(1H, dd, J=3.8, 7.2Hz), 2.59(2H, t,<br>J=7.3Hz), 2.79(1H, dd, J=3.8, 12.4Hz), 2.89–3.05(3H, m),<br>3.08–3.21(2H, m), 3.29(1H, br d, J=10.7Hz), 3.36(1H, d,<br>J=19.5Hz), 3.38–3.50(1H, m), 4.31(1H, br s), 4.42(1H,<br>br s), 4.85(1H, s), 5.46(1H, d, J=8.5Hz), 5.81(1H, d, J=8.5Hz),<br>6.44(1H, d, J=7.9Hz), 6.53(1H, d, J=7.9Hz), 7.12–7.33(5H, m),<br>7.87(1H, br t, J=5.5Hz), 8.53(1H, br s), 9.04(1H, br s) | m.p. 115(dec) (° C.).<br>Elemental Analysis<br>Chemical Formula<br>Calcd.<br>Found<br>IR (cm$^{-1}$) (KBr)<br>3408, 2934, 1640, 1547, 1502, 1460, 1321,<br>1205, 1176,<br>1122, 1048, 1031, 785, 555, 538<br>Mass (FAB) 527 ((M+H)+) |
| Compound 27<br>methanesulfonic acid salt<br>Yield 21(%) 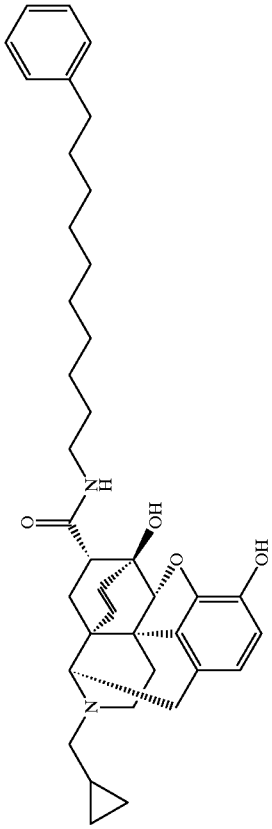 | NMR (ppm) (300 MHz, DMSO-d6)<br>0.37–0.54(2H, m), 0.58–0.78(2H, m), 1.03–1.43(15H, m),<br>1.46–1.62(3H, m), 1.98–2.12(2H, m), 2.31(3H, s), 2.56(2H, t,<br>J=7.7Hz), 2.68–2.81(1H, m), 2.86–3.14(5H, m), 3.25–3.54(4H,<br>m), 4.25(1H, s), 4.36(1H, d, J=6.6Hz), 5.47(1H, d, J=8.8Hz),<br>5.61(1H, d, J=8.8Hz), 5.69(1H, br s), 6.45(1H, d, J=8.0Hz),<br>6.54(1H, d, J=8.0Hz), 7.11–7.22(3H, m), 7.22–7.33(2H, m),<br>7.62(1H, br s), 8.33(1H, br s), 9.11(1H, br s) | m.p. 130(dec) (° C.).<br>Elemental Analysis<br>C.F.* C$_{39}$H$_{50}$N$_2$O$_4$.0.9H$_2$O.MeSO$_3$H<br>Calcd. C, 66.44; H, 7.78; N, 3.87; S, 4.43<br>Found C, 66.40; H, 7.50; N, 4.16; S, 4.62<br>IR (cm$^{-1}$) (KBr)<br>3388, 2928, 2856, 1765, 1657,<br>1649, 1638, 1562, 1547,<br>1460, 1321, 1212, 1197, 1046,<br>924, 774, 698<br>Mass (FAB) 611 ((M+H)+) |

| Compound 28 methanesulfonic acid salt Yield 3(%) 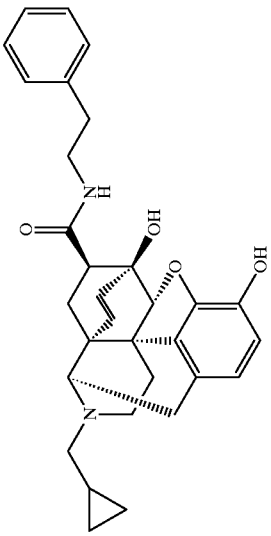 | NMR (ppm) (300 MHz, CDCl3) (data of free salt) 0.05–0.20(2H, m), 0.41–0.59(2H, m), 0.74–0.92(1H, m), 1.48(1H, t, J=12.4Hz), 1.62(1H, d, J=10.7Hz), 2.27–2.57(6H, m), 2.63–2.76(1H, m), 2.86(2H, t, J=7.0Hz), 3.09(2H, d, J=18.1Hz), 3.42–3.68(3H, m), 4.68(1H, br s), 4.93(1H, s), 5.37(1H, d, J=8.5Hz), 5.70(1H, dd, J=1.2, 8.5Hz), 6.32(1H, br s), 6.46(1H, d, J=8.2Hz), 6.62(1H, d, J=8.2Hz), 7.12–7.35(5H, m) | m.p. 115(dec) (° C.). Elemental Analysis Chemical Formula Calcd. Found IR (cm⁻¹) (KBr) 3418, 2946, 1642, 1547, 1502, 1471, 1461, 1321, 1204, 1177, 1048, 784 Mass (EI) 498 (M+) (data of free salt) |
| Compound 29 methanesulfonic acid salt Yield 52(%) 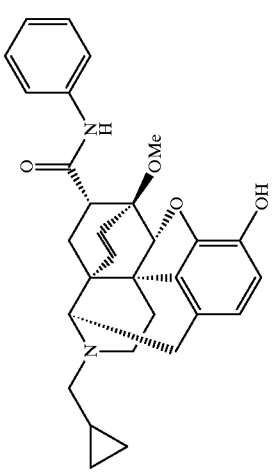 | NMR (ppm) (300 MHz, DMSO-d6) 0.37–0.54(2H, m), 0.59–0.78(2H, m), 1.04–1.18(1H, m), 1.56(1H, dd, J=6.0, 12.4Hz), 2.07–2.21(2H, m), 2.36(3H, s), 2.89–3.13(5H, m), 3.31–3.54(3H, m), 3.51(3H, s), 4.43(1H, d, J=6.9Hz), 4.71(1H, s), 5.61(1H, d, J=8.8Hz), 5.79(1H, d, J=8.8Hz), 6.50(1H, d, J=8.2Hz), 6.57(1H, d, J=8.2Hz), 7.04(1H, t, J=7.4Hz), 7.30(2H, t, J=8.0Hz), 7.58(2H, dd, J=1.0, 8.7Hz), 8.45(1H, br s), 9.16(1H, br s), 10.01(1H, s) | m.p. 205(dec) (° C.). Elemental Analysis C.F.* $C_{30}H_{32}N_2O_4 \cdot 1.2H_2O \cdot MeSO_3H$ Calcd. C, 61.82; H, 6.43; N, 4.65; S, 5.32 Found C, 61.72; H, 6.33; N, 4.85; S, 5.57 IR (cm⁻¹) (KBr) 3430, 1673, 1601, 1545, 1499, 1444, 1321, 1203, 1048, 774 Mass (FAB) 485 ((M+H)+) |
| Compound 30 methanesulfonic acid salt Yield 39(%) 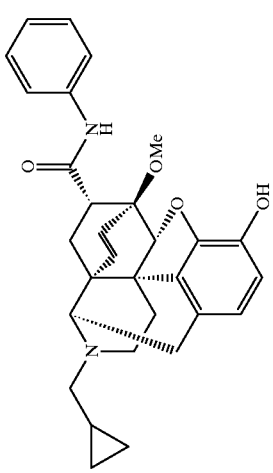 | NMR (ppm) (300 MHz, DMSO-d6) 0.34–0.49(2H, m), 0.57–0.75(3H, m), 1.00–1.15(1H, m), 1.16–1.31(1H, m), 1.39–1.54(1H, m), 1.84–2.22(4H, m), 2.29(3H, s), 2.70–3.05(5H, m), 3.21–3.49(3H, m), 3.35(3H, s), 3.97(1H, d, J=6.7Hz), 4.59(1H, s), 6.58(1H, d, J=8.0Hz), 6.71(1H, d, J=8.0Hz), 7.07(1H, t, J=7.3Hz), 7.32(2H, t, J=8.0Hz), 7.62(2H, d, J=8.2Hz), 8.16(1H, br s), 9.34(1H, s), 10.01(1H, br s) | m.p. 205(dec) (° C.). Elemental Analysis C.F.* $C_{30}H_{34}N_2O_3 \cdot 0.5H_2O \cdot MeSO_3H$ Calcd. C, 62.92; H, 6.64; N, 6.76; S, 5.42 Found C, 62.62; H, 6.76; N, 5.05; S, 5.35 IR (cm⁻¹) (KBr) 3545, 1678, 1601, 1547, 1499, 1444, 1321, 1241, 1209, 1195, 1098, 1046, 770 Mass (FAB) 487 ((M+H)+) |

-continued

| | | |
|---|---|---|
| Compound 31<br>Yield 91(%)<br>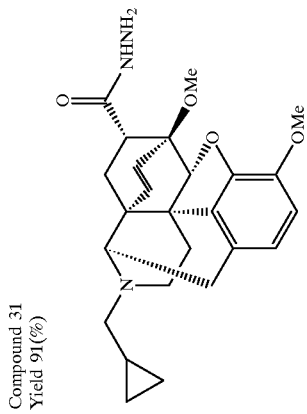 | NMR (ppm) (300 MHz, CDCl3)<br>0.06–0.18(2H, m), 0.43–0.57(2H, m), 0.75–0.90(1H, m), 1.58(1H, dd, J=6.3, 13.2Hz), 1.84(1H, dd, J=2.5, 13.2Hz), 1.99(1H, dt, J=5.5, 12.5Hz), 2.28–2.48(4H, m), 2.59(1H, dd, J=6.3, 9.3Hz), 2.71(1H, dd, J=4.8, 11.7Hz), 3.11(1H, d, J=19.0Hz), 3.13(1H, dd, J=9.9, 12.9Hz), 3.57(1H, d, J=6.6Hz), 3.64(3H, s), 3.82(3H, s), 3.87(2H, d, J=4.1Hz), 4.54(1H, d, J=1.4Hz), 5.60(1H, d, J=8.8Hz), 5.90(1H, d, J=8.8Hz), 6.52(1H, d, J=8.0Hz), 6.62(1H, d, J=8.2Hz), 7.28(1H, br s) | m.p. (° C).<br>Elemental Analysis<br>Chemical Formula<br>Calcd.<br>Found<br>IR (cm⁻¹) (KBr)<br>3456, 3322, 2932, 1655, 1633, 1503, 1443, 1285, 1260, 1208, 1166, 1103, 1055<br>Mass (EI) 437 (M+) |
| Compound 32<br>Yield 81(%)<br>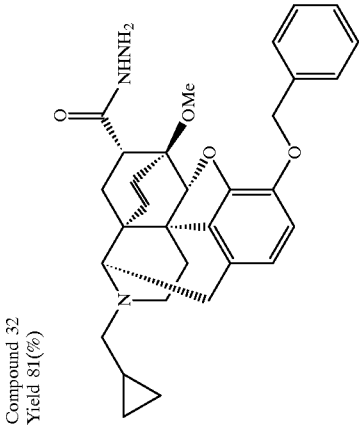 | NMR (ppm) (300 MHz, CDCl3)<br>0.07–0.18(2H, m), 0.44–0.57(2H, m), 0.75–0.89(1H, m), 1.54–1.66(1H, m), 1.85(1H, dd, J=2.3, 13.0Hz), 1.99(1H, d, J=5.3, 12.5Hz), 2.27–2.48(4H, m), 2.57(1H, dd, J=5.8, 9.1Hz), 2.71(1H, dd, J=4.4, 12.6Hz), 3.09(1H, d, J=18.7Hz), 3.12(1H, dd, J=9.9, 13.2Hz), 3.57(1H, d, J=6.3Hz), 3.64(3H, s), 3.87(2H, d, J=4.1Hz), 4.53(1H, d, J=1.4Hz), 5.10(1H, d, J=12.0Hz), 5.13(1H, d, J=12.4Hz), 5.60(1H, d, J=9.1Hz), 5.90(1H, d, J=8.8Hz), 6.47(1H, d, J=8.0Hz), 6.66(1H, d, J=8.2Hz), 7.23–7.43(5H, m) | m.p. (° C).<br>Elemental Analysis<br>Chemical Formula<br>Calcd.<br>Found<br>IR (cm⁻¹) (KBr)<br>3322, 2928, 1659, 1630, 1498, 1445, 1377, 1254, 1207, 1171, 1128, 1048, 1019, 740, 696<br>Mass (EI) 513 (M+) |
| Compound 33<br>hydrohloric acid salt<br>Yield 72(%)<br>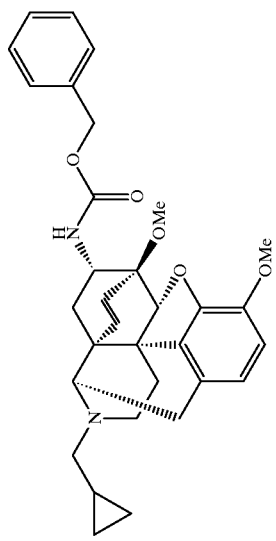 | NMR (ppm) (300 MHz, CDCl3) (data of free salt)<br>0.08–0.18(2H, m), 0.46–0.56(2H, m), 0.76–0.90(1H, m), 1.06(1H, dd, J=4.4, 13.7Hz), 1.83(1H, dd, J=2.2, 12.9Hz), 2.05(1H, dt, J=5.6, 12.6Hz), 2.27–2.46(4H, m), 2.73(1H, dd, J=5.1, 12.2Hz), 3.08(1H, d, J=18.4Hz), 3.42–3.56(2H, m), 3.51(3H, s), 3.81(3H, s), 4.05(1H, br s), 4.71(1H, s), 4.81(1H, br d, J=7.7Hz), 5.10(2H, s), 5.56(1H, d, J=8.8Hz), 5.64(1H, d, J=8.8Hz), 6.51(1H, d, J=8.0Hz), 6.61(1H, d, J=8.0Hz), 7.27–7.42(5H, m) | m.p. (° C).<br>Elemental Analysis<br>Chemical Formula<br>Calcd.<br>Found<br>IR (cm⁻¹) (neat) (data of free salt)<br>3434, 3316, 2940, 2838, 1715, 1506, 1454, 1259, 1230, 1104, 1058, 1006, 911, 733<br>Mass (EI) 528 (M+) (data of free salt) |

-continued

| | | |
|---|---|---|
| Compound 34<br>Yield 89(%) | 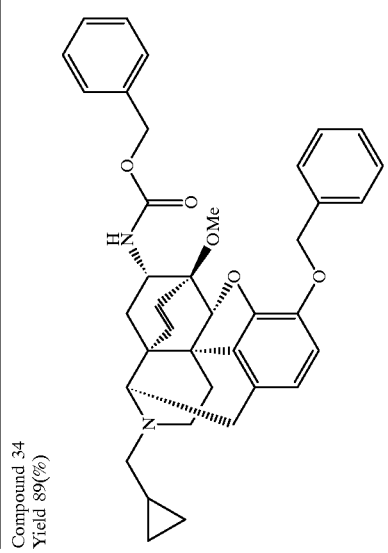 | NMR (ppm) (300 MHz, CDCl3)<br>0.06–0.16(2H, m), 0.45–0.55(2H, m), 0.76–0.90(1H, m),<br>1.06(1H, dd, J=4.4, 13;7Hz), 1.83(1H, dd, J=2.7, 13.2Hz),<br>2.06(1H, dt, J=5.8, 12.9Hz), 2.27–2.44(4H, m), 2.73(1H, dd,<br>J=4.4, 12.4Hz), 3.06(1H, d, J=18.4Hz), 3.41–3.57(2H, m),<br>3.53(3H, s), 4.04(1H, br s), 4.70(1H, br d,<br>J=7.4Hz), 5.05–5.17(4H, m), 5.55(1H, d, J=8.8Hz), 5.64(1H, d,<br>J=8.8Hz), 6.45(1H, d, J=8.2Hz), 6.63(1H, d, J=8.2Hz),<br>7.24–7.45(10H, m) | m.p. (° C.),<br>Elemental Analysis<br>Chemical Formula<br>Calcd.<br>Found<br>IR (cm⁻¹) (neat)<br>3418, 2932, 1645, 1321, 1209, 1195, 1047,<br>784, 557<br>Mass (EI) 604 (M+) |
| Compound 35<br>hydrohloric acid salt<br>Yield 82(%) | 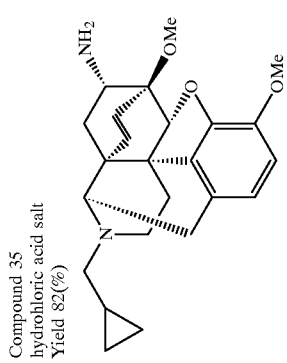 | NMR (ppm) (300 MHz, CDCl3) (data of free salt)<br>0.88–0.19(2H, m), 0.44–0.58(2H, m), 0.76(1H, dd, J=4.7,<br>13.5Hz), 0.77–0.92(1H, m), 1.79(1H, dd, J=2.5, 13.2Hz),<br>2.00(1H, dt, J=5.7, 12.6Hz), 2.29–2.46(4H, m), 2.70(1H, dd,<br>J=5.1, 11.9Hz), 3.03(1H, ddd, J=1.4, 4.7, 8.8Hz), 3.08(1H, d,<br>J=19.0Hz), 3.31(1H, dd, J=8.8, 13.5Hz), 3.49(1H, d, J=6.6Hz),<br>3.64(3H, s), 3.83(3H, s), 4.53(1H, d, J=1.1Hz), 5.57(1H, d,<br>J=8.8Hz), 5.74(1H, d, J=8.2Hz), 6.51(1H, d, J=8.2Hz), 6.62(1H,<br>d, J=8.0Hz) | m.p. (° C.),<br>Elemental Analysis<br>Chemical Formula<br>Calcd.<br>Found<br>IR (cm⁻¹) (KBr) (data of free salt)<br>3418, 2948, 1633, 1505, 1455,<br>1289, 1266, 1167, 1105, 947<br>Mass (EI) 394 (M+) (data of free salt) |
| Compound 36<br>Yield 73(%) | 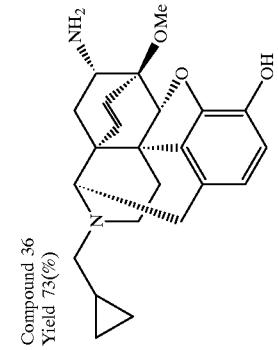 | NMR (ppm) (300 MHz, CDCl3)<br>0.07–0.19(2H, m), 0.42–0.57(2H, m), 0.79(1H, dd, J=4.4,<br>13.5Hz), 0.75–0.90(1H, m), 1.80(1H, dd, J=2.5, 12.9Hz),<br>2.00(1H, dt, J=5.5, 12.7Hz), 2.27–2.45(4H, m), 2.70(1H, dd,<br>J=4.5, 11.9Hz), 3.02–3.10(1H, m), 3.06(1H, d, J=18.4Hz),<br>3.31(1H, dd, J=8.8, 13.5Hz), 4.48(1H, d, J=6.6Hz), 3.61(3H, s),<br>4.52(1H, d, J=1.1Hz), 5.56(1H, d, J=8.8Hz), 5.68(1H, d,<br>J=8.8Hz), 6.46(1H, d, J=8.0Hz), 5.59(1H, d, J=8.0Hz) | m.p. (° C.),<br>Elemental Analysis<br>Chemical Formula<br>Calcd.<br>Found<br>IR (cm⁻¹) (KBr)<br>3420, 3362, 3002, 2930, 2828,<br>1631, 1606, 1503, 1462,<br>1325, 1254, 1102, 1033, 955, 910, 782, 753<br>Mass (EI) 380 (M+) |

-continued

| | NMR (ppm) (400 MHz, CDCl3) 0.09–0.19(2H, m), 0.45–0.56(2H, m), 0.77–0.89(1H, m), 1.70(1H, dd, J=10.1, 13.1Hz), 1.76(1H, dd, J=2.3, 12.8Hz), 2.27–2.46(5H, m), 2.52(1H, dt, J=4.9, 12.5Hz), 2.72(1H, dd, J=4.9, 11.2Hz), 3.08(1H, d, J=18.3Hz), 3.33(1H, dd, J=2.9, 10.0Hz), 3.46–3.52(1H, m), 3.50(3H, s), 5.12(1H, d, J=0.7Hz), 5.48(1H, d, J=8.8Hz), 5.91(1H, dd, J=1.0, 8.8Hz), 6.45(1H, d, J=8.1Hz), 6.59(1H, d, J=8.1Hz) | m.p. (° C.), Elemental Analysis Chemical Formula Calcd. Found IR (cm⁻¹) (KBr) 3456, 3354, 3002, 2932, 2832, 1632, 1606, 1503, 1462, 1376, 1323, 1130, 1100, 1028, 954, 941, 887, 753 Mass (EI) 380 (M+) |
|---|---|---|
| Compound 37 Yield 11(%) 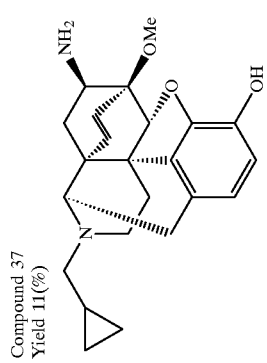 | | |
| Compound 38 Yield 100(%) 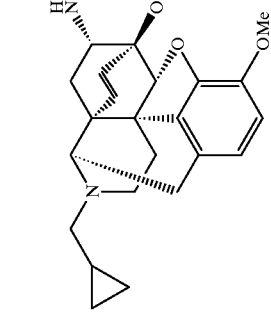 | NMR (ppm) (300 MHz, CDCl3) 0.07–0.16(2H, m), 0.46–0.54(2H, m), 0.77–0.91(1H, m), 1.14(1H, dd, J=4.7, 13.7Hz), 1.87(1H, dd, J=2.2, 12.9Hz), 2.15(1H, dt, J=5.5, 12.6Hz), 2.31–2.49(4H, m), 2.77(1H, dd, J=4.9, 11.5Hz), 3.11(1H, d, J=18.4Hz), 3.49(1H, d, J=6.6Hz), 3.52(3H, s), 3.65(1H, dd, J=8.9, 13.6Hz), 3.83(3H, s), 4.41–4.51(1H, m), 4.77(1H, d, J=1.4Hz), 5.64(1H, d, J=8.8Hz), 5.73(1H, d, J=8.8Hz), 6.19(1H, d, J=7.1Hz), 6.54(1H, d, J=8.2Hz), 6.63(1H, d, J=8.2Hz), 7.37–7.57(3H, m), 7.69–7.76(2H, m) | m.p. (° C.), Elemental Analysis Chemical Formula Calcd. Found IR (cm⁻¹) (KBr) 2936, 2836, 1648, 1503, 1443, 1286, 1106, 909, 731 Mass (EI) 498 (M+) |
| Compound 39 Yield 96(%) 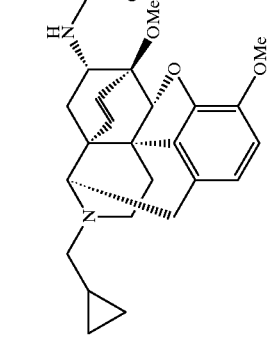 | NMR (ppm) (300 MHz, CDCl3) 0.08–0.16(2H, m), 0.46–0.54(2H, m), 0.76–0.91(1H, m), 1.10(1H, dd, J=4.7, 13.7Hz), 1.85(1H, dd, J=2.3, 13.0Hz), 2.14(1H, dt, J=5.6, 12.7Hz), 2.28–2.48(4H, m), 2.76(1H, dd, J=4.7, 12.0Hz), 3.10(1H, d, J=18.4Hz), 3.46–3.52(1H, m), 3.51(3H, s), 3.61(1H, dd, J=8.9, 13.8Hz), 3.83(3H, s), 4.37–4.47(1H, m), 4.76 1H, d, J=1.4Hz), 5.63(1H, d, J=8.5Hz), 5.67(1H, br s), 5.70(1H, d, J=8.8Hz), 6.37(1H, d, J=15.7Hz), 6.53(1H, d, J=8.0Hz), 6.63(1H, d, J=8.0Hz), 7.32–7.41(3H, m), 7.46–7.53(2H, m), 7.62(1H, d, J=15.7Hz) | m.p. (° C.), Elemental Analysis Chemical Formula Calcd. Found IR (cm⁻¹) (KBr) 3426, 3298, 3000, 2938, 2836, 1661, 1627, 1533, 1503, 1450, 1213, 1167, 1105, 1056, 983, 765 Mass (EI) 524 (M+) |

| | | |
|---|---|---|
| Compound 40<br>Yield 58(%) 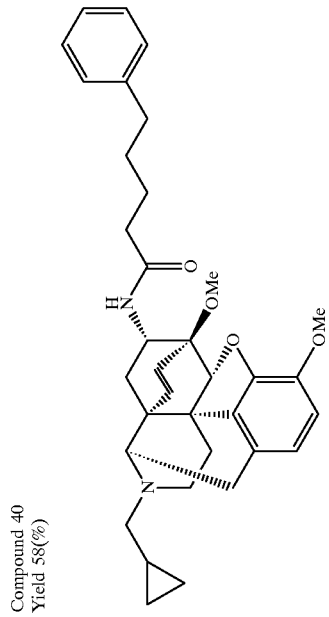 | NMR (ppm) (300 MHz, CDCl3)<br>0.07–0.15(2H, m), 0.46–0.54(2H, m), 0.76–0.90(1H, m), 0.96(1H, dd, J=4.5, 13.6Hz), 1.57–1.72(4H, m), 1.82(1H, dd, J=2.2, 13.5Hz), 2.02–2.20(3H, m), 2.28–2.46(4H, m), 2.57–2.67(2H, m), 2.74(1H, dd, J=4.8, 11.7Hz), 3.09(1H, d, J=18.4Hz), 3.45(3H, s), 3.46(1H, d, J=5.2Hz), 3.52(1H, d, J=9.1, 13.5Hz), 3.82(3H, s), 4.29(1H, dt, J=4.6, 7.7Hz), 4.70(1H, d, J=1.4Hz), 5.42(1H, d, J=8.0Hz), 5.58(1H, d, J=8.8Hz), 5.63(1H, d, J=8.5Hz), 6.51(1H, d, J=8.2Hz), 6.61(1H, d, J=8.2Hz), 7.12–7.21(3H, m), 7.23–7.31(2H, m) | m.p. (° C).<br>Elemental Analysis<br>Chemical Formula<br>Calcd.<br>Found<br>IR (cm⁻¹) (KBr)<br>3310, 2936, 2838, 1647, 1535, 1502, 1444, 1285, 1261, 1208, 1167, 1103, 913, 732, 700<br>Mass (EI) 554 (M+) |
| Compound 41<br>Yield 88(%) 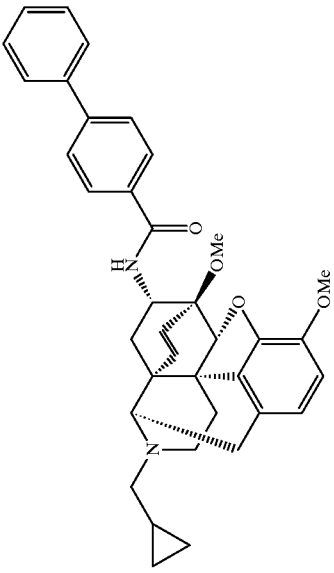 | NMR (ppm) (300 MHz, CDCl3)<br>0.08–0.17(2H, m), 0.46–0.54(2H, m), 0.78–0.93(1H, m), 1.17(1H, dd, J=4.7, 13.7Hz), 1.87(1H, dd, J=2.5, 12.9Hz), 2.16(1H, d, J=5.7, 12.5Hz), 2.30–2.49(4H, m), 2.78(1H, dd, J=4.5, 11.7Hz), 3.12(1H, d, J=18.4Hz), 3.51(1H, d, J=6.6Hz), 3.53(3H, s), 3.67(1H, dd, J=8.8, 13.7Hz), 3.84(3H, s), 4.43–4.53(1H, m), 4.78(1H, d, J=1.4Hz), 5.66(1H, d, J=8.8Hz), 5.75(1H, d, J=8.5Hz), 6.23(1H, d, J=7.1Hz), 6.54(1H, d, J=8.0Hz), 6.64(1H, d, J=8.2Hz), 7.35–7.50(3H, m), 7.57–7.68(4H, m), 7.77–7.84(2H, m) | m.p. (° C).<br>Elemental Analysis<br>Chemical Formula<br>Calcd.<br>Found<br>IR (cm⁻¹) (neat)<br>3352, 2936, 2838, 2250, 1655, 1612, 1526, 1503, 1485, 1444, 1286, 1263, 1209, 1169, 1107, 1056, 908, 780, 727<br>Mass (EI) 574 (M+) |
| Compound 42<br>Yield 94(%) 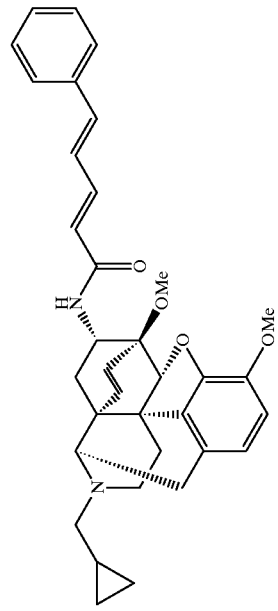 | NMR (ppm) (300 MHz, CDCl3)<br>0.06–0.16(2H, m), 0.44–0.55(2H, m), 0.76–0.91(1H, m), 1.07(1H, dd, J=4.4, 13.7Hz), 1.85(1H, dd, J=2.2, 12.9Hz), 2.13(1H, dt, J=5.1, 12.6Hz), 2.27–2.47(4H, m), 2.75(1H, dd, J=4.7, 12.1Hz), 3.10(1H, d, J=18.7Hz), 3.44–3.52(1H, m), 3.49(3H, s), 3.59(1H, dd, J=8.9, 13.6Hz), 3.83(3H, s), 4.39(1H, dt, J=4.1, 7.4Hz), 4.74(1H, d, J=1.4Hz), 5.58(1H, d, J=6.3Hz), 5.61(1H, d, J=8.8Hz), 5.68(1H, d, J=8.8Hz), 5.93(1H, d, J=14.8Hz), 6.53(1H, d, J=8.2Hz), 6.62(1H, d, J=8.2Hz), 6.75–6.93(2H, m), 7.24–7.49(6H, m) | m.p. (° C).<br>Elemental Analysis<br>Chemical Formula<br>Calcd.<br>Found<br>IR (cm⁻¹) (KBr)<br>3416, 2934, 1655, 1617, 1502, 1448, 1259, 1106, 1001, 694<br>Mass (EI) 550 (M+) |

| | -continued | |
|---|---|---|
| Compound 43<br>Yield 84(%)<br>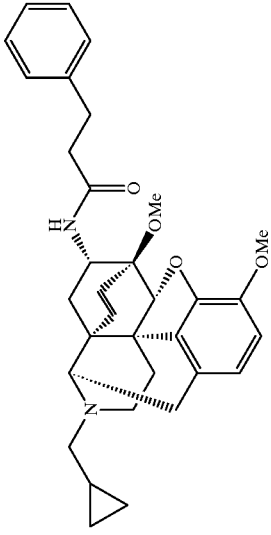 | NMR (ppm) (300 MHz, CDCl3)<br>0.08–0.16(2H, m), 0.45–0.55(2H, m), 0.75–0.91(H, m),<br>0.86(1H, dd, J=4.4, 13.7Hz), 1.77–1.85(1H, m), 2.07(1H, dt,<br>J=5.8, 12.7Hz), 2.29–2.50(6H, m), 2.73(1H, dd, J=5.1, 12.0Hz),<br>2.91–2.99(2H, m), 3.08(1H, d, J=19.0Hz), 3.37(3H, s),<br>3.44(1H, d, J=6.6Hz), 3.49(1H, dd, J=8.8, 13.7Hz), 3.81(3H, s),<br>4.19–4.28(1H, m), 4.67(1H, d, J=1.1Hz), 5.37(1H, br d,<br>J=7.7Hz), 5.54(1H, d, J=8.5Hz), 5.57(1H, d, J=8.8Hz), 6.51(1H,<br>d, J=8.2Hz), 6.61(1H, d, J=8.2Hz), 7.14–7.30(5H, m) | m.p. (° C.),<br>Elemental Analysis<br>Chemical Formula<br>Calcd.<br>Found<br>IR (cm⁻¹) (KBr)<br>3294, 2934, 1651, 1542, 1500,<br>1452, 1286, 1261, 1209,<br>1166, 1103, 1057, 780, 750, 700<br>Mass (EI) 526 (M+) |
| Compound 44<br>methanesulfonic acid salt<br>Yield 82(%)<br>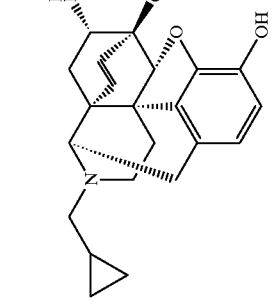 | NMR (ppm) (300 MHz, DMSO-d6)<br>0.37–0.55(2H, m), 0.57–0.77(2H, m), 1.05–1.20(1H, m),<br>1.23(1H, dd, J=4.8, 13.3Hz), 2.00–2.11(1H, m), 2.17–2.31(1H,<br>m), 2.31(3.3H, s), 2.88–3.09(3H, m), 3.24–3.58(4H, m),<br>4.20(1H, dd, J=7.8, 13.0Hz), 4.30(1H, d, J=6.3Hz), 4.50(1H, s),<br>5.64(1H, d, J=8.8Hz), 5.73(1H, d, J=8.8Hz), 6.47(1H, d,<br>J=8.0Hz), 6.55(1H, d, J=8.0Hz), 7.41–7.58(3H, m), 7.74(1H, d,<br>J=6.9Hz), 7.77–7.88(2H, m), 8.44(1H, br s), 9.16(1H, br s) | m.p. 215(dec) (° C.),<br>Elemental Analysis<br>C.F.* C₂₉H₃₀N₂O₄·0.5H₂O·1.1MeSO₃H<br>Calcd. C, 61.77; H, 6.10; N, 4.79; S, 6.03<br>Found C, 61.71; H, 6.23; N, 5.09; S, 5.94<br>IR (cm⁻¹) (KBr)<br>3444, 1639, 1540, 1320, 1210,<br>1196, 1057, 785, 559, 535<br>Mass (FAB) 471 ((M+H)+) |
| Compound 45<br>methanesulfonic acid salt<br>Yield 61(%)<br>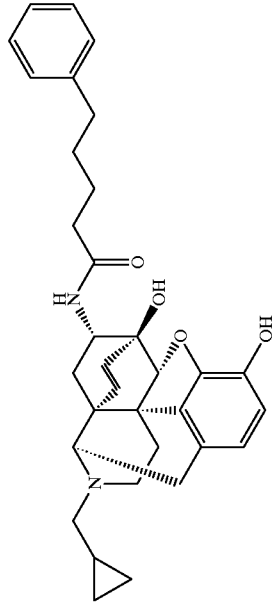 | NMR (ppm) (400 MHz, DMSO-d6)<br>0.37–0.51(2H, m), 0.58–0.74(2H, m), 0.97(1H, dd, J=4.7,<br>13.3Hz), 1.05–1.16(1H, m), 1.44–1.58(4H, m), 2.01(1H, d,<br>J=11.6Hz), 2.09–2.23(3H, m), 2.32(3.9H, s), 2.56(2H, t,<br>J=7.0Hz), 2.87–3.04(3H, m), 3.21(1H, dd, J=8.6, 13.1Hz),<br>3.28–3.38(2H, m), 3.41–3.50(1H, m), 3.94(1H, dd, J=7.9,<br>12.5Hz), 4.27(1H, d, J=7.0Hz), 4.40(1H, s), 5.59(1H, d,<br>J=8.9Hz), 5.65(1H, d, J=8.9Hz), 6.45(1H, d, J=7.9Hz), 6.54(1H,<br>d, J=7.9Hz), 7.13–7.20(3H, m), 7.23–7.30(2H, m), 7.48(1H, d,<br>J=7.3Hz), 8.37(1H, br s), 8.88(1H, br s) | m.p. 150(dec) (° C.),<br>Elemental Analysis<br>C.F.* C₃₃H₃₈N₂O₄·0.5H₂O·1.3MeSO₃H<br>Calcd. C, 62.36; H, 6.74; N, 4.24; S, 6.31<br>Found C, 62.11; H, 6.74; N, 4.53; S, 6.30<br>IR (cm⁻¹) (KBr)<br>3402, 2938, 1640, 1545, 1503,<br>1463, 1321, 1210, 1195,<br>1058, 785, 560<br>Mass (FAB) 527 ((M+H)+) |
| Compound 46 | NMR (ppm) (400 MHz, DMSO-d6) | m.p. 220(dec) (° C.). |

| | -continued | |
|---|---|---|
| methanesulfonic acid salt<br>Yield 33(%)<br>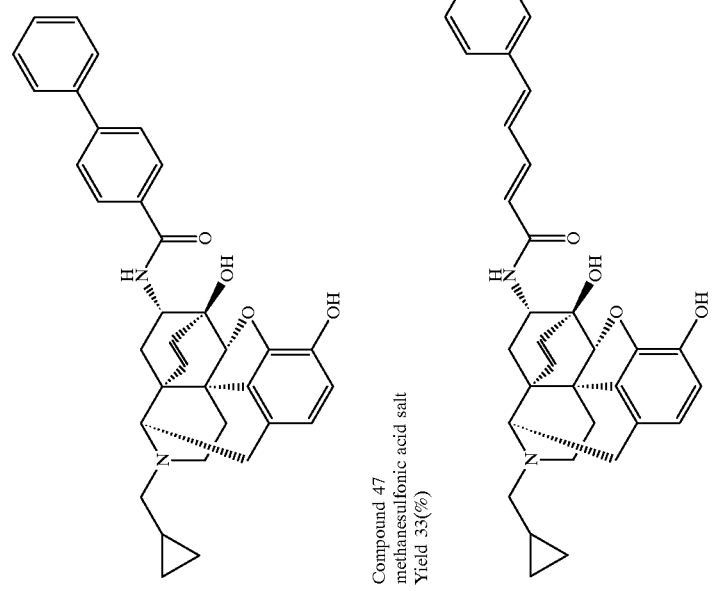 | 0.38–0.54(2H, m), 0.59–0.76(2H, m), 1.07–1.19(1H, m), 1.26(1H, dd, J=4.9, 13.4Hz), 2.07(1H, br d, J=12.8Hz), 2.20–2.32(1H, m), 2.32(3H, s), 2.91–3.09(3H, m), 3.26–3.42(3H, m), 3.44–3.54(1H, m), 4.19–4.27(1H, m), 4.31(1H, d, J=6.7Hz), 4.52(1H, s), 5.65(1H, d, J=8.8Hz), 5.75(1H, d, J=8.6Hz), 6.47(1H, d, J=7.9Hz), 6.56(1H, d, J=7.9Hz), 7.37–7.44(1H, m), 7.46–7.54(2H, m), 7.69–7.80(4H, m), 7.81(1H, d, J=7.0Hz), 7.92(2H, d, J=8.5Hz), 8.45(1H, br s), 9.16(1H, br s) | Elemental Analysis<br>C.F.* $C_{33}H_{34}N_2O_4 \cdot H_2O \cdot MeSO_3H$<br>Calcd. C, 65.44; H, 6.10; N, 4.24; S, 5.22<br>Found C, 65.37; H, 6.07; N, 4.21; S, 5.22<br>IR (cm$^{-1}$) (KBr)<br>3448, 3420, 1638, 1614, 1542, 1508, 1486, 1322, 1201, 1167, 1046, 785, 751<br>Mass (FAB) 547 ((M+H)+) |
| Compound 47<br>methanesulfonic acid salt<br>Yield 33(%)<br>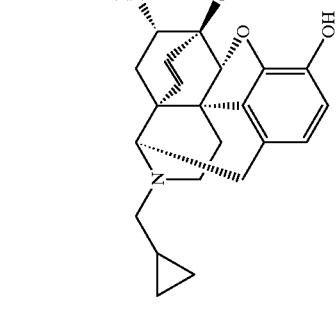 | NMR (ppm) (500 MHz, DMSO-d6)<br>0.39–0.52(2H, m), 0.60–0.75(2H, m), 1.06(1H, dd, J=4.9, 13.2Hz), 1.07–1.56(1H, m), 2.00–2.07(1H, m), 2.21(1H, d, J=4.6, 13.9Hz), 2.32(3.3H, s), 2.90–3.05(3H, m), 3.26(1H, dd, J=8.8, 13.2Hz), 3.30–3.40(2H, m), 3.43–3.52(1H, m), 4.04–4.11(1H, m), 4.31(1H, d, J=6.4Hz), 4.44(1H, s), 5.62(1H, d, J=8.8Hz), 5.68(1H, d, J=7.8Hz), 6.28(1H, d, J=14.6Hz), 6.46(1H, d, J=7.8Hz), 6.55(1H, d, J=8.3Hz), 6.94–7.06(2H, m), 7.21(1H, dd, J=10.0, 14.9Hz), 7.30(1H, t, J=7.3Hz), 7.35–7.40(2H, m), 7.56(2H, d, J=7.8Hz), 7.79(1H, d, J=7.3Hz), 8.40(1H, br s), 9.12(1H, br s) | m.p. 215(dec)(° C.)<br>Elemental Analysis<br>C.F.* $C_{33}H_{34}N_2O_4 \cdot 0.7H_2O \cdot 0.1MeSO_3H$<br>Calcd. C, 63.90; H, 6.26; N, 4.37; S, 5.50<br>Found C, 63.95; H, 6.31; N, 4.31; S, 5.68<br>IR (cm$^{-1}$) (KBr)<br>3448, 3418, 1652, 1615, 1543, 1366, 1323, 1205, 1048, 1002, 785<br>Mass (FAB) 523 ((M+H)+) |

| | | -continued | |
|---|---|---|---|
| Compound 48 methanesulfonic acid salt Yield 50(%) | 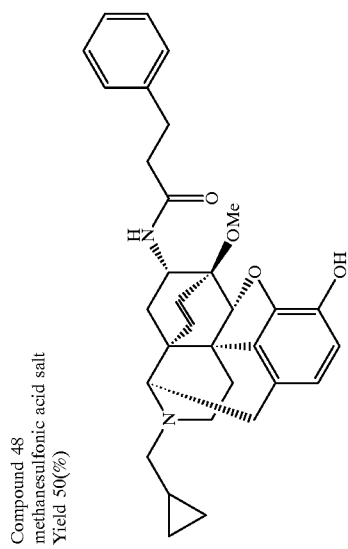 | NMR (ppm) (600 MHz, DMSO-d6) 0.39–0.44(1H, m), 0.45–0.50( 1H, m), 0.61–0.66(1H, m), 0.68–0.75(1H, m), 0.91(1H, dd, J=4.4, 13.1Hz), 1.07–1.14(1H, m), 2.01(1H, br d, J=11.7Hz), 2.23(1H, dt, J=4.9, 14.1Hz), 2.30(3H, s), 2.36–2.47(2H, m), 2.75–2.85(2H, m), 2.88–3.04(3H, m), 3.22(1H, dd, J=8.9, 13.1Hz), 3.25(3H, s), 3.29–3.38(2H, m), 3.42–3.49(1H, m), 4.28(1H, d, J=6.8Hz), 4.34(1H, dt, J=4.7, 18.1Hz), 4.96(1H, s), 5.61(1H, d, J=8.8Hz), 5.63(1H, d, J=8.8Hz), 6.46(1H, d, J=8.1Hz), 6.54(1H, d, J=8.1Hz), 7.17(1H, t, J=7.3Hz), 7.20(2H, d, J=7.3Hz), 7.26(2H, t, J=7.5Hz), 7.60(1H, d, J=8.1Hz), 8.40(1H, br s), 9.14(1H, br s) | m.p. 175(dec) (° C.). Elemental Analysis C.F.* $C_{32}H_{36}N_2O_4 \cdot H_2O \cdot MeSO_3H$ Calcd. C, 63.24; H, 6.75; N, 4.47; S, 5.12 Found C, 63.68; H, 6.90; N, 4.51; S, 5.00 IR (cm$^{-1}$) (KBr) 3412, 1642, 1559, 1457, 1211, 1168, 1042, 782, 555 Mass (FAB) 513 ((M+H)+) |
| Compound 49 methanesulfonic acid salt Yield 23(%) | 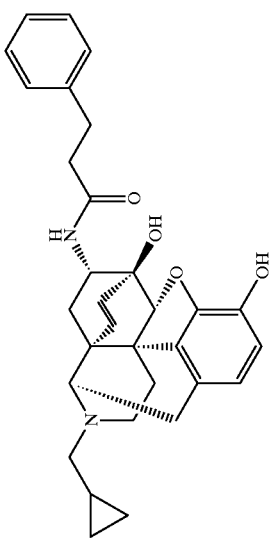 | NMR (ppm) (400 MHz, DMSO-d6) 0.37–0.53(2H, m), 0.59–0.77(2H, m), 0.92(1H, dd, J=4.4, 13.2Hz), 1.05–1.17(1H, m), 1.96–2.05(1H, m), 2.18(1H, dt, J=4.4, 13.9Hz), 2.32(3.3H, s), 2.42(1H, dt, J=3.1, 7.8Hz), 2.79(2H, t, J=7.8Hz), 2.87–3.05(3H, m), 3.19(1H, dd, J=8.8, 13.2Hz), 3.28–3.40(2H, m), 3.42–3.52(1H, m), 3.91–4.00(1H, m), 4.26(1H, d, J=6.8Hz), 4.41(1H, s), 5.58(1H, d, J=8.3Hz), 5.65(1H, d, J=8.3Hz), 6.45(1H, d, J=7.8Hz), 6.55(1H, d, J=8.3Hz), 7.13–7.31(5H, m), 7.52(1H, d, J=7.3Hz), 8.38(1H, br s), 9.11(1H, br s) | m.p. 170(dec) (° C.). Elemental Analysis C.F.* $C_{31}H_{34}N_2O_4 \cdot 0.5H_2O \cdot 0.1MeSO_3H$ Calcd. C, 62.86; H, 6.47; N, 4.57; S, 5.75 Found C, 62.64; H, 6.51; N, 4.56; S, 5.99 IR (cm$^{-1}$) (KBr) 3426, 1639, 1546, 1502, 1461, 1322, 1210, 1195, 1048, 931, 785, 703 Mass (FAB) 499 ((M+H)+) |

-continued

| | NMR (ppm) (300 MHz, CDCl3) | m.p. (° C.), |
|---|---|---|
| Compound 50<br>Yield 89(%)<br>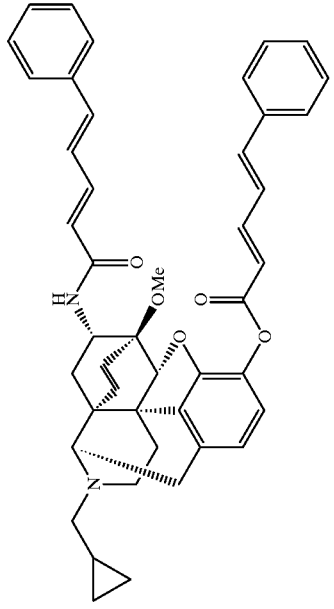 | 0.08–0.16(2H, m), 0.46–0.54(2H, m), 0.76–0.92(1H, m), 1.08(1H, dd, J=4.5, 13.9Hz), 1.91(1H, br d, J=10.7Hz), 2.07–2.20(1H, m), 2.30–2.52(4H, m), 2.78(1H, dd, J=4.7, 12.9Hz), 3.13(1H, d, J=19.0Hz), 3.48(3H, s), 3.50(1H, d, J=6.0Hz), 3.59(1H, dd, J=8.7, 13.6Hz), 4.30–4.40(1H, m), 4.76(1H, s), 5.57(1H, d, J=7.1Hz), 5.64(1H, d, J=8.8Hz), 5.72(1H, d, J=8.8Hz), 5.93(1H, d, J=14.8Hz), 6.18(1H, d, J=15.4Hz), 6.58(1H, d, J=8.0Hz), 6.78(1H, d, J=8.0Hz), 6.81–7.02(4H, m), 7.25–7.54(11H, m), 7.55–7.66(1H, m) | Elemental Analysis<br>Chemical Formula<br>Calcd.<br>Found<br>IR (cm$^{-1}$) (KBr)<br>3420, 3374, 2934, 1732, 1660, 1624, 1492, 1449, 1235, 1201, 1164, 1117, 1000, 754, 692<br>Mass (FAB) 693 ((M+H)+) |
| Compound 51<br>methanesulfonic acid salt<br>Yield 94(%)<br>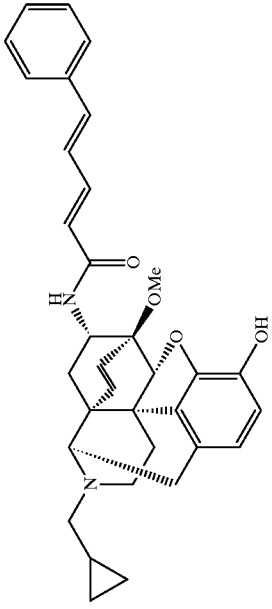 | NMR (ppm) (500 MHz, DMSO-d6)<br>0.38–0.52(2H, m), 0.60–0.75(2H, m), 1.06(1H, dd, J=4.6, 13.4Hz), 1.06–1.56(1H, m), 2.04(1H, br d, J=11.7Hz), 2.24–2.32(1H, m), 2.32(3H, s), 2.90–3.07(3H, m), 3.26–3.40(3H, m), 3.35(3H, s), 3.43–3.50(1H, m), 4.33(1H, d, J=6.8Hz), 4.48(1H, dt, J=4.4, 8.3Hz), 5.01(1H, s), 5.64–5.71(2H, m), 6.28(1H, d, J=15.1Hz), 6.48(1H, d, J=8.3Hz), 6.56(1H, d, J=8.3Hz), 6.94–7.05(2H, m), 7.22(1H, dd, J=9.8, 15.1Hz), 7.30(1H, d, J=7.3Hz), 7.37(2H, t, J=7.6Hz), 7.56(2H, d, J=7.3Hz), 7.84(1H, d, J=8.3Hz), 8.44(1H, br s), 9.14(1H, br s) | m.p. 210(dec) (° C.),<br>Elemental Analysis<br>C.F.* C$_{34}$H$_{36}$N$_2$O$_4$.0.8H$_2$O.MeSO$_3$H<br>Calcd. C, 64.96; H, 6.48; N, 4.33; S, 4.95<br>Found C, 64.89; H, 6.38; N, 4.35; S, 5.23<br>IR (cm$^{-1}$) (KBr)<br>3450, 3420, 3264, 1652, 1611, 1539, 1262, 1210, 1197, 1178, 1166, 1057, 1049, 1004, 784<br>Mass (FAB) 537 ((M+H)+) |

-continued

| | | |
|---|---|---|
| Compound 52<br>methanesulfonic acid salt<br>Yield 79(%)<br>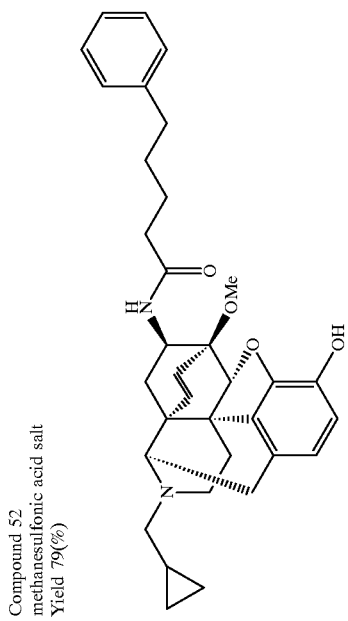 | NMR (ppm) (400 MHz, DMSO-d6)<br>0.36–0.50(2H, m), 0.59–0.76(2H, m), 1.02–1.13(1H, m),<br>1.50–1.65(4H, m), 1.90–2.00(2H, m), 2.15–2.35(3H, m),<br>2.30(3H, s), 2.41(1H, dt, J=4.2, 13.5Hz), 2.61(2H, t, J=6.8Hz),<br>2.89–3.04(3H, m), 3.23(3H, s), 3.25–3.48(3H, m),<br>4.06–4.14(1H, m), 4.31(1H, d, J=6.8Hz), 5.04(1H, s), 5.58(1H,<br>d, J=9.0Hz), 6.07(1H, d, J=9.0Hz), 6.46(1H, d, J=8.3Hz),<br>6.54(1H, d, J=8.3Hz), 7.14–7.23(3H, m), 7.26–7.32(2H, m),<br>8.01(1H, d, J=7.8Hz), 8.46(1H, br s), 9.13(1H, s) | m.p. 155(dec) (° C.).<br>Elemental Analysis<br>C.F.* $C_{34}H_{40}N_2O_4 \cdot 0.6H_2O \cdot MeSO_3H$<br>Calcd. C, 64.91; H, 7.03; N, 4.33; S, 4.95<br>Found C, 64.85; H, 6.91; N, 4.30; S, 5.23<br>IR (cm$^{-1}$) (KBr)<br>3410, 2942, 1642, 1542, 1504,<br>1462, 1323, 1212, 1177,<br>1122, 1046, 777, 701<br>Mass (FAB) 541 ((M+H)+) |
| Compound 53<br>methanesulfonic acid salt<br>Yield 87(%)<br>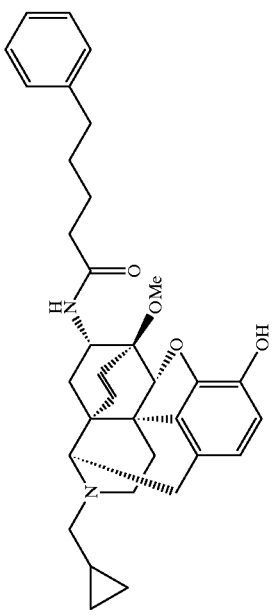 | NMR (ppm) (300 MHz, DMSO-d6)<br>0.44–0.52(2H, m), 0.56–0.77(1H, m), 0.97(1H, dd, J=4.6,<br>13.0Hz), 1.02–1.19(1H, m), 1.42–1.60(4H, m), 1.96–2.30(4H,<br>m), 2.31(3H, s), 2.51–2.60(2H, m), 2.84–3.08(3H, m),<br>3.17–3.51(4H, m), 3.29(3H, s), 4.29(1H, d, J=6.6Hz),<br>4.30–4.42 (1H, m), 4.96(1H, s), 5.62(1H, d, J=9.1Hz), 5.64(1H,<br>d, J=8.8Hz), 6.47(1H, d, J=8.1Hz), 6.55(1H, d, J=8.1Hz),<br>7.12–7.21(3H, m), 7.23–7.32(2H, m), 7.56(1H, d, J=8.4Hz),<br>8.39(1H, br s), 9.15(1H, br s) | m.p. 175(dec) (° C.).<br>Elemental Analysis<br>C.F.* $C_{34}H_{40}N_2O_4 \cdot 0.1H_2O \cdot MeSO_3H$<br>Calcd. C, 65.83; H, 6.93; N, 4.39; S, 5.02<br>Found C, 65.58; H, 7.02; N, 4.51; S, 5.02<br>IR (cm$^{-1}$) (KBr)<br>3452, 3416, 3074, 2940, 1642,<br>1544, 1319, 1205, 1180,<br>1167, 1050, 784<br>Mass (FAB) 541 ((M+H)+) |
| Compound 54<br>phosphoric acid salt<br>Yield 46(%)<br>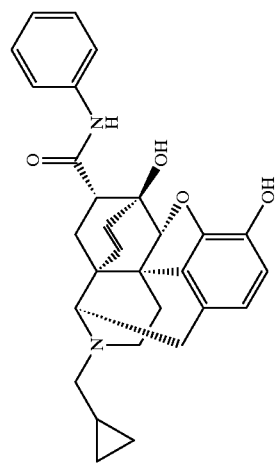 | NMR (ppm) (300 MHz, DMSO-d6)<br>0.18–0.30(2H, m), 0.40–0.65(3H, m), 0.75–0.90(1H, m),<br>1.04–1.28(2H, m), 1.62(1H, d, J=11.3Hz), 1.70–1.85(2H, m),<br>2.04(1H, dt, J=5.4, 11.8Hz), 2.22–2.56(4H, m), 2.65–2.84(3H,<br>m), 2.96(1H, d, J=17.9Hz), 3.14(1H, br s), 4.14(1H, s),<br>6.45(1H, d, J=8.0Hz), 6.58(1H, d, J=8.0Hz), 7.02(1H, t,<br>J=7.4Hz), 7.24–7.34(2H, m), 7.65(2H, d, J=7.4Hz), 9.77(1H, s) | m.p. 220(dec) (° C.).<br>Elemental Analysis<br>C.F.* $C_{29}H_{32}N_2O_4 \cdot H_3PO_4 \cdot 1.9H_2O$<br>Calcd. C, 57.59; H, 6.47; N, 4.63; P, 5.12<br>Found C, 57.45; H, 6.18; N, 4.77; P, 5.48<br>IR (cm$^{-1}$) (KBr)<br>3392, 3416, 1641, 1601, 1547,<br>1500, 1464, 1444, 1321,<br>1252, 1170, 1085, 1030, 988, 952, 760<br>Mass (FAB) 473 ((M+H)+) |

-continued

| | NMR (ppm) (600 MHz, DMSO-d6) 0.35–0.41(1H, m), 0.42–0.48(1H, m), 0.56–0.64(2H, m), 0.65–0.71(1H, m), 1.03–1.14(2H, m), 1.17–1.25(2H, m), 1.63(1H, t, J=12.8Hz), 1.87(1H, br d, J=11.2Hz), 2.19(1H, dt, J=4.9, 14.0Hz), 2.32(4.5H, s), 2.43–2.54(2H, m), 2.76(1H, dd, J=6.9, 19.5Hz), 2.80–2.94(4H, m), 3.02–3.10(1H, m), 3.21–3.27(1H, m)3.27(1H, d, J=19.5Hz), 3.37–3.44(1H, m), 3.79(1H, d, J=6.7Hz), 3.89–3.95(1H, m), 4.31(1H, s), 6.53(1H, d, J=7.9Hz), 6.68(1H, d, J=7.9Hz), 7.18(1H, t, J=7.3Hz), 7.23(2H, t, J=7.3Hz), 7.28(2H, t, J=7.3Hz), 7.86(1H, d, J=7.6Hz), 8.15(1H, br s), 9.32(1H, br s) | m.p. 145(dec) (° C.). Elemental Analysis C.F.* C$_{31}$H$_{36}$N$_2$O$_4$.0.2H$_2$O.1.5MeSO$_3$H Calcd. C, 60.20; H, 6.59; N, 4.32; S, 7.42 Found C, 60.01; H, 6.71; N, 4.36; S, 7.43 IR (cm$^{-1}$) (KBr) 3400, 3082, 1639, 1547, 1502, 1463, 1322, 1209, 1050, 784, 560 Mass (FAB) 501 ((M+H)+) |
| Compound 55 methanesulfonic acid salt Yield 84(%) 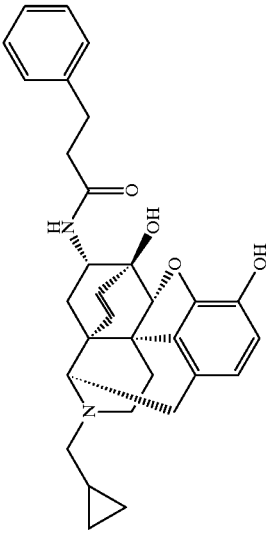 | NMR (ppm) (600 MHz, DMSO-d6) 0.35–0.41(1H, m), 0.42–0.48(1H, m), 0.58–0.71(3H, m), 1.03–1.14(2H, m), 1.19(1H, dd, J=4.9, 13.4Hz), 1.25(1H, dt, J=6.1, 12.5Hz), 1.66(1H, t, J=12.8Hz), 1.87(1H, br d, J=14.3Hz), 2.25(1H, dt, J=4.9, 14.0Hz), 2.31(3H, s), 2.46–2.53(2H, m), 2.78(1H, dd, J=6.7, 19.5Hz), 2.80–2.96(4H, m), 3.07–3.17(1H, m), 3.13(3H, s), 3.22–3.27(1H, m), 3.28(1H, d, J=19.5Hz), 3.35–3.44(1H, m), 3.82(1H, d, J=6.7Hz), 4.25–4.31(1H, m), 4.81(1H, s), 6.54(1H, d, J=7.9Hz), 6.68(1H, d, J=7.9Hz), 7.18(1H, t, J=7.3Hz), 7.23(2H, d, J=7.3Hz), 7.27(2H, t, J=7.3Hz), 7.91(1H, d, J=8.5Hz), 8.22(1H, br s), 9.29(1H, br s) | m.p. 165(dec) (° C.). Elemental Analysis C.F.* C$_{32}$H$_{38}$N$_2$O$_4$.0.6H$_2$O.MeSO$_3$H Calcd. C, 63.77; H, 7.01; N, 4.51; S, 5.16 Found C, 63.81; H, 7.13; N, 4.54; S, 5.13 IR (cm$^{-1}$) (KBr) 3408, 3278, 3082, 2948, 1646, 1559, 1504, 1457, 1323, 1212, 1170, 1100, 1042, 954, 775, 557 Mass (FAB) 515 ((M+H)+) |
| Compound 3 methanesulfonic acid salt Yield 74(%) 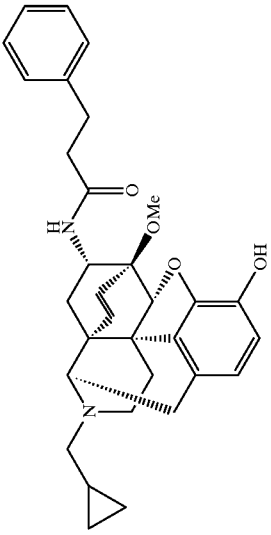 | NMR (ppm) (500 MHz, DMSO-d6) 0.35–0.48(2H, m), 0.55–0.73(3H, m), 1.03–1.13(2H, m), 1.33(1H, dt, J=6.4, 12.5Hz), 1.73(1H, t, J=12.5Hz), 1.86–1.93(2H, m), 2.14(1H, dt, J=4.4, 13.8Hz), 2.32(3H, s), 2.40–2.63(2H, m), 2.68–2.81(3H, m), 2.82–2.97(2H, m), 3.20–3.32(3H, m), 3.34–3.45(2H, m), 3.89(1H, d, J=6.8Hz), 4.17(1H, s), 5.02(1H, br s), 6.54(1H, d, J=8.3Hz), 6.68(1H, d, J=7.8Hz), 7.17–7.33(5H, m), 7.80(1H, br t, J=5.1Hz), 8.11(1H, br s), 9.28(1H, br s) | m.p. 160(dec) (° C.). Elemental Analysis Chemical Formula Calcd. Found IR (cm$^{-1}$) (KBr) 3404, 2942, 1653, 1547, 1504, 1463, 1323, 1209, 1048, 783, 703 Mass (FAB) 501 ((M+H)+) |
| Compound 56 methanesulfonic acid salt Yield 51(%) 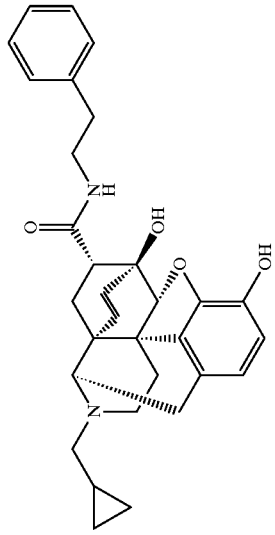 | | |

-continued

| | | |
|---|---|---|
| Compound 57<br>Yield 54(%)<br>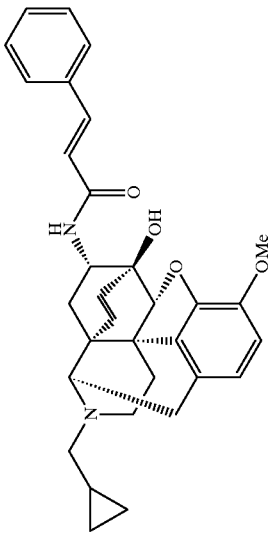 | NMR (ppm) (300 MHz, CDCl3)<br>0.04–0.21(2H, m), 0.41–0.59(1H, m), 0.75–0.92(1H, m), 1.04(1H, dd, J=4.7, 13.7Hz), 1.84(1H, br d, J=9.9Hz), 2.10(1H, dt, J=5.4, 12.7Hz), 2.29–2.49(4H, m), 2.74(1H, dd, J=4.8, 12.2Hz), 3.11(1H, d, J=18.7Hz), 3.45–3.60(2H, m), 3.82(3H, s), 4.26–4.36(1H, m), 4.46(1H, d, J=1.1Hz), 5.57(1H, d, J=8.5Hz), 5.70(1H, br s), 5.72(1H, d, J=8.8Hz), 6.38(1H, d, J=15.6Hz), 6.52(1H, d, J=8.2Hz), 6.62(1H, d, J=8.2Hz), 7.29–7.40(3H, m), 7.42–7.51(2H, m), 7.62(1H, d, J=15.4Hz) | m.p. (° C.).<br>Elemental Analysis<br>Chemical Formula<br>Calcd.<br>Found<br>IR (cm$^{-1}$) (KBr)<br>3306, 3068, 3004, 2928, 2834, 1660, 1625, 1539, 1499, 1451, 1357, 1285, 1214, 1161, 1106, 1055, 985, 928<br>Mass (EI) 510 (M+) |
| Compound 58<br>methanesulfonic acid salt<br>Yield 62(%)<br>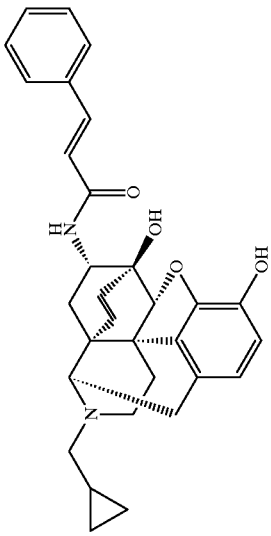 | NMR (ppm) (300 MHz, DMSO-d6)<br>0.36–0.54(2H, m), 0.57–0.77(2H, m), 1.01–1.19(1H, m), 1.08(1H, dd, J=4.4, 13.2Hz), 1.98–2.09(1H, m), 2.16–2.30(1H, m), 2.32(3H, s), 2.87–3.08(3H, m), 3.22–3.57(4H, m), 4.04–4.14(1H, m), 4.32(1H, d, J=6.9Hz), 4.46(1H, s), 5.64(1H, d, J=8.8Hz), 5.70(1H, d, J=8.8Hz), 6.47(1H, d, J=8.2Hz), 6.83(1H, d, J=8.0Hz), 6.82(1H, d, J=15.7Hz), 7.33–7.46(3H, m), 7.41(1H, d, J=15.9Hz), 7.52–7.59(2H, m), 7.80(1H, d, J=7.1Hz), 8.41(1H, br s), 9.15(1H, br s) | m.p. 170(dec)(° C.).<br>Elemental Analysis<br>C.F.* $C_{31}H_{33}N_2O_4 \cdot 0.9H_2O \cdot MeSO_3H$<br>Calcd. C, 63.12; H, 6.26; N, 4.60; S, 5.27<br>Found C, 62.76; H, 6.47; N, 4.63; S, 5.64<br>IR (cm$^{-1}$) (KBr)<br>3396, 3064, 2942, 1659, 1618, 1545, 1503, 1360, 1322, 1209, 1046, 783, 773<br>Mass (EI) 496 (M+) (data of free salt) |
| Compound 59<br>methanesulfonic acid salt<br>Yield 53(%)<br>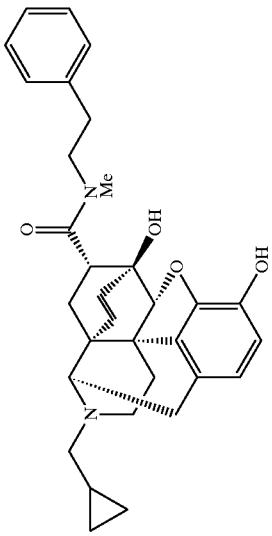 | NMR (ppm) (300 MHz, DMSO-d6)<br>0.33–0.51(2H, m), 0.51–0.75(3H, m), 0.98–1.15(2H, m), 1.29–1.48(1H, m), 1.72–1.94(3H, m), 2.25–2.40(1H, m), 2.32(3H, s), 2.52–3.00(5.5H, m), 2.79(1.5H, s), 3.06(1.5H, s), 3.09–3.30(3H, m), 3.30–3.76(5H, m), 3.84–4.04(1.5H, m), 4.38(1H, s), 6.54(0.5H, d, J=8.2Hz), 6.55(0.5H, d, J=8.2Hz), 6.68(0.5H, d, J=8.0Hz), 6.69(0.5H, d, J=8.0Hz), 7.17–7.35(5H, m), 8.14(1H, br s), 9.32(1H, br s) | m.p. 170 (° C.).<br>Elemental Analysis<br>C.F.* $C_{32}H_{38}N_2O_4 \cdot 1.1MeSO_3H \cdot 0.7H_2O$<br>Calcd. C, 62.81; H, 6.97; N, 4.43; S, 5.57<br>Found C, 62.90; H, 6.70; N, 4.43; S, 5.65<br>IR (cm$^{-1}$) (KBr)<br>3454, 3428, 2940, 1625, 1498, 1462, 1421, 1204, 1048<br>Mass (FAB) 515 ((M+H)+) |

-continued

| | | |
|---|---|---|
| Compound 60<br>Yield 64(%)<br>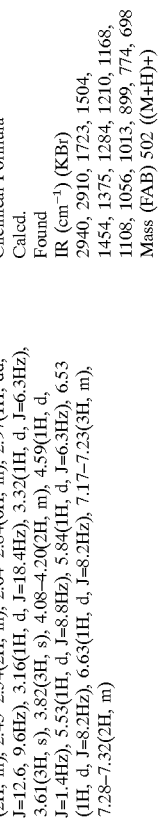 | NMR (ppm) (300 MHz, CDCl3)<br>1.26(3H, t, J=7.1Hz), 1.38(1H, dd, J=12.6, 6.3Hz), 1.81–1.99 (2H, m), 2.43–2.54(2H, m), 2.64–2.84(6H, m), 2.97(1H, dd, J=12.6, 9.6Hz), 3.16(1H, d, J=18.4Hz), 3.32(1H, d, J=6.3Hz), 3.61(3H, s), 3.82(3H, s), 4.08–4.20(2H, m), 4.59(1H, d, J=1.4Hz), 5.53(1H, d, J=8.8Hz), 5.84(1H, d, J=6.3Hz), 6.53 (1H, d, J=8.2Hz), 6.63(1H, d, J=8.2Hz), 7.17–7.23(3H, m), 7.28–7.32(2H, m) | m.p. (° C.),<br>Elemental Analysis<br>Chemical Formula<br>Calcd.<br>Found<br>IR (cm⁻¹) (KBr)<br>2940, 2910, 1723, 1504, 1454, 1375, 1284, 1210, 1168, 1108, 1056, 1013, 899, 774, 698<br>Mass (FAB) 502 ((M+H)+) |
| Compound 61<br>hydrohloric acid salt<br>Yield 65(%)<br>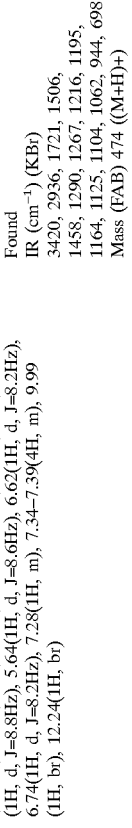 | NMR (ppm) (500 MHz, DMSO-d6)<br>1.49(1H, d, J=12.8, 6.2Hz), 1.99(1H, m), 2.31(1H, m), 2.90–3.14(5H, m), 3.27–3.45(4H, m), 3.52–3.62 (2H, m), 3.73(3H, s), 4.34(1H, d, J=7.0Hz), 4.94(1H, s), 5.54 (1H, d, J=8.8Hz), 5.64(1H, d, J=8.6Hz), 6.62(1H, d, J=8.2Hz), 6.74(1H, d, J=8.2Hz), 7.28(1H, m), 7.34–7.39(4H, m), 9.99 (1H, br), 12.24(1H, br) | m.p. 180–189 (° C.),<br>Elemental Analysis<br>Chemical Formula<br>Calcd.<br>Found<br>IR (cm⁻¹) (KBr)<br>3420, 2936, 1721, 1506, 1458, 1290, 1267, 1216, 1195, 1164, 1125, 1104, 1062, 944, 698<br>Mass (FAB) 474 ((M+H)+) |
| Compound 62<br>Yield 83(%)<br>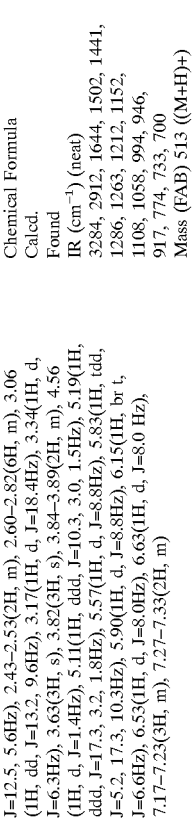 | NMR (ppm) (300 MHz, CDCl3)<br>1.49(1H, dd, J=13.2, 6.3Hz), 1.84(1H, m), 1.97(1H, td, J=12.5, 5.6Hz), 2.43–2.53(2H, m), 2.60–2.82(6H, m), 3.06 (1H, dd, J=13.2, 9.6Hz), 3.17(1H, d, J=18.4Hz), 3.34(1H, d, J=6.3Hz), 3.63(3H, s), 3.82(3H, s), 3.84–3.89(2H, m), 4.56 (1H, d, J=1.4Hz), 5.11(1H, ddd, J=10.3, 3.0, 1.5Hz), 5.19(1H, ddd, J=17.3, 3.2, 1.8Hz), 5.57(1H, d, J=8.8Hz), 5.83(1H, tdd, J=5.2, 17.3, 10.3Hz), 5.90(1H, d, J=8.8Hz), 6.15(1H, br t, J=6.6Hz), 6.53(1H, d, J=8.0Hz), 6.63(1H, d, J=8.0 Hz), 7.17–7.23(3H, m), 7.27–7.33(2H, m) | m.p. (° C.),<br>Elemental Analysis<br>Chemical Formula<br>Calcd.<br>Found<br>IR (cm⁻¹) (neat)<br>3284, 2912, 1644, 1502, 1441, 1286, 1263, 1212, 1152, 1108, 1058, 994, 946, 917, 774, 733, 700<br>Mass (FAB) 513 ((M+H)+) |

-continued

| | | |
|---|---|---|
| Compound 63<br>Yield 89(%) | 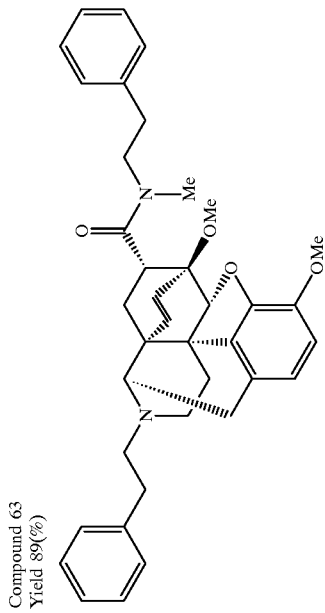 | NMR (ppm) (300 MHz, CDCl3)<br>1.31(1H, m), 1.68–2.00(2H, m), 2.41–2.56(2.5H, m),<br>2.61–2.90(8.5H, m), 2.93(1.5H, s), 3.03(1.5H, s), 3.13<br>(0.5H, d, J=17.9Hz), 3.16(0.5H, d, J=18.1Hz), 3.28(0.5H, d,<br>J=6.3Hz), 3.33(0.5H, s), 3.61(1.5H, s), 3.81(1.5H, s), 3.82(1.5H, s), 3.88<br>(1.5H, s), 3.45–3.67(1.5H, m), 3.58<br>(0.5H, m), 4.32(0.5H, d, J=1.4Hz), 4.47(0.5H, d, J=1.4Hz),<br>5.50(0.5H, d, J=8.8Hz), 5.52(0.5H, d, J=8.8Hz), 6.03(0.5H, d,<br>J=8.8Hz), 6.13(0.5H, d, J=8.2Hz), 6.50(0.5H, d, J=8.2Hz),<br>6.53(0.5H, d, J=8.2Hz), 6.61(0.5H, d, J=8.2Hz), 6.63(0.5H,<br>d, J=8.2Hz), 7.16–7.37(10H, m) | m.p. (° C.),<br>Elemental Analysis<br>Chemical Formula<br>Calcd.<br>Found<br>IR (cm⁻¹) (neat)<br>3400, 2932, 1636, 1497, 1454,<br>1210, 1164, 1110, 911,<br>733, 698<br>Mass (FAB) 591 ((M+H)+) |
| Compound 64<br>methanesulfonic acid salt<br>Yield 76(%) | 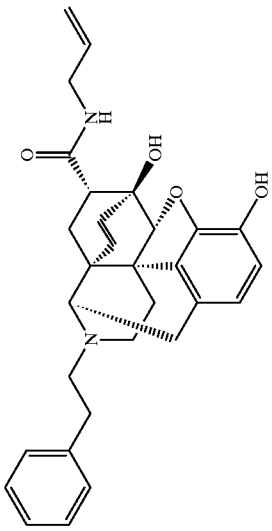 | NMR (ppm) (300 MHz, CDCl3) (data of free salt)<br>1.32(1H, dd, J=12.9, 6.3Hz), 1.83(1H, m), 1.92(1H, td,<br>J=12.1, 5.2Hz), 2.40–2.55(3H, m), 2.64–2.82(5H, m), 2.92<br>(1H, dd, J=12.9, 10.0Hz), 3.12(1H, d, J=18.4Hz), 3.29(1H, d,<br>J=6.3Hz), 3.84–3.90(2H, m), 4.37(1H, d, J=1.1Hz), 5.14(1H,<br>ddd, J=10.3, 3.0, 1.4Hz), 5.20(1H, ddd, J=17.3, 3.0, 1.6Hz),<br>5.23(1H, br), 5.39(1H, d, J=8.8Hz), 5.75(1H, d, J=8.8Hz),<br>5.82(1H, tdd, J=5.5, 17.3, 10.3Hz), 6.05(1H, t, J=5.6Hz), 6.34<br>(1H, br), 6.46(1H, d, J=8.2Hz), 6.60(1H, d, J=8.2Hz),<br>7.16–7.24(3H, m), 7.27–7.32(2H, m) | m.p. 170(dec)(° C.),<br>Elemental Analysis<br>C.F.* C30H32N2O4.1.1MeSO3H.0.4H2O<br>Calcd. C, 62.52; H, 6.28; N, 4.69; S, 5.90<br>Found C, 62.35; H, 6.44; N, 4.74; S, 5.95<br>IR (cm⁻¹) (KBr)<br>3316, 1657, 1640, 1547, 1502,<br>1460, 1323, 1209, 1060,<br>1044, 922, 785, 702<br>Mass (FAB) 485 ((M+H)+) |
| Compound 65<br>methanesulfonic acid salt<br>Yield 60(%) | 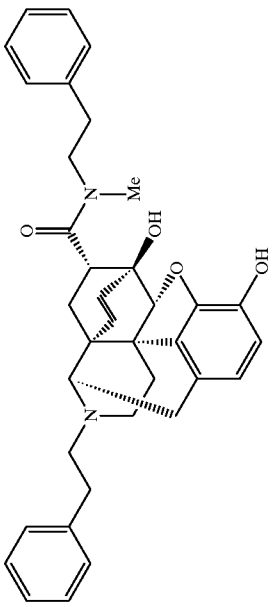 | NMR (ppm) (300 MHz, CDCl3) (data of free salt)<br>0.89(0.6H, dd, J=12.6, 6.9Hz), 1.00(0.4H, dd, J=12.6, 6.9Hz),<br>1.68–1.95(2H, m), 2.20(0.4H, m), 2.38–2.55(2H, m),<br>2.63–3.01(8.6H, m), 2.89(1.8H, s), 2.95(1.2H, s), 3.11<br>(0.6H, d, J=18.4Hz), 3.14(0.4H, d, J=18.4Hz), 3.21(0.4H, d,<br>J=6.3Hz), 3.23(0.6H, d, J=6.3Hz), 3.40–3.69(2H, m), 4.09<br>(0.4H, d, J=1.1Hz), 4.40(0.6H, d, J=1.1Hz), 4.43(0.4H, br d,<br>J=1.1Hz), 4.65(0.6H, br d, J=1.1Hz), 5.28(0.4H, d, J=8.5Hz),<br>5.31(0.6H, d, J=8.5Hz), 5.38(1H, br), 5.83(0.4H, d, J=8.5Hz),<br>5.92(0.6H, d, J=8.5Hz), 6.45(0.4H, d, J=8.0Hz), 6.47(0.6H,<br>d, J=8.0Hz), 6.60(0.4H, d, J=8.0Hz), 6.62(0.6H, d, J=8.0Hz),<br>7.12–7.41(10H, m) | m.p. 165(dec)(° C.),<br>Elemental Analysis<br>C.F.* C36H38N2O4.MeSO3H.0.6H2O<br>Calcd. C, 66.37; H, 6.50; N, 4.18; S, 4.79<br>Found C, 66.16; H, 6.51; N, 4.30; S, 5.15<br>IR (cm⁻¹) (KBr)<br>3400, 1630, 1499, 1458, 1323,<br>1166, 1042, 924, 783,<br>775, 758, 702<br>Mass (FAB) 563 ((M+H)+) |

*Chemical Formula

Example 55
Opioid Activity Test Using the Isolated Rat Vas Deferens Preparation Specimens of the isolated vas deferens of rats are specimens on which β-endorphin specifically act, and are reported to have opioid-ε receptors thereon (Wuster et al., Neurosci. Lett., 15, 193(1979); Life Sci., 27, 163(1980); Schulz et al., J. Pharmacol. Exp. Ther., 216, 604 (1981)). Therefore, by using the isolated rat vas deferens preparations, the action of a test compound on opioid ε-receptor can be evaluated.

Male SD rats were used in this experiment. In Magnus tube filled with Ringer's solution (NaCl 154 mM; KCl 5.66 mM; $CaCl_2$ 2.54 mM; Glucose 2.77 mM; $NaHCO_3$ 5.95 mM; Tyrosine 0.0018 mM) kept at 37° C. and gassed with 5% carbon dioxide and 95% oxygen, vas deferens preparations removed from rats mercy-killed by bleeding under anesthesia or after clubbing the head to death were suspended. Electrical stimulation was given through ring-shaped platinum electrodes located above and below the specimen at 100–150 mA, 0.2 Hz for 0.5 mS. Tissue contraction was recorded on a polygraph using an isometric transducer. The agonist activity is shown in terms of both the degree of inhibition of contraction and the concentration of the added compound at the time the compound's inhibitory effect on the specimen induced by the electrical stimulation reached plateau after the cumulative addition of a test compound. The antagonist activity is shown in terms of the Ke value calculated according to the following equation:

$$Ke = [\text{Concentration of Antagonist Added}]/(DR-1)$$

wherein DR represents the dose ratio obtained by the parallel line assay between the dose response curve obtained by cumulatively adding β-endorphin about 15 minutes after the addition of a test compound followed a stabilization of the contraction response, and the dose response curve obtained by adding β-endorphin alone. The results are shown in Tables 1 and 2 below.

TABLE 1

ε-Opioid Agonist Activities of Compounds

| Compound | Inhibition of Contraction (%) | Concentration of Compound (μM) |
|---|---|---|
| Compound 1 · methanesulfonic acid salt | 32 | 2.5 |
| Compound 22 · methanesulfonic acid salt | 70 | 1.0 |
| Compound 59 · methanesulfonic acid salt | 61 | 2.2 |
| Compound 65 · methanesulfonic acid salt | 55 | 1.0 |

TABLE 2

ε-Opioid Antagonist Activities of Compounds

| Compound | Ke Value (nM) |
|---|---|
| Compound 18 · methanesulfonic acid salt | 0.56 |
| Compound 19 · methanesulfonic acid salt | 1.7 |
| Compound 20 · methanesulfonic acid salt | 0.71 |
| Compound 25 · methanesulfonic acid salt | 0.51 |
| Compound 26 · methanesulfonic acid salt | 0.41 |
| Compound 28 · methanesulfonic acid salt | 0.83 |
| Compound 52 · methanesulfonic acid salt | 0.18 |
| Compound 53 · methanesulfonic acid salt | 0.83 |

Example 56
Analgesic Activity Test Using the Acetic Acid-induced Writhing Method In the experiment, ddy mice of 5 weeks old were used. To the mice, 0.6% aqueous acetic acid solution was intraperitoneally administered at a dose of 0.1 ml/10 g body weight. The analgesic activity was evaluated based on the number of writhing reactions occurred during a time period of 10 minutes beginning from 10 minutes after the administration. The test compound was subcutaneously administered through the back of the mouse 15 minutes before the administration of acetic acid. The results are shown in Table 3.

TABLE 3

Analgesic Activities of Compounds

| Compound | $ED_{50}$ Value (μg/kg body weight) |
|---|---|
| Compound 1 · methanesulfonic acid salt | 238.8 |
| Compound 22 · methanesulfonic acid salt | 17.7 |

Example 57
Analgesic Activity Test Using the Hot Plate Method

In the experiment, ddy mice of 5 weeks old were used. Each mouse was placed on a hot plate. The analgesic activity was evaluated based on the time period from placing the mouse on the hot plate to the time at which the mouse began an escape reaction (licking the limbs, shaking the limbs or jumping). To prevent damage of the tissue, the cut-off time was set to 30 seconds. The test compound was subcutaneously administered from the back of the mouse 30 minutes before measuring the analgesic action. As a result, the $ED_{50}$ of the analgesic activity of Compound 1.methanesulfonic acid salt was 2.64 mg/kg body weight.

INDUSTRIAL AVAILABILITY

In vitro and in vivo activity tests revealed that the compounds according to the present invention have agonist activities or antagonist activities as compounds having abilities to bind to opioid ε-receptor. Opioid ε-receptor agonists may be used as analgesics, and Opioid ε-receptor antagonists may be used as important tools for the pharmacological studies of this receptor.

We claim:
1. A morphinan derivative of the formula (I):

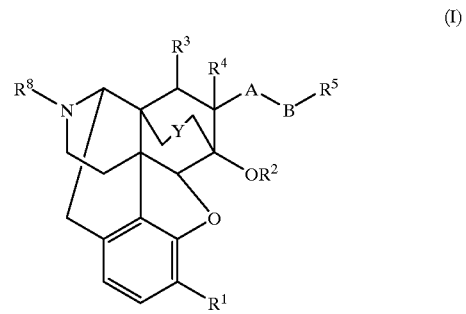

wherein
Y is single bond or double bond;
$R^1$ is hydrogen, hydroxy, $C_1$–$C_5$ alkoxy, $C_1$–$C_5$ alkanoyloxy or $C_7$–$C_{13}$ aralkyloxy;
$R^2$ is hydrogen or $C_1$–$C_5$ alkyl;
$R^3$ and $R^4$ independently are hydrogen, fluorine, chlorine, bromine, iodine, $C_1$–$C_5$ alkyl or phenyl;

A is —X(=O)—NR⁶— or —NR⁶—X(=O)—, wherein X is carbon or S=O, R⁶ is hydrogen, $C_1$–$C_5$ alkyl, $C_3$–$C_7$ alkenyl, $C_3$–$C_7$ alkynyl, $C_6$–$C_{12}$ aryl or $C_7$–$C_{13}$ aralkyl;

B is
(1) valence bond,
(2) $C_1$–$C_{14}$ straight or branched alkylene, wherein said $C_1$–$C_{14}$ straight or branched alkylene may be substituted with at least one substituent selected from the group consisting of $C_1$–$C_5$ alkoxy, $C_1$–$C_5$ alkanoyloxy, hydroxy, fluorine, chlorine, bromine, iodine, amino, nitro, cyano, trifluoromethyl, phenyl and phenoxy, and that 1 to 3 methylene groups therein may be substituted by carbonyl group,
(3) $C_2$–$C_{14}$ linear or branched acyclic unsaturated hydrocarbon containing 1 to 3 double bonds and/or triple bonds, wherein said $C_2$–$C_{14}$ linear or branched acyclic unsaturated hydrocarbon may be substituted with at least one substituent selected from the group consisting of $C_1$–$C_5$ alkoxy, $C_1$–$C_5$ alkanoyloxy, hydroxy, fluorine, chlorine, bromine, iodine, amino, nitro, cyano, trifluoromethyl, phenyl and phenoxy, and that 1 to 3 methylene groups therein may be substituted by carbonyl group, or
(4) $C_1$–$C_{14}$ straight or branched saturated or unsaturated hydrocarbon containing 1 to 5 thioether bonds, ether bonds and/or amino bonds, wherein 1 to 3 methylene groups in said $C_1$–$C_{14}$ straight or branched saturated or unsaturated hydrocarbon may be substituted by carbonyl group;

$R^5$ is hydrogen, cyano, or an organic group having the following skeleton:

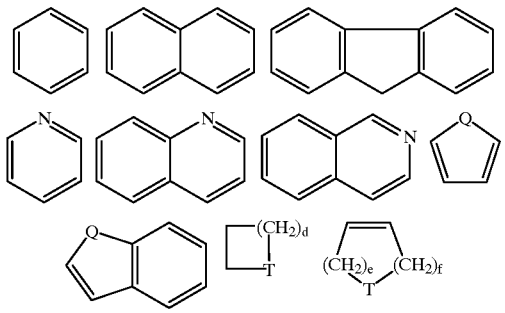

wherein
Q is —NH—, —S— or —O—,
T is —CH₂—, —NH—, —S— or —O—,
d is a number from 0 to 5, and
e and f independently are numbers of not less than 0 whereas the total of e and f is not more than 5,
wherein said organic group may be substituted with at least one substituent selected from the group consisting of $C_1$–$C_5$ alkyl, $C_1$–$C_5$ alkoxy, $C_1$–$C_5$ alkanoyloxy, hydroxy, $C_1$–$C_5$ alkoxycarbonyl, fluorine, chlorine, bromine, iodine, amino, nitro, cyano, isothiocyanato, trifluoromethyl, phenyl, phenoxy and methylenedioxy, wherein
(1) when A is —X(=O)—NR⁶—, —B—R⁵, R⁶ and nitrogen to which —B—R⁵ and R⁶ are bound may cooperatively form a heterocyclic ring selected from the group consisting of morpholine, piperidine, pyrrolidine, piperazine, N-methylpiperazine, N-phenylpiperazine, indoline, tetrahydroquinoline and tetrahydroisoquinoline, or
(2) when A is —NR⁶—X(=O)—, —B—R⁵ and R⁶ may cooperatively form $C_2$–$C_6$ alkylene or

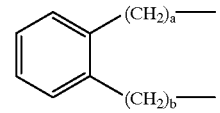

wherein a and b independently are numbers of not less than 0, the total of a and b being not more than 4; and $R^8$ is $C_4$–$C_7$ cycloalkylalkyl or $C_7$–$C_{13}$ aralkyl;
or a pharmaceutically acceptable acid addition salt thereof, provided that when A is —NH—C(=O)—, B is not —CH=CH— or R⁵ is not hydrogen.

2. The morphinan derivative or the pharmaceutically acceptable acid addition salt thereof according to claim 1, wherein said A is —C(=O)—NR⁶—, wherein R⁶ has the same meanings as defined above.

3. The morphinan derivative or the pharmaceutically acceptable acid addition salt thereof according to claim 2, wherein said R⁶ is $C_1$–$C_5$ alkyl, $C_3$–$C_7$ alkenyl, $C_3$–$C_7$ alkynyl, $C6$–$C_{12}$ aryl, or $C_7$–$C_{13}$ aralkyl.

4. The morphinan derivative or the pharmaceutically acceptable acid addition salt thereof according to claim 1, wherein said A is —NR⁶—C(=O)—, wherein R⁶ has the same meanings as defined above.

5. The morphinan derivative or a pharmaceutically acceptable acid addition salt thereof according to claim 1, wherein said R⁸ is cyclopropylmethyl.

6. A pharmaceutical composition comprising as an effective component an effective amount of said morphinan derivative or the pharmaceutically acceptable acid addition salt thereof according to claim 1.

7. A method for treating pain comprising administering an effective amount of said morphinan derivative or the pharmaceutically acceptable acid addition salt thereof according to claim 1.

8. A method for treating pain comprising administering an effective amount of said morphinan derivative or the pharmaceutically acceptable acid addition salt thereof according to claim 1, which has an opioid ε-receptor agonist activity.

* * * * *